US009795536B2

(12) United States Patent
Lev et al.

(10) Patent No.: US 9,795,536 B2
(45) Date of Patent: Oct. 24, 2017

(54) LIQUID DRUG TRANSFER DEVICES EMPLOYING MANUAL ROTATION FOR DUAL FLOW COMMUNICATION STEP ACTUATIONS

(71) Applicant: MEDIMOP Medical Projects Ltd., Ra'anana (IL)

(72) Inventors: Nimrod Lev, Savion (IL); Niv Ben Shalom, Netanya (IL)

(73) Assignee: Medimop Medical Projects, Ltd., Ra'anana (IL)

(*) Notice: Subject to any disclaimer, the term of this patent is extended or adjusted under 35 U.S.C. 154(b) by 408 days.

(21) Appl. No.: 14/423,612

(22) PCT Filed: Aug. 26, 2013

(86) PCT No.: PCT/IL2013/050721
§ 371 (c)(1),
(2) Date: Feb. 24, 2015

(87) PCT Pub. No.: WO2014/033710
PCT Pub. Date: Mar. 6, 2014

(65) Prior Publication Data

US 2015/0297462 A1 Oct. 22, 2015

Related U.S. Application Data

(60) Provisional application No. 61/731,574, filed on Nov. 30, 2012.

(30) Foreign Application Priority Data

Aug. 26, 2012 (IL) .......................................... 221635

(51) Int. Cl.
*A61B 19/00* (2006.01)
*A61J 1/22* (2006.01)
(Continued)

(52) U.S. Cl.
CPC . *A61J 1/22* (2013.01); *A61J 1/18* (2013.01); *A61J 1/201* (2015.05); *A61J 1/2048* (2015.05);
(Continued)

(58) Field of Classification Search
CPC .... A61J 1/10; A61J 1/18; A61J 1/1406; A61J 1/201; A61J 1/2013; A61J 1/2048;
(Continued)

(56) References Cited

U.S. PATENT DOCUMENTS 62,333 A 2/1867 Holl
1,021,681 A 3/1912 Jennings
(Continued)

FOREIGN PATENT DOCUMENTS

CN 1950049 A 4/2007
DE 1913926 A1 9/1970
(Continued)

OTHER PUBLICATIONS

Grifols Vial Adapter Product Literature, 2 pages, Jan. 2002.
(Continued)

*Primary Examiner* — Philip R Wiest
(74) *Attorney, Agent, or Firm* — Panitch Schwarze Belisario & Nadel LLP

(57) ABSTRACT

Liquid drug transfer devices employing manual rotation of a drug vial adapter with respect to a liquid container adapter for dual flow communication step actuation for establishing flow communication between a liquid container containing liquid contents and an initially intact, namely, non-punctured, drug vial. Manual rotation compacts a liquid drug transfer device along a longitudinal device axis for urging a puncturing tip through a drug vial stopper during a drug vial flow communication step for flow communication with a drug vial interior. Manual rotation also executes a liquid
(Continued)

container flow communication step for flow communication with a liquid container, therefore establishing flow communication between a drug vial and a liquid container.

22 Claims, 27 Drawing Sheets

(51) Int. Cl.
*A61J 1/20* (2006.01)
*A61J 1/18* (2006.01)
*A61J 1/10* (2006.01)
*A61J 1/14* (2006.01)

(52) U.S. Cl.
CPC ................ *A61J 1/2089* (2013.01); *A61J 1/10* (2013.01); *A61J 1/1406* (2013.01); *A61J 1/2013* (2015.05); *A61J 1/2051* (2015.05); *A61J 1/2055* (2015.05); *A61J 1/2096* (2013.01)

(58) Field of Classification Search
CPC ...... A61J 1/2051; A61J 1/2055; A61J 1/2089; A61J 1/2096; A61J 1/22
USPC .................................................. 604/403–416
See application file for complete search history.

(56) References Cited

U.S. PATENT DOCUMENTS 1,704,817 A 3/1929 Ayers
1,930,944 A 10/1933 Schmitz, Jr.
2,326,490 A 8/1943 Perelson
2,931,668 A 4/1960 Baley
2,968,497 A 1/1961 Treleman
3,059,643 A 10/1962 Barton
D198,499 S 6/1964 Harautuneian
3,225,763 A 12/1965 Waterman
3,484,849 A 12/1969 Huebner et al.
3,618,637 A 11/1971 Santomieri
3,757,981 A 9/1973 Harris, Sr. et al.
3,788,524 A 1/1974 Davis et al.
3,822,700 A 7/1974 Pennington
3,826,261 A 7/1974 Killinger
3,872,992 A 3/1975 Larson
3,885,607 A 5/1975 Peltier
3,938,520 A 2/1976 Scislowicz et al.
3,957,052 A 5/1976 Topham
3,977,555 A 8/1976 Larson
3,993,063 A 11/1976 Larrabee
4,020,839 A 5/1977 Klapp
4,051,852 A 10/1977 Villari
D248,568 S 7/1978 Ismach
4,109,670 A 8/1978 Slagel
4,121,585 A 10/1978 Becker, Jr.
4,161,178 A 7/1979 Genese
4,187,848 A 2/1980 Taylor
4,203,067 A 5/1980 Fitzky et al.
4,203,443 A 5/1980 Genese
4,210,173 A 7/1980 Choksi et al.
D257,286 S 10/1980 Folkman
4,253,501 A 3/1981 Ogle
4,296,786 A 10/1981 Brignola
4,303,067 A 12/1981 Connolly et al.
4,312,349 A 1/1982 Cohen
4,314,586 A 2/1982 Folkman
4,328,802 A 5/1982 Curley et al.
4,335,717 A 6/1982 Bujan et al.
D267,199 S 12/1982 Koenig
4,376,634 A 3/1983 Prior et al.
D268,871 S 5/1983 Benham et al.
4,392,850 A 7/1983 Elias et al.
D270,282 S 8/1983 Gross
4,410,321 A 10/1983 Pearson et al.
4,411,662 A 10/1983 Pearson
D271,421 S 11/1983 Fetterman
4,434,823 A 3/1984 Hudspith
4,465,471 A 8/1984 Harris et al.
4,475,915 A 10/1984 Sloane
4,493,348 A 1/1985 Lemmons
4,505,709 A 3/1985 Froning et al.
4,507,113 A 3/1985 Dunlap
D280,018 S 8/1985 Scott
4,532,969 A 8/1985 Kwaan
4,564,054 A 1/1986 Gustavsson
4,573,993 A 3/1986 Hoag et al.
4,576,211 A 3/1986 Valentini et al.
4,581,014 A 4/1986 Millerd et al.
4,588,396 A 5/1986 Stroebel et al.
4,588,403 A 5/1986 Weiss et al.
D284,603 S 7/1986 Loignon
4,604,093 A 8/1986 Brown et al.
4,607,671 A 8/1986 Aalto et al.
4,614,437 A 9/1986 Buehler
4,638,975 A 1/1987 Iuchi et al.
4,639,019 A 1/1987 Mittleman
4,667,927 A 5/1987 Oscarsson
4,676,530 A 6/1987 Nordgren et al.
4,683,975 A 8/1987 Booth et al.
4,697,622 A 10/1987 Swift et al.
4,721,133 A 1/1988 Sundblom
4,729,401 A 3/1988 Raines
4,735,608 A 4/1988 Sardam
4,743,229 A 5/1988 Chu
4,743,243 A 5/1988 Vaillancourt
4,752,292 A 6/1988 Lopez et al.
4,758,235 A 7/1988 Tu
4,759,756 A 7/1988 Forman et al.
4,778,447 A 10/1988 Velde et al.
4,787,898 A 11/1988 Raines
4,797,898 A 1/1989 Martinez
4,804,366 A 2/1989 Zdeb et al.
4,832,690 A 5/1989 Kuu
4,834,152 A 5/1989 Howson et al.
D303,013 S 8/1989 Konopka
4,857,062 A 8/1989 Russell
4,865,592 A 9/1989 Rycroft
4,871,463 A 10/1989 Taylor et al.
4,898,209 A 2/1990 Zbed
4,909,290 A 3/1990 Coccia
4,931,040 A 6/1990 Haber et al.
4,932,944 A 6/1990 Jagger et al.
4,967,797 A 11/1990 Manska
D314,050 S 1/1991 Sone
D314,622 S 2/1991 Andersson et al.
4,997,430 A 3/1991 Van der Heiden et al.
5,006,114 A 4/1991 Rogers et al.
5,035,686 A 7/1991 Crittenden et al.
5,041,105 A 8/1991 D'Alo et al.
5,045,066 A 9/1991 Scheuble et al.
5,049,129 A 9/1991 Zdeb et al.
5,053,015 A 10/1991 Gross
5,061,248 A 10/1991 Sacco
5,088,996 A 2/1992 Kopfer et al.
5,096,575 A 3/1992 Cosack
5,104,387 A 4/1992 Pokorney et al.
5,113,904 A 5/1992 Aslanian
5,122,124 A 6/1992 Novacek et al.
5,125,908 A 6/1992 Cohen
5,125,915 A 6/1992 Berry et al.
D328,788 S 8/1992 Sagae et al.
5,171,230 A 12/1992 Eland et al.
5,201,705 A 4/1993 Berglund et al.
5,201,717 A 4/1993 Wyatt et al.
5,203,771 A 4/1993 Melker et al.
5,203,775 A 4/1993 Frank et al.
5,211,638 A 5/1993 Dudar et al.
5,232,029 A 8/1993 Knox et al.
5,232,109 A 8/1993 Tirrell et al.
5,242,432 A 9/1993 DeFrank
5,247,972 A 9/1993 Tetreault
D341,420 S 11/1993 Conn
5,269,768 A 12/1993 Cheung

(56) References Cited

U.S. PATENT DOCUMENTS 5,270,219 A 12/1993 DeCastro et al.
5,279,576 A 1/1994 Loo et al.
5,288,290 A 2/1994 Brody
5,300,034 A 4/1994 Behnke et al.
5,301,685 A 4/1994 Guirguis
5,304,163 A 4/1994 Bonnici et al.
5,304,165 A 4/1994 Haber et al.
5,308,483 A 5/1994 Sklar et al.
5,312,377 A 5/1994 Dalton
5,328,474 A 7/1994 Raines
D349,648 S 8/1994 Tirrell et al.
5,334,163 A 8/1994 Sinnett
5,334,179 A 8/1994 Poli et al.
5,342,346 A 8/1994 Honda et al.
5,344,417 A 9/1994 Wadsworth, Jr.
5,348,548 A 9/1994 Meyer et al.
5,350,372 A 9/1994 Ikeda et al.
5,364,386 A 11/1994 Fukuoka et al.
5,364,387 A 11/1994 Sweeney
5,374,264 A 12/1994 Wadsworth, Jr.
5,385,547 A 1/1995 Wong et al.
5,397,303 A 3/1995 Sancoff et al.
D357,733 S 4/1995 Matkovich
5,429,614 A 7/1995 Fowles et al.
5,433,330 A 7/1995 Yatsko et al.
5,445,630 A 8/1995 Richmond
5,445,631 A 8/1995 Uchida
D362,718 S 9/1995 Deily et al.
5,451,374 A 9/1995 Molina
5,454,805 A 10/1995 Brony
5,464,111 A 11/1995 Vacek et al.
5,464,123 A 11/1995 Scarrow
5,466,219 A 11/1995 Lynn et al.
5,466,220 A 11/1995 Brenneman
5,470,327 A 11/1995 Helgren et al.
5,471,994 A 12/1995 Guirguis
5,472,022 A 12/1995 Michel et al.
5,478,337 A 12/1995 Okamoto et al.
5,492,147 A 2/1996 Challender et al.
D369,406 S 4/1996 Niedospial et al.
5,505,714 A 4/1996 Dassa et al.
5,509,433 A 4/1996 Paradis
5,520,659 A 5/1996 Hedges
5,526,853 A 6/1996 McPhee et al.
5,527,306 A 6/1996 Haining
5,531,695 A 7/1996 Swisher
5,547,471 A 8/1996 Thompson et al.
5,549,577 A 8/1996 Siegel et al.
5,554,128 A 9/1996 Hedges
5,566,729 A 10/1996 Grabenkort et al.
5,569,191 A 10/1996 Meyer
5,573,281 A 11/1996 Keller
5,578,015 A 11/1996 Robb
5,583,052 A 12/1996 Portnoff et al.
5,584,819 A 12/1996 Kopfer
5,591,143 A 1/1997 Trombley, III et al.
5,603,706 A 2/1997 Wyatt et al.
5,607,439 A 3/1997 Yoon
5,611,576 A 3/1997 Guala
5,616,203 A 4/1997 Stevens
5,636,660 A 6/1997 Pfleiderer et al.
5,637,101 A 6/1997 Shillington
5,641,010 A 6/1997 Maier
5,645,538 A 7/1997 Richmond
5,647,845 A 7/1997 Haber et al.
5,651,776 A 7/1997 Appling et al.
5,653,686 A 8/1997 Coulter et al.
5,674,195 A 10/1997 Truthan
5,676,346 A 10/1997 Leinsing
5,685,845 A 11/1997 Grimard
D388,172 S 12/1997 Cipes
5,699,821 A 12/1997 Paradis
5,702,019 A 12/1997 Grimard
5,718,346 A 2/1998 Weiler
D393,722 S 4/1998 Fangrow, Jr. et al.
5,738,144 A 4/1998 Rogers
5,743,312 A 4/1998 Pfeifer et al.
5,746,733 A 5/1998 Capaccio et al.
5,755,696 A 5/1998 Caizza
5,766,211 A 6/1998 Wood et al.
5,772,630 A 6/1998 Ljungquist
5,772,652 A 6/1998 Zielinski
RE35,841 E 7/1998 Frank et al.
5,776,116 A 7/1998 Lopez et al.
5,782,872 A 7/1998 Muller
5,806,831 A 9/1998 Paradis
5,810,792 A 9/1998 Fangrow, Jr. et al.
D399,559 S 10/1998 Molina
5,817,082 A 10/1998 Niedospial, Jr. et al.
5,820,621 A 10/1998 Yale et al.
5,827,262 A 10/1998 Neftel et al.
5,832,971 A 11/1998 Yale et al.
5,833,213 A 11/1998 Ryan
5,834,744 A 11/1998 Risman
5,839,715 A 11/1998 Leinsing
5,853,406 A 12/1998 Masuda et al.
D405,522 S 2/1999 Hoenig et al.
5,871,110 A 2/1999 Grimard et al.
5,873,872 A 2/1999 Thibault et al.
5,879,337 A 3/1999 Kuracina et al.
5,879,345 A 3/1999 Aneas
5,887,633 A 3/1999 Yale et al.
5,890,610 A 4/1999 Jansen et al.
5,891,129 A 4/1999 Daubert et al.
5,893,397 A 4/1999 Peterson et al.
5,897,526 A 4/1999 Vaillancourt
5,899,468 A 5/1999 Apps et al.
5,902,280 A 5/1999 Powles et al.
5,902,298 A 5/1999 Niedospial, Jr. et al.
D410,740 S 6/1999 Molina
5,911,710 A 6/1999 Barry et al.
5,919,182 A 7/1999 Avallone
5,921,419 A 7/1999 Niedospial, Jr. et al.
5,924,584 A 7/1999 Hellstrom et al.
5,925,029 A 7/1999 Jansen et al.
5,935,112 A 8/1999 Stevens et al.
5,941,848 A 8/1999 Nishimoto et al.
5,944,700 A 8/1999 Nguyen et al.
5,954,104 A 9/1999 Daubert et al.
5,971,181 A 10/1999 Niedospial, Jr. et al.
5,971,965 A 10/1999 Mayer
5,989,237 A 11/1999 Fowles et al.
6,003,566 A 12/1999 Thibault et al.
6,004,278 A 12/1999 Botich et al.
6,019,750 A 2/2000 Fowles et al.
6,022,339 A 2/2000 Fowles et al.
6,036,171 A 3/2000 Weinheimer et al.
6,039,093 A 3/2000 Mrotzek et al.
6,039,302 A 3/2000 Cote, Sr. et al.
D422,357 S 4/2000 Niedospial, Jr. et al.
6,063,068 A 5/2000 Fowles et al.
D427,308 S 6/2000 Zinger
D427,309 S 6/2000 Molina
6,070,623 A 6/2000 Aneas
6,071,270 A 6/2000 Fowles et al.
6,080,132 A 6/2000 Cole et al.
D428,141 S 7/2000 Brotspies et al.
6,086,762 A 7/2000 Guala
6,089,541 A 7/2000 Weinheimer et al.
6,090,091 A 7/2000 Fowles et al.
6,090,093 A 7/2000 Thibault et al.
6,092,692 A 7/2000 Riskin
D430,291 S 8/2000 Jansen et al.
6,099,511 A 8/2000 Devos et al.
6,113,068 A 9/2000 Ryan
6,113,583 A 9/2000 Fowles et al.
6,117,114 A 9/2000 Paradis
D431,864 S 10/2000 Jansen
6,139,534 A 10/2000 Niedospial, Jr. et al.
6,142,446 A 11/2000 Leinsing
6,146,362 A 11/2000 Turnbull et al.
6,149,623 A 11/2000 Reynolds
6,156,025 A 12/2000 Niedospial, Jr. et al.
6,159,192 A 12/2000 Fowles et al.

(56) References Cited

U.S. PATENT DOCUMENTS

| | | | |
|---|---|---|---|
| 6,168,037 | B1 | 1/2001 | Grimard |
| 6,171,287 | B1 | 1/2001 | Lynn et al. |
| 6,171,293 | B1 | 1/2001 | Rowley et al. |
| 6,173,852 | B1 | 1/2001 | Browne |
| 6,173,868 | B1 | 1/2001 | DeJonge |
| 6,174,304 | B1 | 1/2001 | Weston |
| 6,179,822 | B1 | 1/2001 | Niedospial, Jr. |
| 6,179,823 | B1 | 1/2001 | Niedospial, Jr. |
| 6,206,861 | B1 | 3/2001 | Mayer |
| 6,221,041 | B1 | 4/2001 | Russo |
| 6,221,054 | B1 | 4/2001 | Martin et al. |
| 6,221,065 | B1 | 4/2001 | Davis |
| 6,238,372 | B1 | 5/2001 | Zinger et al. |
| 6,245,044 | B1 | 6/2001 | Daw et al. |
| D445,501 | S | 7/2001 | Niedospial, Jr. |
| D445,895 | S | 7/2001 | Svendsen |
| 6,253,804 | B1 | 7/2001 | Safabash |
| 6,258,078 | B1 | 7/2001 | Thilly |
| 6,280,430 | B1 | 8/2001 | Neftel et al. |
| 6,290,688 | B1 | 9/2001 | Lopez et al. |
| 6,296,621 | B1 | 10/2001 | Masuda et al. |
| 6,299,131 | B1 | 10/2001 | Ryan |
| 6,343,629 | B1 | 2/2002 | Wessman et al. |
| 6,348,044 | B1 | 2/2002 | Coletti et al. |
| 6,358,236 | B1 | 3/2002 | DeFoggi et al. |
| 6,364,866 | B1 | 4/2002 | Furr et al. |
| 6,378,576 | B2 | 4/2002 | Thibault et al. |
| 6,378,714 | B1 | 4/2002 | Jansen et al. |
| 6,379,340 | B1 | 4/2002 | Zinger et al. |
| D457,954 | S | 5/2002 | Wallace et al. |
| 6,382,442 | B1 | 5/2002 | Thibault et al. |
| 6,386,397 | B2 | 5/2002 | Brotspies et al. |
| 6,408,897 | B1 | 6/2002 | Laurent et al. |
| 6,409,708 | B1 | 6/2002 | Wessman |
| 6,440,107 | B1 | 8/2002 | Trombley, III et al. |
| 6,453,949 | B1 | 9/2002 | Chau |
| 6,453,956 | B2 | 9/2002 | Safabash |
| 6,474,375 | B2 | 11/2002 | Spero et al. |
| 6,478,788 | B1 | 11/2002 | Aneas |
| D468,015 | S | 12/2002 | Horppu |
| 6,499,617 | B1 | 12/2002 | Niedospial, Jr. et al. |
| 6,503,240 | B1 | 1/2003 | Niedospial, Jr. et al. |
| 6,503,244 | B2 | 1/2003 | Hayman |
| 6,520,932 | B2 | 2/2003 | Taylor |
| 6,524,278 | B1 | 2/2003 | Campbell et al. |
| 6,524,295 | B2 | 2/2003 | Daubert et al. |
| D472,316 | S | 3/2003 | Douglas et al. |
| 6,530,903 | B2 | 3/2003 | Wang et al. |
| 6,537,263 | B1 | 3/2003 | Aneas |
| D472,630 | S | 4/2003 | Douglas et al. |
| 6,544,246 | B1 | 4/2003 | Niedospial, Jr. |
| 6,551,299 | B2 | 4/2003 | Miyoshi et al. |
| 6,558,365 | B2 | 5/2003 | Zinger et al. |
| 6,571,837 | B2 | 6/2003 | Jansen et al. |
| 6,572,591 | B2 | 6/2003 | Mayer |
| 6,575,955 | B2 | 6/2003 | Azzolini |
| 6,581,593 | B1 | 6/2003 | Rubin et al. |
| 6,582,415 | B1 | 6/2003 | Fowles et al. |
| D476,731 | S | 7/2003 | Cise et al. |
| 6,591,876 | B2 | 7/2003 | Safabash |
| 6,599,273 | B1 | 7/2003 | Lopez |
| 6,601,721 | B2 | 8/2003 | Jansen et al. |
| 6,626,309 | B1 | 9/2003 | Jansen et al. |
| 6,638,244 | B1 | 10/2003 | Reynolds |
| D482,121 | S | 11/2003 | Harding et al. |
| D482,447 | S | 11/2003 | Harding et al. |
| 6,651,956 | B2 | 11/2003 | Miller |
| 6,652,509 | B1 | 11/2003 | Helgren et al. |
| D483,487 | S | 12/2003 | Harding et al. |
| D483,869 | S | 12/2003 | Tran et al. |
| 6,656,433 | B2 | 12/2003 | Sasso |
| 6,666,852 | B2 | 12/2003 | Niedospial, Jr. |
| 6,681,810 | B2 | 1/2004 | Weston |
| 6,681,946 | B1 | 1/2004 | Jansen et al. |
| 6,682,509 | B2 | 1/2004 | Lopez |
| 6,692,478 | B1 | 2/2004 | Paradis |
| 6,692,829 | B2 | 2/2004 | Stubler et al. |
| 6,695,829 | B2 | 2/2004 | Hellstrom et al. |
| 6,699,229 | B2 | 3/2004 | Zinger et al. |
| 6,706,022 | B1 | 3/2004 | Leinsing et al. |
| 6,706,031 | B2 | 3/2004 | Manera |
| 6,715,520 | B2 | 4/2004 | Andreasson et al. |
| 6,729,370 | B2 | 5/2004 | Norton et al. |
| 6,736,798 | B2 | 5/2004 | Ohkubo et al. |
| 6,745,998 | B2 | 6/2004 | Doyle |
| 6,746,438 | B1 | 6/2004 | Arnissolle |
| 6,752,180 | B2 | 6/2004 | Delay |
| D495,416 | S | 8/2004 | Dimeo et al. |
| D496,457 | S | 9/2004 | Prais et al. |
| 6,802,490 | B2 | 10/2004 | Leinsing et al. |
| 6,832,994 | B2 | 12/2004 | Niedospial, Jr. et al. |
| 6,852,103 | B2 | 2/2005 | Fowles et al. |
| 6,875,203 | B1 | 4/2005 | Fowles et al. |
| 6,875,205 | B2 | 4/2005 | Leinsing |
| 6,878,131 | B2 | 4/2005 | Novacek et al. |
| 6,890,328 | B2 | 5/2005 | Fowles et al. |
| D506,256 | S | 6/2005 | Miyoshi et al. |
| 6,901,975 | B2 | 6/2005 | Aramata et al. |
| 6,945,417 | B2 | 9/2005 | Jansen et al. |
| 6,948,522 | B2 | 9/2005 | Newbrough et al. |
| 6,949,086 | B2 | 9/2005 | Ferguson et al. |
| 6,951,613 | B2 | 10/2005 | Reif et al. |
| 6,957,745 | B2 | 10/2005 | Thibault et al. |
| RE38,996 | E | 2/2006 | Crawford et al. |
| 6,994,315 | B2 | 2/2006 | Ryan et al. |
| 6,997,916 | B2 | 2/2006 | Simas, Jr. et al. |
| 6,997,917 | B2 | 2/2006 | Niedospial, Jr. et al. |
| 7,024,968 | B2 | 4/2006 | Raudabough et al. |
| 7,070,589 | B2 | 7/2006 | Lolachi et al. |
| 7,074,216 | B2 | 7/2006 | Fowles et al. |
| 7,083,600 | B2 | 8/2006 | Meloul |
| 7,086,431 | B2 | 8/2006 | D'Antonio et al. |
| 7,100,890 | B2 | 9/2006 | Cote, Sr. et al. |
| 7,140,401 | B2 | 11/2006 | Wilcox et al. |
| 7,150,735 | B2 | 12/2006 | Hickle |
| 7,192,423 | B2 | 3/2007 | Wong |
| 7,195,623 | B2 | 3/2007 | Burroughs et al. |
| 7,241,285 | B1 | 7/2007 | Dikeman |
| 7,294,122 | B2 | 11/2007 | Kubo et al. |
| 7,306,199 | B2 | 12/2007 | Leinsing et al. |
| D561,348 | S | 2/2008 | Zinger et al. |
| 7,326,188 | B1 | 2/2008 | Russell et al. |
| 7,326,194 | B2 | 2/2008 | Zinger et al. |
| 7,350,764 | B2 | 4/2008 | Raybuck |
| 7,354,422 | B2 | 4/2008 | Riesenberger et al. |
| 7,354,427 | B2 | 4/2008 | Fangrow |
| 7,425,209 | B2 | 9/2008 | Fowles et al. |
| 7,435,246 | B2 | 10/2008 | Zihlmann |
| D580,558 | S | 11/2008 | Shigesada et al. |
| 7,452,348 | B2 | 11/2008 | Hasegawa |
| 7,470,257 | B2 | 12/2008 | Norton et al. |
| 7,470,265 | B2 | 12/2008 | Brugger et al. |
| 7,472,932 | B2 | 1/2009 | Weber et al. |
| 7,488,297 | B2 | 2/2009 | Flaherty |
| 7,491,197 | B2 | 2/2009 | Jansen et al. |
| 7,497,848 | B2 | 3/2009 | Leinsing et al. |
| 7,523,967 | B2 | 4/2009 | Steppe |
| 7,530,546 | B2 | 5/2009 | Ryan et al. |
| D595,420 | S | 6/2009 | Suzuki et al. |
| D595,421 | S | 6/2009 | Suzuki et al. |
| 7,540,863 | B2 | 6/2009 | Haindl |
| 7,540,865 | B2 | 6/2009 | Griffin et al. |
| 7,544,191 | B2 | 6/2009 | Peluso et al. |
| D595,862 | S | 7/2009 | Suzuki et al. |
| D595,863 | S | 7/2009 | Suzuki et al. |
| 7,611,487 | B2 | 11/2009 | Woehr et al. |
| 7,611,502 | B2 | 11/2009 | Daly |
| 7,615,041 | B2 | 11/2009 | Sullivan et al. |
| 7,628,779 | B2 | 12/2009 | Aneas |
| 7,632,261 | B2 | 12/2009 | Zinger et al. |
| D608,900 | S | 1/2010 | Giraud et al. |
| 7,654,995 | B2 | 2/2010 | Warren et al. |
| 7,670,326 | B2 | 3/2010 | Shemesh |
| 7,695,445 | B2 | 4/2010 | Yuki |

(56) References Cited

U.S. PATENT DOCUMENTS

| | | | |
|---|---|---|---|
| D616,090 | S | 5/2010 | Kawamura |
| 7,713,247 | B2 | 5/2010 | Lopez |
| 7,717,886 | B2 | 5/2010 | Lopez |
| 7,722,090 | B2 | 5/2010 | Burton et al. |
| D616,984 | S | 6/2010 | Gilboa |
| 7,731,678 | B2 | 6/2010 | Tennican et al. |
| 7,743,799 | B2 | 6/2010 | Mosler et al. |
| 7,744,581 | B2 | 6/2010 | Wallen et al. |
| 7,757,901 | B2 | 7/2010 | Welp |
| 7,758,082 | B2 | 7/2010 | Weigel et al. |
| 7,762,524 | B2 | 7/2010 | Cawthon et al. |
| 7,766,304 | B2 | 8/2010 | Phillips |
| 7,771,383 | B2 | 8/2010 | Truitt et al. |
| D624,641 | S | 9/2010 | Boclet |
| 7,799,009 | B2 | 9/2010 | Niedospial, Jr. et al. |
| 7,803,140 | B2 | 9/2010 | Fangrow, Jr. |
| D627,216 | S | 11/2010 | Fulginiti |
| D630,732 | S | 1/2011 | Lev et al. |
| 7,862,537 | B2 | 1/2011 | Zinger et al. |
| 7,867,215 | B2 | 1/2011 | Akerlund et al. |
| 7,879,018 | B2 | 2/2011 | Zinger et al. |
| D634,007 | S | 3/2011 | Zinger et al. |
| 7,900,659 | B2 | 3/2011 | Whitley et al. |
| D637,713 | S | 5/2011 | Nord et al. |
| D641,080 | S | 7/2011 | Zinger et al. |
| 7,985,216 | B2 | 7/2011 | Daily et al. |
| D644,104 | S | 8/2011 | Maeda et al. |
| 7,993,328 | B2 | 8/2011 | Whitley |
| 8,007,461 | B2 | 8/2011 | Huo et al. |
| 8,012,132 | B2 | 9/2011 | Lum et al. |
| 8,016,809 | B2 | 9/2011 | Zinger et al. |
| 8,021,325 | B2 | 9/2011 | Zinger et al. |
| 8,025,653 | B2 | 9/2011 | Capitaine et al. |
| 8,029,472 | B2 | 10/2011 | Leinsing et al. |
| 8,038,123 | B2 | 10/2011 | Ruschke et al. |
| 8,066,688 | B2 | 11/2011 | Zinger et al. |
| 8,070,739 | B2 | 12/2011 | Zinger et al. |
| 8,075,550 | B2 | 12/2011 | Nord et al. |
| 8,096,525 | B2 | 1/2012 | Ryan |
| 8,105,314 | B2 | 1/2012 | Fangrow, Jr. |
| D654,166 | S | 2/2012 | Lair |
| D655,017 | S | 2/2012 | Mosler et al. |
| 8,122,923 | B2 | 2/2012 | Kraus et al. |
| 8,123,736 | B2 | 2/2012 | Kraushaar et al. |
| 8,157,784 | B2 | 4/2012 | Rogers |
| 8,167,863 | B2 | 5/2012 | Yow |
| 8,172,824 | B2 | 5/2012 | Pfeifer et al. |
| 8,177,768 | B2 | 5/2012 | Leinsing |
| 8,182,452 | B2 | 5/2012 | Mansour et al. |
| 8,187,248 | B2 | 5/2012 | Zihlmann |
| 8,196,614 | B2 | 6/2012 | Kriheli |
| 8,197,459 | B2 | 6/2012 | Jansen et al. |
| 8,211,069 | B2 | 7/2012 | Fangrow, Jr. |
| 8,225,959 | B2 | 7/2012 | Lambrecht |
| 8,241,268 | B2 | 8/2012 | Whitley |
| 8,262,628 | B2 | 9/2012 | Fangrow, Jr. |
| 8,262,641 | B2 | 9/2012 | Vedrine et al. |
| 8,267,127 | B2 | 9/2012 | Kriheli |
| D669,980 | S | 10/2012 | Lev et al. |
| 8,287,513 | B2 | 10/2012 | Ellstrom et al. |
| D673,673 | S | 1/2013 | Wang |
| D674,088 | S | 1/2013 | Lev et al. |
| D681,230 | S | 4/2013 | Mosler et al. |
| 8,454,573 | B2 | 6/2013 | Wyatt et al. |
| 8,469,939 | B2 | 6/2013 | Fangrow, Jr. |
| 8,475,404 | B2 | 7/2013 | Foshee et al. |
| 8,480,645 | B1 | 7/2013 | Choudhury et al. |
| 8,480,646 | B2 | 7/2013 | Nord et al. |
| 8,506,548 | B2 | 8/2013 | Okiyama |
| 8,511,352 | B2 | 8/2013 | Kraus et al. |
| 8,512,309 | B2 | 8/2013 | Shemesh et al. |
| D690,418 | S | 9/2013 | Rosenquist |
| 8,523,837 | B2 | 9/2013 | Wiggins et al. |
| 8,545,476 | B2 | 10/2013 | Ariagno et al. |
| 8,551,067 | B2 | 10/2013 | Zinger et al. |
| 8,556,879 | B2 | 10/2013 | Okiyama |
| 8,562,582 | B2 | 10/2013 | Tuckwell et al. |
| 8,608,723 | B2 | 12/2013 | Lev et al. |
| 8,628,508 | B2 | 1/2014 | Weitzel et al. |
| 8,684,992 | B2 | 4/2014 | Sullivan et al. |
| 8,684,994 | B2 | 4/2014 | Lev et al. |
| 8,752,598 | B2 | 6/2014 | Denenburg et al. |
| D717,406 | S | 11/2014 | Stanley et al. |
| D720,451 | S | 12/2014 | Denenburg et al. |
| 8,900,212 | B2 | 12/2014 | Kubo |
| D720,850 | S | 1/2015 | Hsia et al. |
| 2001/0000347 | A1 | 4/2001 | Hellstrom et al. |
| 2001/0025671 | A1 | 10/2001 | Safabash |
| 2001/0029360 | A1 | 10/2001 | Miyoshi et al. |
| 2001/0051793 | A1 | 12/2001 | Weston |
| 2002/0017328 | A1 | 2/2002 | Loo |
| 2002/0066715 | A1 | 6/2002 | Niedospial |
| 2002/0087118 | A1 | 7/2002 | Reynolds et al. |
| 2002/0087141 | A1 | 7/2002 | Zinger et al. |
| 2002/0087144 | A1 | 7/2002 | Zinger et al. |
| 2002/0121496 | A1 | 9/2002 | Thiebault et al. |
| 2002/0123736 | A1 | 9/2002 | Fowles et al. |
| 2002/0127150 | A1 | 9/2002 | Sasso |
| 2002/0128628 | A1 | 9/2002 | Fathallah |
| 2002/0138045 | A1 | 9/2002 | Moen |
| 2002/0173752 | A1 | 11/2002 | Polzin |
| 2002/0193777 | A1 | 12/2002 | Aneas |
| 2003/0028156 | A1 | 2/2003 | Juliar |
| 2003/0036725 | A1 | 2/2003 | Lavi et al. |
| 2003/0068354 | A1 | 4/2003 | Reif et al. |
| 2003/0073971 | A1 | 4/2003 | Saker |
| 2003/0100866 | A1 | 5/2003 | Reynolds |
| 2003/0109846 | A1 | 6/2003 | Zinger et al. |
| 2003/0120209 | A1 | 6/2003 | Jensen et al. |
| 2003/0153895 | A1 | 8/2003 | Leinsing |
| 2003/0187420 | A1 | 10/2003 | Akerlund et al. |
| 2003/0191445 | A1 | 10/2003 | Wallen et al. |
| 2003/0195479 | A1 | 10/2003 | Kuracina et al. |
| 2003/0199846 | A1 | 10/2003 | Fowles et al. |
| 2003/0199847 | A1 | 10/2003 | Akerlund et al. |
| 2004/0024354 | A1 | 2/2004 | Reynolds |
| 2004/0039365 | A1 | 2/2004 | Aramata et al. |
| 2004/0044327 | A1 | 3/2004 | Hasegawa |
| 2004/0073189 | A1 | 4/2004 | Wyatt et al. |
| 2004/0143226 | A1 | 7/2004 | Marsden |
| 2004/0153047 | A1 | 8/2004 | Blank et al. |
| 2004/0181192 | A1 | 9/2004 | Cuppy |
| 2004/0204699 | A1 | 10/2004 | Hanly et al. |
| 2004/0217315 | A1 | 11/2004 | Doyle |
| 2004/0225274 | A1 | 11/2004 | Jansen et al. |
| 2004/0236305 | A1 | 11/2004 | Jansen et al. |
| 2004/0255952 | A1 | 12/2004 | Carlsen et al. |
| 2005/0015070 | A1 | 1/2005 | Delnevo et al. |
| 2005/0016626 | A1 | 1/2005 | Wilcox et al. |
| 2005/0055008 | A1 | 3/2005 | Paradis et al. |
| 2005/0082828 | A1 | 4/2005 | Wicks et al. |
| 2005/0124964 | A1 | 6/2005 | Niedospial et al. |
| 2005/0137566 | A1 | 6/2005 | Fowles et al. |
| 2005/0148994 | A1 | 7/2005 | Leinsing |
| 2005/0159724 | A1 | 7/2005 | Enerson |
| 2005/0182383 | A1 | 8/2005 | Wallen |
| 2005/0209554 | A1 | 9/2005 | Landau |
| 2005/0261637 | A1 | 11/2005 | Miller |
| 2005/0277896 | A1 | 12/2005 | Messerli et al. |
| 2006/0030832 | A1 | 2/2006 | Niedospial et al. |
| 2006/0079834 | A1 | 4/2006 | Tennican et al. |
| 2006/0089594 | A1 | 4/2006 | Landau |
| 2006/0089603 | A1 | 4/2006 | Truitt et al. |
| 2006/0095015 | A1 | 5/2006 | Hobbs et al. |
| 2006/0106360 | A1 | 5/2006 | Wong |
| 2006/0135948 | A1 | 6/2006 | Varma |
| 2006/0155257 | A1 | 7/2006 | Reynolds |
| 2006/0253084 | A1 | 11/2006 | Nordgren |
| 2007/0024995 | A1 | 2/2007 | Hayashi |
| 2007/0060904 | A1 | 3/2007 | Vedrine et al. |
| 2007/0079894 | A1 | 4/2007 | Kraus et al. |
| 2007/0083164 | A1 | 4/2007 | Barrelle et al. |
| 2007/0088252 | A1 | 4/2007 | Pestotnik et al. |
| 2007/0088293 | A1 | 4/2007 | Fangrow |

(56) References Cited

U.S. PATENT DOCUMENTS

2007/0088313 A1 4/2007 Zinger et al.
2007/0106244 A1 5/2007 Mosler et al.
2007/0112324 A1 5/2007 Hamedi-Sangsari
2007/0156112 A1 7/2007 Walsh
2007/0167904 A1 7/2007 Zinger et al.
2007/0191760 A1 8/2007 Iguchi et al.
2007/0191764 A1 8/2007 Zihlmann
2007/0191767 A1 8/2007 Hennessy et al.
2007/0203451 A1 8/2007 Murakami et al.
2007/0219483 A1 9/2007 Kitani et al.
2007/0244447 A1 10/2007 Capitaine et al.
2007/0244461 A1 10/2007 Fangrow
2007/0244462 A1 10/2007 Fangrow
2007/0244463 A1 10/2007 Warren et al.
2007/0249995 A1 10/2007 Van Manen
2007/0255202 A1 11/2007 Kitani et al.
2007/0265574 A1 11/2007 Tennican et al.
2007/0265581 A1 11/2007 Funamura et al.
2007/0270778 A9 11/2007 Zinger et al.
2007/0287953 A1 12/2007 Ziv et al.
2007/0299404 A1 12/2007 Katoh et al.
2008/0009789 A1 1/2008 Zinger et al.
2008/0009822 A1 1/2008 Enerson
2008/0135051 A1 6/2008 Lee
2008/0172024 A1 7/2008 Yow
2008/0188799 A1 8/2008 Mueller-Beckhaus et al.
2008/0249479 A1 10/2008 Zinger et al.
2008/0249498 A1 10/2008 Fangrow
2008/0262465 A1 10/2008 Zinger et al.
2008/0287905 A1 11/2008 Hiejima et al.
2008/0294100 A1 11/2008 de Costa et al.
2008/0306439 A1 12/2008 Nelson et al.
2008/0312634 A1 12/2008 Helmerson et al.
2009/0012492 A1 1/2009 Zihlmann
2009/0082750 A1 3/2009 Denenburg et al.
2009/0143758 A1 6/2009 Okiyama
2009/0177177 A1 7/2009 Zinger et al.
2009/0177178 A1 7/2009 Pedersen
2009/0187140 A1 7/2009 Racz
2009/0216212 A1 8/2009 Fangrow, Jr.
2009/0267011 A1 10/2009 Hatton et al.
2009/0299325 A1 12/2009 Vedrine et al.
2009/0326506 A1 12/2009 Hasegawa et al.
2010/0010443 A1 1/2010 Morgan et al.
2010/0022985 A1 1/2010 Sullivan et al.
2010/0030181 A1 2/2010 Helle et al.
2010/0036319 A1 2/2010 Drake et al.
2010/0076397 A1 3/2010 Reed et al.
2010/0087786 A1 4/2010 Zinger et al.
2010/0137827 A1 6/2010 Warren et al.
2010/0160889 A1 6/2010 Smith et al.
2010/0168664 A1 7/2010 Zinger et al.
2010/0168712 A1 7/2010 Tuckwell et al.
2010/0179506 A1 7/2010 Shemesh et al.
2010/0198148 A1 8/2010 Zinger et al.
2010/0204670 A1 8/2010 Kraushaar et al.
2010/0241088 A1 9/2010 Ranalletta et al.
2010/0274184 A1 10/2010 Chun
2010/0286661 A1 11/2010 Raday et al.
2010/0312220 A1 12/2010 Kalitzki
2011/0004184 A1 1/2011 Proksch et al.
2011/0054440 A1 3/2011 Lewis
2011/0087164 A1 4/2011 Mosler et al.
2011/0160701 A1 6/2011 Wyatt et al.
2011/0175347 A1 7/2011 Okiyama
2011/0218511 A1 9/2011 Yokoyama
2011/0224640 A1 9/2011 Kuhn et al.
2011/0230856 A1 9/2011 Kyle et al.
2011/0264037 A1 10/2011 Foshee et al.
2011/0264069 A1 10/2011 Bochenko
2011/0276007 A1 11/2011 Denenburg
2011/0319827 A1 12/2011 Leinsing et al.
2012/0022469 A1 1/2012 Alpert
2012/0053555 A1* 3/2012 Ariagno ................ A61J 1/2089 604/413
2012/0059346 A1 3/2012 Sheppard et al.
2012/0067429 A1 3/2012 Mosler et al.
2012/0078214 A1 3/2012 Finke et al.
2012/0123382 A1* 5/2012 Kubo .................... A61J 1/2096 604/413
2012/0184938 A1 7/2012 Lev et al.
2012/0215182 A1 8/2012 Mansour et al.
2012/0220977 A1 8/2012 Yow
2012/0220978 A1 8/2012 Lev et al.
2012/0265163 A1 10/2012 Cheng et al.
2012/0271229 A1 10/2012 Lev et al.
2012/0296307 A1 11/2012 Holt et al.
2012/0310203 A1 12/2012 Khaled et al.
2012/0323187 A1 12/2012 Iwase et al.
2012/0323210 A1 12/2012 Lev et al.
2013/0046269 A1 2/2013 Lev et al.
2013/0053814 A1 2/2013 Mueller-Beckhaus et al.
2013/0096493 A1 4/2013 Kubo et al.
2013/0144248 A1 6/2013 Putter et al.
2013/0199669 A1 8/2013 Moy et al.
2013/0226100 A1 8/2013 Lev
2013/0231630 A1 9/2013 Kraus et al.
2013/0237904 A1 9/2013 Deneburg et al.
2013/0289530 A1 10/2013 Wyatt et al.
2014/0020793 A1 1/2014 Denenburg et al.
2014/0096862 A1 4/2014 Aneas
2014/0150911 A1 6/2014 Hanner et al.
2014/0352845 A1 12/2014 Lev et al.
2015/0082746 A1 3/2015 Ivosevic et al.
2015/0088078 A1 3/2015 Lev et al.

FOREIGN PATENT DOCUMENTS

DE 4122476 A1 1/1993
DE 19504413 A1 8/1996
DE 202004012714 U1 11/2004
DE 202009011019 U1 12/2010
EP 0192661 A1 9/1986
EP 0195018 A1 9/1986
EP 0258913 A2 3/1988
EP 0416454 A2 3/1991
EP 0518397 A1 12/1992
EP 0521460 A1 1/1993
EP 0637443 A1 2/1995
EP 0737467 A1 10/1996
EP 761562 A1 3/1997
EP 765652 A1 4/1997
EP 765853 A1 4/1997
EP 0806597 A1 11/1997
EP 0814866 A1 1/1998
EP 829248 A2 3/1998
EP 0856331 A2 8/1998
EP 882441 A2 12/1998
EP 0887085 A2 12/1998
EP 897708 A2 2/1999
EP 0898951 A2 3/1999
EP 960616 A2 12/1999
EP 1008337 A1 6/2000
EP 1029526 A1 8/2000
EP 1034809 A1 9/2000
EP 1051988 A2 11/2000
EP 1323403 A1 7/2003
EP 1329210 A1 7/2003
EP 1396250 A1 3/2004
EP 1454609 A1 9/2004
EP 1454650 A1 9/2004
EP 1498097 A2 1/2005
EP 1872824 A1 1/2008
EP 1911432 A1 4/2008
EP 1919432 A1 5/2008
EP 1930038 A2 6/2008
EP 2090278 A1 8/2009
EP 2351548 A1 8/2011
EP 2351549 A1 8/2011
EP 2462913 A1 6/2012
FR 2029242 A5 10/1970
FR 2856660 A1 12/2004
FR 2869795 A1 11/2005
FR 2931363 A1 11/2009

(56) References Cited

FOREIGN PATENT DOCUMENTS

| | | | |
|---|---|---|---|
| GB | 1444210 | A | 7/1976 |
| IL | 171662 | | 10/2005 |
| JP | 03-062426 | B | 9/1991 |
| JP | 4329954 | A | 11/1992 |
| JP | 06-050656 | U | 7/1994 |
| JP | H08-000710 | A | 1/1996 |
| JP | 09-104460 | A | 4/1997 |
| JP | 09-104461 | A | 4/1997 |
| JP | 10-118158 | A | 5/1998 |
| JP | H10-504736 | A | 5/1998 |
| JP | 11503627 | T | 3/1999 |
| JP | 11-319031 | A | 11/1999 |
| JP | 2000-508934 | A | 7/2000 |
| JP | 2000-237278 | A | 9/2000 |
| JP | 2001-505083 | A | 4/2001 |
| JP | 2002-035140 | A | 2/2002 |
| JP | 2002-516160 | A | 6/2002 |
| JP | 2002-355318 | A | 12/2002 |
| JP | 2003-033441 | A | 2/2003 |
| JP | 2003-102807 | A | 4/2003 |
| JP | 2004-097253 | A | 4/2004 |
| JP | 2004-522541 | A | 7/2004 |
| JP | 2010-179128 | A | 8/2010 |
| WO | 8601712 | A1 | 3/1986 |
| WO | 9003536 | A1 | 4/1990 |
| WO | 9403373 | A1 | 2/1994 |
| WO | 9507066 | A1 | 3/1995 |
| WO | 9600053 | A1 | 1/1996 |
| WO | 9629113 | A1 | 9/1996 |
| WO | 9736636 | A1 | 10/1997 |
| WO | 9832411 | A1 | 7/1998 |
| WO | 9837854 | A1 | 9/1998 |
| WO | 9961093 | A1 | 12/1999 |
| WO | 0128490 | A1 | 4/2001 |
| WO | 0130425 | A1 | 5/2001 |
| WO | 0132524 | A1 | 5/2001 |
| WO | 0160311 | A1 | 8/2001 |
| WO | 0191693 | A2 | 12/2001 |
| WO | 0209797 | A1 | 2/2002 |
| WO | 0232372 | A1 | 4/2002 |
| WO | 0236191 | A2 | 5/2002 |
| WO | 02066100 | A2 | 8/2002 |
| WO | 02089900 | A1 | 11/2002 |
| WO | 03051423 | A2 | 6/2003 |
| WO | 03070147 | A2 | 8/2003 |
| WO | 03079956 | A1 | 10/2003 |
| WO | 2004041148 | A1 | 5/2004 |
| WO | 2005002492 | A1 | 1/2005 |
| WO | 2005041846 | A2 | 5/2005 |
| WO | 2005105014 | A2 | 11/2005 |
| WO | 2006099441 | A2 | 9/2006 |
| WO | 2007015233 | A1 | 2/2007 |
| WO | 2007017868 | A1 | 2/2007 |
| WO | 2007052252 | A1 | 5/2007 |
| WO | 2007101772 | A1 | 9/2007 |
| WO | 2007105221 | A1 | 9/2007 |
| WO | 2008081424 | A2 | 7/2008 |
| WO | 2008126090 | A1 | 10/2008 |
| WO | 2009026443 | A2 | 2/2009 |
| WO | 2009029010 | A1 | 3/2009 |
| WO | 2009038860 | A2 | 3/2009 |
| WO | 2009040804 | A2 | 4/2009 |
| WO | 2009087572 | A1 | 7/2009 |
| WO | 2009093249 | A1 | 7/2009 |
| WO | 2009112489 | A1 | 9/2009 |
| WO | 2009146088 | A1 | 12/2009 |
| WO | 2010061743 | A1 | 6/2010 |
| WO | 2010117580 | A1 | 10/2010 |
| WO | 2011039747 | A1 | 4/2011 |
| WO | 2011058545 | A1 | 5/2011 |
| WO | 2011058548 | A1 | 5/2011 |
| WO | 2011077434 | A1 | 6/2011 |
| WO | 2011104711 | A1 | 9/2011 |
| WO | 2012063230 | A1 | 5/2012 |
| WO | 2012143921 | A1 | 10/2012 |
| WO | 2013127813 | A1 | 9/2013 |
| WO | 2013134246 | A1 | 9/2013 |
| WO | 2013156944 | A1 | 10/2013 |
| WO | 2014033706 | A2 | 3/2014 |
| WO | 2014033710 | A1 | 3/2014 |

OTHER PUBLICATIONS

Novel Transfer, Mixing and Drug Delivery Systems, MOP Medimop Medical Projects Ltd. Catalog, 4 pages, Rev. 4, 2004.
Office Action dated Oct. 6, 2003 in U.S. Appl. No. 10/062,796.
Office Action dated Feb. 22, 2005 in U.S. Appl. No. 10/062,796.
Office Action dated Oct. 5, 2005 in U.S. Appl. No. 10/062,796.
Office Action dated Feb. 20, 2009 in U.S. Appl. No. 11/694,297.
Int'l Search Report dated Dec. 6, 2006 in Int'l Application No. PCT/IL2006/000912.
Int'l Preliminary Report on Patentability dated Dec. 4, 2007 in Int'l Application No. PCT/IL2006/000912.
http://www.westpharma.com/en/products/Pages/Mixject.aspx (admitted prior art).
http://www.westpharma.com/SiteCollectionDocuments/Recon/mixject%20product%20sheet.pdf; MIXJECT product information sheet pp. 1. (admitted prior art).
Int'l Search Report dated Jul. 27, 2007 in Int'l Application No. PCT/IL2007/000343.
Int'l Preliminary Report on Patentability dated Jun. 19, 2008 in Int'l Application No. PCT/IL2007/000343.
Int'l Search Report dated Mar. 27, 2009 in Int'l Application No. PCT/US2008/070024.
Int'l Search Report dated Oct. 17, 2005 in Int'l Application No. PCT/IL2005/000376.
Int'l Preliminary Report on Patentability dated Jun. 19, 2006 in Int'l Application No. PCT/IL2005/000376.
Written Opinion of ISR dated Jun. 19, 2006 in Int'l Application No. PCT/IL2005/000376.
Int'l Search Report dated Aug. 25, 2008 in Int'l Application No. PCT/IL2008/000517.
Written Opinion of the ISR dated Oct. 17, 2009 in Int'l Application No. PCT/IL08/00517.
Int'l Preliminary Report on Patenability dated Oct. 20, 2009 in Int'l Application No. PCT/IL2008/000517.
Written Opinion of the Int'l Searching Authority dated Oct. 27, 2008 in Int'l Application No. PCT/US2008/070024.
Int'l Search Report dated Mar. 12, 2009 in Int'l Application No. PCT/IL2008/001278.
Office Action dated Jan. 20, 2010 in JP Application No. 2007-510229.
Office Action dated Apr. 20, 2010 in U.S. Appl. No. 11/997,569.
Int'l Search Report dated Nov. 20, 2006 in Int'l Application No. PCT/IL2006/000881.
Office Action dated May 27, 2010 in U.S. Appl. No. 11/559,152.
Decision to Grant dated Apr. 12, 2010 in EP Application No. 08738307.1.
Office Action dated Jun. 1, 2010 in U.S. Appl. No. 11/568,421.
Office Action dated Nov. 12, 2010 in U.S. Appl. No. 29/334,697.
The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justrice.gov.il/UI/RequestsList.aspx>. (1 page).
Int'l Search Report dated Nov. 25, 2010 in Int'l Application No. PCT/IL2010/000530.
Office Action dated Feb. 7, 2011 in U.S. Appl. No. 12/783,194.
Office Action dated Dec. 20, 2010 in U.S. Appl. No. 12/063,176.
Office Action dated Dec. 13, 2010 in U.S. Appl. No. 12/293,122.
Office Action dated Nov. 29, 2010 in U.S. Appl. No. 11/568,421.
Office Action dated Dec. 23, 2010 in U.S. Appl. No. 29/334,696.
Int'l Search Report dated Mar. 17, 2011 in Int'l Application No. PCT/IL2010/000854.

(56) References Cited

OTHER PUBLICATIONS

Overview—Silicone Rubber [retrieved from http://www.knovel.com/web/portal/browse/display?_EXT_KNOVEL_DISPLAY_bookid=1023&VerticalID=0 on Feb. 9. 2011].
Int'l Search Report dated Mar. 17, 2011 in Int'l Application No. PCT/IL2010/00915.
Office Action dated May 12, 2011 in U.S. Appl. No. 12/063,176.
Office Action dated Jul. 11, 2011 in U.S. Appl. No. 12/293,122.
Int'l Search Report dated Jul. 12, 2011 in Int'l Application No. PCT/IL2011/000187.
Int'l Search Report dated Jul. 12, 2011 in Int'l Application No. PCT/IL2011/000186.
Office Action dated Aug. 3, 2011 in JP Application No. 2008-525719.
Int'l Search Report dated Oct. 7, 2011 in Int'l Application No. PCT/IL2011/000511.
Int'l Search Report dated Mar. 6, 2012 in Int'l Application No. PCT/IL2011/000834; Written Opinion.
Office Action dated Mar. 1, 2012 in JP Application No. 2007-510229.
Int'l Search Report dated Mar. 7, 2012 in Int'l Application No. PCT/IL2011/000829; Written Opinion.
Office Action dated Mar. 13, 2012 in CA Application No. 2,563,643.
Office Action issued Mar. 1, 2012 in CN Application No. 2008801108283.4.
Written Opinion dated Apr. 10, 2015 in Int'l Application No. PCT/IL2014/050405.
Response to Written Opinion dated Mar. 9, 2015 in Int'l Application No. PCT/IL2014/050405.
Int'l Preliminary Report on Patentability dated Aug. 24, 2015 in Int'l Application No. PCT/IL2014/050405.
U.S. Appl. No. 14/888,590 by Marks, filed Nov. 2, 2015.
U.S. Appl. No. 14/784,300 by Lev, filed Oct. 14, 2015.
Office Action dated Oct. 5, 2015 in U.S. Appl. No. 14/385,212 by Lev.
U.S. Appl. No. 29/544,969 by Ben Shalom, filed Nov. 9, 2015.
Office Action dated Aug. 24, 2015 in U.S. Appl. No. 14/366,306 by Lev.
Office Action dated Mar. 10, 2015 in EP Application No. 12 812 395.7.
Office Action dated Aug. 7, 2015 in JP Application No. 2015-529206.
Office Action dated Jan. 2, 2015 in U.S. Appl. No. 29/438,141 by Gilboa.
Office Action dated Jan. 5, 2015 in U.S. Appl. No. 29/413,220 by Lev.
Office Action dated Jan. 7, 2015 in U.S. Appl. No. 29/438,134 by Lev.
U.S. Appl. No. 14/423,595 by Lev, filed Feb. 24, 2015.
U.S. Appl. No. 14/425,582 by Lev, filed Mar. 3, 2015.
Office Action dated Nov. 11, 2013 in IL Application No. 218730.
U.S. Appl. No. 29/478,723 by Lev, filed Jan. 8, 2014.
U.S. Appl. No. 29/478,726 by Lev, filed Jan. 8, 2014.
Office Action dated Jan. 2, 2014 in U.S. Appl. No. 13/505,881 by Lev.
Int'l Preliminary Report on Patentability dated Sep. 24, 2013 in Int'l Application No. PCT/IL2012/000354.
Office Action dated Feb. 13, 2014 in U.S. Appl. No. 13/884,981 by Denenburg.
U.S. Appl. No. 14/345,094 by Lev, filed Mar. 14, 2014.
Int'l Search Report and Written Opinion dated Jan. 7, 2014 in Int'l Application No. PCT/IL2012/050721.
English translation of an Office Action dated Jan. 9, 2014 in JP Application No. 2010-526421.
English translation of an Office Action dated Dec. 4, 2013 in CN Application No. 201080051210.3.
English translation of an Office Action dated Dec. 25, 2013 in CN Application No. 201180006530.1.
Office Action dated Nov. 28, 2013 in IN Application No. 4348/DELNP/2008.
Office Action dated Oct. 8, 2013 in CN Application No. 201080043825.1.
English translation of an Office Action dated Feb. 4, 2014 in JP Application No. 2012-554468.
Office Action dated Jan. 17, 2014 in CN Application No. 201180006534.X.
Int'l Search Report and Written Opinion dated May 8, 2014 in Int'l Application No. PCT/IL2013/050706.
English translation of an Office Action dated Apr. 28, 2014 in JP Application No. 2013-537257.
Int'l Preliminary Report on Patentability dated Jan. 14, 2014 in Int'l Application No. PCT/IL2012/050516.
Office Action dated May 6, 2014 in U.S. Appl. No. 13/505,881 by Lev.
U.S. Appl. No. 14/366,306 by Lev, filed Jun. 18, 2014.
Office Action dated Apr. 17, 2014 in CN Application No. 201080051201.4.
Int'l Search Report and Written Opinion issued Jul. 16, 2014 in Int'l Application No. PCT/IL2014/050327.
English translation of an Office Action dated Jun. 30, 2014 in CN Application No. 201180052962.6.
Extended European Search Report dated Jun. 3, 2014 in EP Application No. 08781828.2.
Written Opinion dated Jul. 1, 2013 in Int'l Application No. PCT/IL2013/050180.
Int'l Preliminary Report on Patentability dated Apr. 1, 2014 in Int'l Application No. PCT/IL2013/050180.
Written Opinion dated Jul. 31, 2013 in Int'l Application No. PCT/IL2013/050313.
Int'l Preliminary Report on Patentability dated May 12, 2014 in Int'l Application No. PCT/IL2013/050316.
Office Action dated Jul. 31, 2014 in U.S. Appl. No. 29/438,141 by Gilboa.
U.S. Appl. No. 14/385,212 by Lev, filed Sep. 15, 2014.
U.S. Appl. No. 29/502,037 by Lev, filed Sep. 11, 2014.
U.S. Appl. No. 29/502,053 by Lev, filed Sep. 11, 2014.
U.S. Appl. No. 14/391,792 by Lev, filed Oct. 10, 2014.
U.S. Appl. No. 14/504,979 by Lev, filed Oct. 2, 2014.
Int'l Search Report and Written Opinion dated Sep. 2, 2014 in Int'l Application No. PCT/IL2014/050405.
Int'l Search Report and Written Opinion dated Oct. 17, 2014 in Int'l Application No. PCT/IL2014/050680.
English translation of an Office Action dated Aug. 28, 2014 in JP Application No. 2013-168885.
Office Action dated Dec. 9, 2015 in U.S. Appl. No. 29/478,723 by Lev.
West, Vial2Bag DC system, Oct. 2, 2014, https://web.archive.org/web/20141002065133/http://www.westpharma.com/en/products/Pages/Reconstitutionsystems.aspx.
Youtube.com, Vial2Bag DC, Aug. 21, 2014, https://www.youtube.com/watch?v=FEOkglxNBrs.
Office Action dated Dec. 9, 2015 in U.S. Appl. No. 29/478,726 by Lev.
Notice of Allowance dated Jan. 12, 2016 in U.S. Appl. No. 14/385,212 by Lev.
Office Action dated Mar. 17, 2015 in U.S. Appl. No. 14/504,979 by Lev.
Office Action dated Apr. 9, 2015 in U.S. Appl. No. 13/883,289 by Lev.
Office Action dated May 28, 2015 in U.S. Appl. No. 14/391,792 by Lev.
Office Action dated Mar. 6, 2012 in U.S. Appl. No. 12/678,928.
Int'l Search Report dated Feb. 3, 2011 in Int'l Application No. PCT/IL2010/000777; Written Opinion.
Int'l Search Report dated Mar. 17, 2011 in Int'l Application No. PCT/IL2010/000854; Written Opinion.
Int'l Search Report issued Mar. 17, 2011 in Int'l Application No. PCT/IL2010/000915; Written Opinion.
U.S. Appl. No. 13/505,790 by Lev, filed May 3, 2012.
U.S. Appl. No. 13/505,881 by Lev, filed May 3, 2012.
U.S. Appl. No. 13/522,410 by Lev, filed Jul. 16, 2012.
U.S. Appl. No. 13/576,461 by Lev, filed Aug. 1, 2012.
Office Action dated Jun. 14, 2012 in U.S. Appl. No. 29/376,980.

(56) References Cited

OTHER PUBLICATIONS

Office Action dated Jun. 15, 2012 in U.S. Appl. No. 29/413,170.
Office Action dated Jun. 21, 2012 in U.S. Appl. No. 12/596,167.
Alaris Medical Systems Product Brochure, 4 pages, Issue 1, Oct. 11, 1999.
Smart Site Needle-Free Systems, Alaris Medical Systems Webpage, 4 pages, Feb. 2006.
Photographs of Alaris Medical Systems SmartSite.RTM. device, 5 pages, 2002.
Non-Vented Vial Access Pin with ULTRASITE.RTM. Valve, B. Braun Medical, Inc. website and product description, 3 pages, Feb. 2006.
Int'l Search Report dated Aug. 16, 2012 in Int'l Application No. PCT/IL2012/000164.
U.S. Appl. No. 29/438,134 by Lev, filed Nov. 27, 2012.
U.S. Appl. No. 29/438,141 by Gilboa, filed Nov. 27, 2012.
Int'l Search Report dated Jan. 22, 2013 in Int'l Application No. PCT/IL2012/000354.
Int'l Search Report dated Mar. 18, 2013 in Int'l Application No. PCT/IL2012/050516.
Office Action dated Apr. 2, 2013 in U.S. Appl. No. 13/505,790.
Int'l Search Report and Written Opinion issued Mar. 6, 2012 in Int'l Application No. PCT/IL2011/000834.
U.S. Appl. No. 13/883,289 by Lev, filed May 3, 2013.
Int'l Search Report & Written Opinion dated Mar. 7, 2012 in Int'l Application No. PCT/IL2011/000829.
U.S. Appl. No. 13/884,981 by Denenburg, filed May 13, 2013.
Office Action dated May 31, 2013 in U.S. Appl. No. 13/505,790.
Int'l Search Report dated Jun. 5, 2013 in Int'l Application No. PCT/IL2012/050407.
Int'l Search Report dated Jun. 19, 2013 in Int'l Application No. PCT/IL2013/050167.
Int'l Search Report dated Jul. 1, 2013 in Int'l Application No. PCT/IL2013/050180.
Int'l Search Report dated Jul. 31, 2013 in Int'l Application No. PCT/IL2013/050313.
Int'l Search Report issued Jul. 26, 2013 in Int'l Application No. PCT/IL2013/050316.
English translation of an Office Action dated Jun. 19, 2013 in JP Application No. 2012-531551.
Office Action issued Aug. 20, 2013 in U.S. Appl. No. 13/576,461 by Lev.
Int'l Preliminary Report on Patentability issued Aug. 28, 2012 in Int'l Application No. PCT/IL2011/000186.
U.S. Appl No. 14/005,751 by Denenburg, filed Sep. 17, 2013.
English translation of an Office Action dated Jul. 26, 2013 in JP Application No. 2012-538464.
International Search Report dated Jan. 23, 2007 in Int'l Application No. PCT/IL/2006/001228.
IV disposables sets catalogue, Cardinal Health, Alaris® products, SmartSite® access devices and accessories product No. 10013365, SmartSite add-on bag access device with spike adapter and needle-free valve bag access port, pp. 1-5, Fall edition (2007).
Drug Administration Systems product information sheets; http://www.westpharma.com/eu/en/products/Pages/Vial2Bag.aspx;39 pp. 1-3 (admitted prior art).
Office Action dated Jun. 8, 2010 in U.S. Appl. No. 12/112,490 by Zinger.
Office Action dated Sep. 28, 2010 in U.S. Appl. No. 12/112,490 by Zinger.
Article with picture of West Pharmaceutical Services' Vial2Bag Needleless System, [on-line]; ISIPS Newsletter, Oct. 26, 2007]; retrieved from Internet Feb. 16, 2010]; URL:<http://www.isips.org/reports/ISIPS_Newsletter_October_26_2007. html.> (7 pages. see pp. 5-6).
Office Action dated Jun. 15, 2011 in JP Application No. 2008-538492.
Translation of Office Action dated Jun. 18, 2012 in JP Application No. 2008-538492.
Translation of Office Action dated Apr. 15, 2013 in JP Application No. 2008-538492.
Office Action dated Jul. 13, 2012 in U.S. Appl. No. 12/112,490 by Zinger.
Office Action dated Jan. 23, 2013 in U.S. Appl. No. 12/112,490 by Zinger.
Int'l Preliminary Report on Patentability dated May 6, 2008 in Int'l Application No. PCT/IL2006/001228.
Written Opinion dated Aug. 16, 2012 in Int'l Application No. PCT/IL2012/000164.
English translation of an Office Action dated Sep. 10, 2013 in JP Application No. 2012-554468.

* cited by examiner

LIQUID DRUG TRANSFER DEVICES EMPLOYING MANUAL ROTATION FOR DUAL FLOW COMMUNICATION STEP ACTUATIONS

CROSS-REFERENCE TO RELATED APPLICATION

This application is a Section 371 of International Application No. PCT/IL2013/050721, filed Aug. 26, 2013, which was published in the English language on Mar. 6, 2014, under International Publication No. WO 2014/033710 A1, which claims priority to U.S. Provisional Application No. 61/731,574 filed Nov. 30, 2012, and the disclosure of which is incorporated herein by reference.

FIELD OF THE INVENTION

The invention relates to liquid drug transfer devices for mixing, reconstitution and administration purposes.

BACKGROUND OF THE INVENTION

Commonly owned PCT International Application No. PCT/IL2012/000354 entitled Valve Assembly for Use with Liquid Container and Vial and published under PCT International Publication No. WO 2013/054323 discloses valve assemblies for use with an infusion liquid container and a drug vial. The valve assemblies include a conventional male drug vial adapter having a male connector in flow communication with a puncturing member for puncturing a drug vial stopper. The valve assemblies also include an access port adapter for attachment to an access port of an infusion liquid container and a female connector for sealingly mounting on the male connector. The use of the valve assemblies includes several user actions including inter alia attaching a valve assembly to an access port, telescopic clamping the valve assembly on a drug vial, and opening the valve assembly for enabling flow of infusion liquid to the drug vial for mixing or reconstitution purposes and subsequent transfer of liquid contents from the drug vial to the infusion liquid container for subsequent administration.

Commonly owned U.S. Pat. No. 6,558,365 to Zinger et al. entitled Fluid Transfer Device discloses liquid drug transfer devices for aseptic reconstitution of a drug medicament for administration purposes. The liquid drug transfer devices include a so-called female drug vial adapter and a so-called male liquid vial adapter pre-mounted on the female drug vial adapter. The female drug vial adapter is intended to be telescopically clamped on a drug vial containing a drug medicament typically under negative pressure. The male liquid vial adapter is intended to be telescopically clamped on a liquid vial containing diluent only or an active liquid component to be drawn into the drug vial by its negative pressure. The use of the liquid drug transfer devices involves several user actions including inter alia a user telescopically clamping the liquid vial adapter on a liquid vial, inverting the liquid drug transfer device together with the liquid vial, and telescopically clamping the drug vial adapter on a drug vial.

The aforesaid liquid drug transfer devices require several user actions which can be time consuming and prone to error, for example, inaccurate telescopic clamping a drug vial adapter on a drug vial can lead to the drug vial being unusable. There is a need for improved liquid drug transfer devices requiring less user actions for actuation purposes, thereby facilitating user convenience and reducing wastage of drug vials.

SUMMARY OF THE INVENTION

The present invention is directed toward liquid drug transfer devices employing manual rotation for dual flow communication step actuations for establishing flow communication between a liquid container containing liquid contents and an initially intact, namely, non-punctured, drug vial containing a drug medicament. The liquid container can be either an infusion liquid container or a liquid vial. Infusion liquid containers include inter alia a bottle, an IV bag, and the like. Liquid vials can contain diluent only or an active liquid component. Drug vials can include a powder drug medicament or a liquid drug medicament. Some drug vials are under negative pressure.

The liquid drug transfer devices have a longitudinal device axis and include a liquid container adapter for attachment to a liquid container, a dual ended liquid transfer member, and a drug vial adapter for telescopic clamping on a drug vial. The dual ended liquid transfer member has a trailing liquid transfer member end terminating in a puncturing tip co-directional with the longitudinal device axis and initially spaced apart from an uppermost drug vial surface of an initially intact drug vial. The liquid drug transfer devices are designed such that a manual rotation about a longitudinal device axis linearly compacts a liquid drug transfer device therealong for urging the puncturing tip along a linear displacement to puncture through a drug vial stopper during a drug vial flow communication step for flow communication with a drug vial interior.

Liquid drug transfer devices can be designed such that a drug vial flow communication step is a first flow communication step or a second flow communication step of a two flow communication step actuation depending on a clinical application at hand. Two flow communication step actuations including an initial drug vial flow communication step and a subsequent liquid container flow communication step afford the advantage that liquid contents can immediately flow from a liquid container to a drug vial. Two flow communication step actuations including an initial liquid container flow communication step and a subsequent drug vial flow communication step are mandatory in the case of a drug vial's negative pressure is employed for drawing liquid contents from a liquid vial into a drug vial for mixing or reconstitution purposes in a similar manner to hitherto mentioned U.S. Pat. No. 6,558,365 to Zinger et al.

The liquid drug transfer devices can employ different mechanical arrangements for converting manual rotation into a linear displacement for drug vial puncturing purposes. Suitable mechanical arrangements include inter alia a screw thread arrangement, a pin and track arrangement, and the like. Some liquid drug transfer devices employ the same mechanical arrangement for both their drug vial flow communication step and their liquid container flow communication step. Other liquid drug transfer devices employ one mechanical arrangement for their drug vial flow communication step and another mechanical arrangement for their liquid container flow communication step. Selection of mechanical arrangements is a function of different design features to balance between the number of rotations required and the torque to be applied by a user to effect the manual rotation. The higher the number of rotations the less the torque required and vice versa.

The liquid drug transfer devices of the present invention can be classified into one of two types depending on an intended liquid container as follows: Infusion liquid container type and liquid vial type.

In the infusion liquid container type, a liquid container adapter is constituted by an access port adapter typically in the form of an injection port adapter. A dual ended liquid transfer member can terminate in an access port flow member co-directional with the longitudinal device axis and initially spaced apart from an access port of an infusion liquid container for subsequent urging along the longitudinal device axis during a liquid container flow communication step for sliding insertion into the access port. Alternatively, an access port adapter can include an access port flow member for insertion into an access port on attachment of the access port adapter onto an infusion liquid container, and a dual ended liquid transfer device can terminate in an infusion liquid container stopcock arrangement for selective opening and closing flow communication with the access port flow member.

In the liquid vial type, a liquid container adapter is constituted by a liquid vial adapter similar to a drug vial adapter. A leading liquid transfer member end also terminates in a puncturing tip co-directional with the longitudinal device axis and initially spaced apart from an uppermost liquid vial surface of an initially intact liquid vial for subsequent urging along the longitudinal device axis during a liquid vial flow communication step for puncturing a liquid vial stopper for flow communication with a liquid vial interior. Also, the dual ended liquid transfer member preferably has a dual component construction including a drug vial component and a liquid vial component. The drug vial component preferably terminates in a connector for subsequent aspiration of liquid drug contents from a drug vial. The connector is preferably a female connector. Pursuant to flow communication between a liquid vial and a drug vial, a liquid vial component of a liquid transfer member is intended to be detached from its counterpart drug vial component such that the two components remain attached to their respective vial adapters.

The liquid drug transfer devices are preferably supplied as so-called "ready to use" medical devices insofar as they are supplied with at least a pre-attached intact drug vial. The liquid drug transfer devices can also additionally be supplied with a pre-attached liquid container be it either a pre-attached infusion liquid container or a pre-attached intact liquid vial. Each pre-attachment is instead of a user attachment and therefore facilitates user convenience and in particular precludes incorrect telescopic clamping of a vial adapter on a drug vial. Moreover, ready to use medical devices reduce drug waste because they facilitate patient bedside preparation immediately prior to use as opposed to be remote preparation in a compound pharmacy remote from a patient bedside which can lead to unused drugs.

Pre-attached intact drug vials can be clamped in drug vial adapters intended for enabling detachment by a release tool still in their intact state, for example, in the case that a patient no longer requires a drug medicament. The released intact drug vial can be placed in a controlled environment for storage purposes and re-attachment to a liquid drug transfer device for subsequent administration. Alternatively, pre-attached drug vials can be clamped in drug vial adapters precluding their detachment. Still again, liquid drug transfer devices can be supplied without a pre-attached drug vial and/or a pre-attached liquid container thereby requiring a user to attach a liquid drug transfer device to a drug vial and a liquid container.

Some liquid drug transfer devices can include a conventional drug vial adapter for telescopic clamping on a single size of a drug vial, namely, a small drug vial or a large drug vial. Alternatively, liquid drug transfer devices can optionally include a universal drug vial adapter designed for telescopic clamping equally on a drug vial of a single drug vial and a large drug vial. Suitable universal drug vial adapters are illustrated and described in commonly owned PCT International Application No. PCT/IL2013/050706 filed Aug. 20, 2013 and entitled Liquid Drug Transfer Devices. The liquid drug transfer devices can similarly include either a conventional liquid vial adapter for telescopic clamping on a single size of a liquid vial or a universal liquid vial adapter.

Some liquid drug transfer devices can be preferably provided with a user indication for indicating establishment of flow communication between a liquid container and a drug vial. User indications can be in the form of visual indications and/or audible indications, for example, a click.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which:

FIG. 6C is a longitudinal cross section of FIG. 6B along line D-D thereon;

DETAILED DESCRIPTION OF PREFERRED EMBODIMENTS OF THE INVENTION

Figure 1:
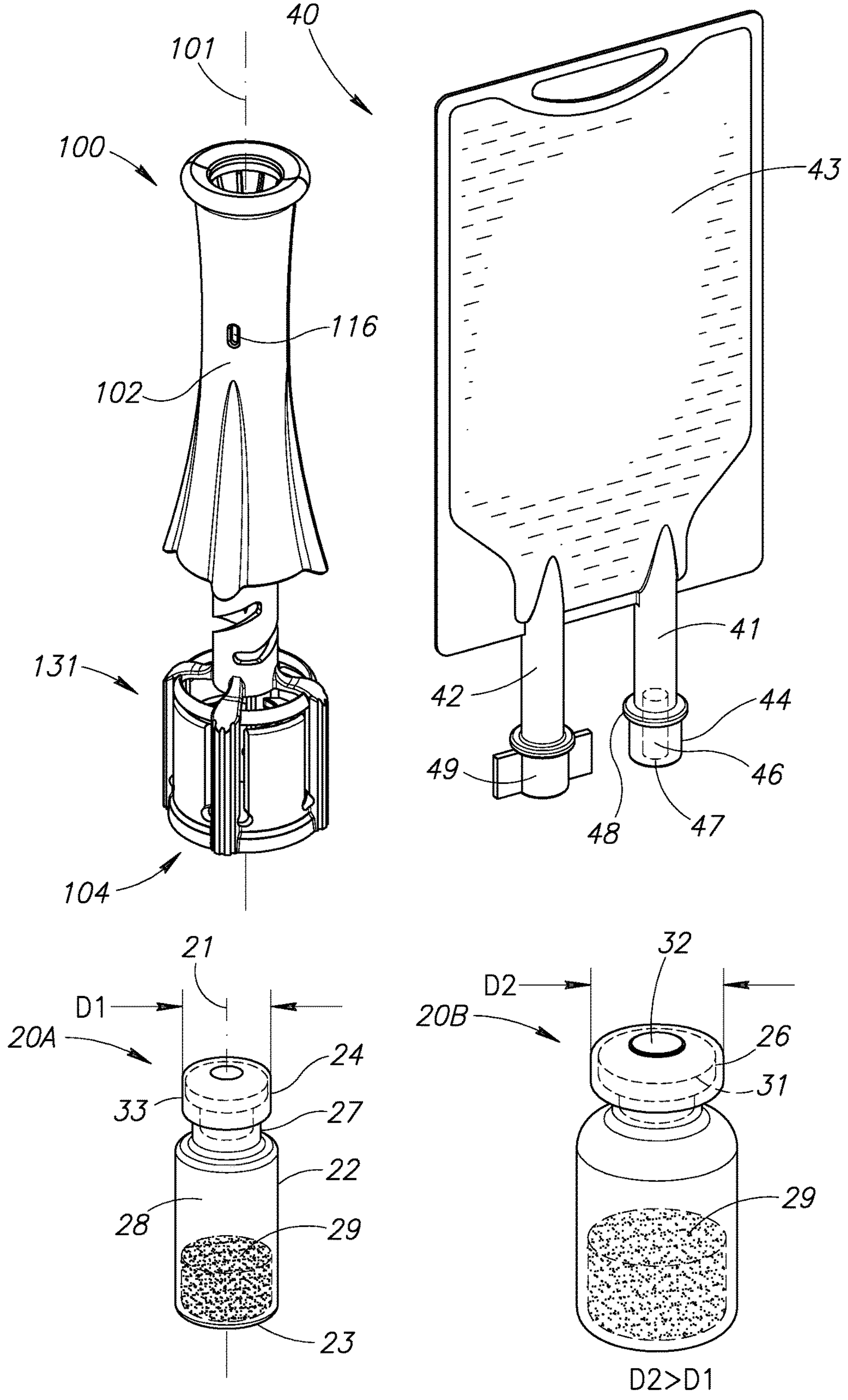
FIG. 1 is a front perspective view of a first preferred embodiment of a liquid drug transfer device in accordance of the present invention in an initial pre-actuated state, a small drug vial, a large drug vial, and an IV bag.
Figure 2:
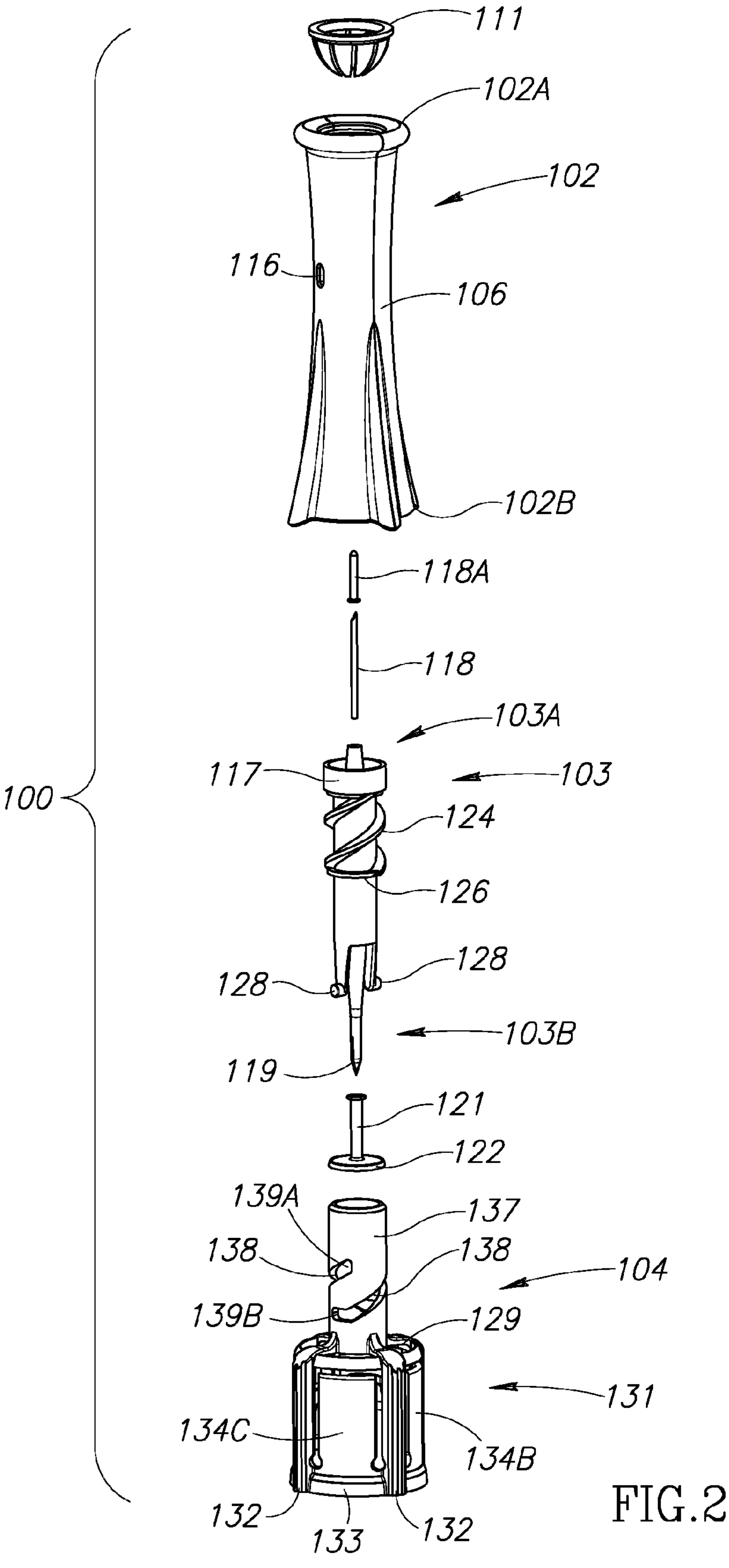
FIG. 2 is an exploded view of FIG. 1's liquid drug transfer device.

FIGS. 1 to 14 show three liquid drug transfer devices 100, 200 and 300 for use with a drug vial 20 of a small drug vial 20A and a large drug vial 20B and a liquid container constituted by an infusion liquid container depicted as an IV bag 40. The liquid drug transfer devices 100, 200 and 300 are similar insofar as each has a longitudinal device axis 101 and includes a liquid container adapter 102 constituted by an access port adapter, a liquid transfer member 103 and a drug vial adapter 104 constituted by a universal drug vial adapter. Their access port adapters 102 each has a leading access port adapter end 102A and a trailing access port adapter end 102B. Their liquid transfer members 103 each has a leading liquid transfer member end 103A disposed toward an access port adapter 102 for engaging same and a trailing liquid transfer member end 103B disposed toward a drug vial adapter 104 for engaging same.

The drug vials 20 have a longitudinal drug vial axis 21 and include a drug vial bottle 22 having a drug vial base 23, a drug vial head 24 defining a drug vial opening 26, and a narrow diameter drug vial neck 27 between the drug vial bottle 22 and the drug vial head 24. The drug vials 20 have a drug vial interior 28 for storing a powder or liquid medicament 29. The drug vials 20 are sealed by a drug vial stopper 31 inserted into the drug vial opening 26. The drug vials 20 have an uppermost drug vial surface 32. The drug vial heads 24 are typically sealed by a drug vial closure 33, for example, an aluminum band, and the like.

Large drug vials have the same shape as small drug vials but proportionally larger dimensions. In particular, large drug vials have a drug vial closure and a drug vial neck with wider diameters than their counterpart small drug vials. Widely commercially available small drug vials 20A have a drug vial closure 33 with an external diameter D1 of between 13 mm and 14 mm and widely commercially available large drug vials 20B have a drug vial closure 33 with an external diameter D2>D1 and typically between 20 mm and 21 mm. The present invention is equally applicable to larger so-called small drug vials and so-called large drug vials containing larger liquid volumes, for example, a 28 mm diameter drug vial closure and a 32 mm diameter drug vial closure, respectively.

The IV bag 40 includes two types of access ports, namely, an injection port 41 and an administration port 42, and contains liquid contents 43. The IV bag ports 41 and 42 are in the form of plastic tubing. The injection port 41 terminates in an injection port tip 44 containing a self-sealing plug 46 with an exposed plug surface 47 intended for needle injection of syringe contents into the IV bag 40. The injection port tip 44 has a trailing injection port tip rim 48. The administration port 42 is typically sealed by a twist off cap 49 for insertion of an IV spike for administration purposes.

The liquid drug transfer devices 100, 200 and 300 are illustrated and described for attachment to an injection port 41 and can be equally implemented for attachment to an administration port 42.

In greater particularity, FIGS. 1 to 7 show the liquid drug transfer device 100 includes an injection port adapter 102 engaging the leading liquid transfer member end 103A by means of a screw thread mechanical arrangement and the trailing liquid transfer member end 103B engaging the universal drug vial adapter 104 by means of a pin and track mechanical arrangement. The liquid drug transfer device 100 employs a manual rotation for executing an initial drug vial flow communication step for establishing flow communication between the liquid transfer member 103 and a drug vial 20 and a subsequent liquid container flow communication step for establishing flow communication between the liquid transfer member 103 and the IV bag 40, thereby establishing flow communication between the drug vial 20 and the IV bag 40.

The injection port adapter 102 has a tubular housing 106 formed with a leading injection port recess 107 with a transverse injection port recess wall 108 with an inner injection port recess wall rim 108A defining a throughgoing injection port recess wall aperture 109. The leading injection port recess 107 is preferably provided with a universal injection port connector 111 for attachment on the injection port 41 as also illustrated and described in hitherto mentioned commonly owned PCT International Application No. PCT/IL2013/050706 filed Aug. 20, 2013 and entitled Liquid Drug Transfer Devices.

The housing 106 has an internal surface 112 provided with a leading transverse inward directed annular abutment rib 113A and a trailing transverse inward directed annular abutment rib 113B for controlling displacement of the liquid transfer member 103. The internal surface 112 is formed with guide ribs 114 towards the trailing injector port adapter end 102B for guiding purposes during linear compaction of the universal drug vial adapter 104 towards the injection port adapter 102. The housing 106 is formed with a throughgoing slot 116 towards the leading injection port adapter end 102A for enabling a visual user indication regarding establishment of flow communication between an IV bag and a drug vial.

The leading liquid transfer member end 103A is provided with a liquid transfer member head 117 with an access port flow member 118 constituted by a needle for needle insertion into the injection port 41. The liquid transfer member head 117 is disposed on the abutment rib 113A in a pre-actuated state of the liquid drug transfer device 100. The liquid transfer member 103 includes a sleeve 119 for initially covering the needle 118 for ensuring the needle 118 remains sterile until it punctures the injection port 41. The liquid transfer member head 117 has an exterior brightly colored surface for providing a visual user indication through the throughgoing slot 116 on execution of a manual rotation to establish flow communication between an IV bag 40 and a drug vial 20.

The trailing liquid transfer member end 103B terminates in a puncturing tip 119 for puncturing a drug vial stopper 31. The liquid transfer member 103 includes a sleeve 121 for initially covering the puncturing tip 119 for ensuring the puncturing tip 119 remains sterile until it punctures a drug vial stopper 31. The sleeve 121 includes a circular base 122 shaped and dimensioned for placing on the uppermost drug vial surface 32. The liquid transfer member 103 is formed with an axial lumen 123 for flow communication between the needle 118 and the puncturing tip 119.

The leading liquid transfer member end 103A has a liquid transfer member head drill bit like section 124 for screw thread engaging the abutment rib 113A on manual rotation of the drug vial adapter 104 in a clockwise tightening direction around the longitudinal device axis 101 for needle insertion of the needle 118 into the injection port 41. The drill bit like section 124 includes a trailing stop member 126 for stopping against the abutment rib 113B for stopping linear displacement of the liquid transfer member 103 towards the injection port adapter 102. The trailing liquid transfer member end 103B is formed with a pair of outward directed radial pins 128 for enabling rotation of the liquid transfer member 103 relative to the injection port adapter 102 by means of the universal drug vial adapter 104.

The universal drug vial adapter 104 includes a transverse vial adapter top wall 129 with an inner top wall rim 129A defining a throughgoing top wall aperture 130 along the longitudinal device axis 101. The universal drug vial adapter 104 includes a downward depending vial adapter skirt 131 for telescopically clamping on a drug vial closure 33 such that the throughgoing top wall aperture 130 overlies an uppermost drug vial surface 32. The vial adapter skirt 131 includes four equispaced downward depending supports 132 supporting a trailing circular member 133. The circular member 133 is formed with resiliently flexible upward depending grip members 134 arranged in a first pair of opposite grip members 134A and 134B and an orthogonal second pair of opposite grip members 134C and 134D. The grip members 134 are each formed with an internal directed gripper 136 for gripping a drug vial closure 33.

The vial adapter top wall 129 is formed with an axial directed upright tubular drug vial adapter stem 137 encircling the throughgoing top wall aperture 130 and opposite the downward depending vial adapter skirt 131. The drug vial adapter stem 137 has a pair of opposite generally helical tracks 138 for corresponding engagement by the pair of outward directed radial pins 128. The tracks 138 each have a start track end 139A remote from the vial adapter top wall 129 and a final track end 139B adjacent the vial adapter top wall 129.

The liquid transfer member 103 is disposed in the drug vial adapter stem 137 such that its puncturing tip 119 is spaced apart from an uppermost drug vial surface 32 of an initially intact non-punctured drug vial 20 clamped in the downward depending vial adapter skirt 131 in the pre-actuated state of the liquid drug transfer device 100. The pair of outward directed radial pins 128 are typically deployed at the start track ends 139A. The puncturing tip 119 passes through the throughgoing top wall aperture 130 on displacement of the liquid transfer member 103 from the start track ends 139A to the final track ends 139B for puncturing through a drug vial stopper 31 for establishing flow communication with a drug vial interior 28.

Figure 3A:
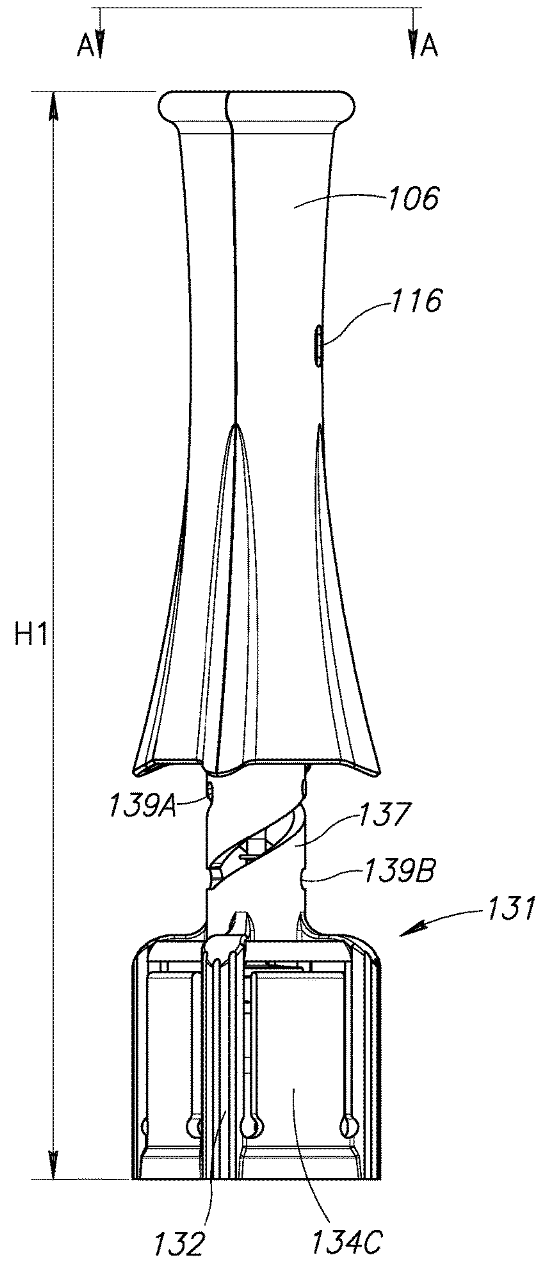
FIG. 3A is a front elevation view of FIG. 1's liquid drug transfer device in a pre-actuated state prior to manual rotation.
Figure 3B:
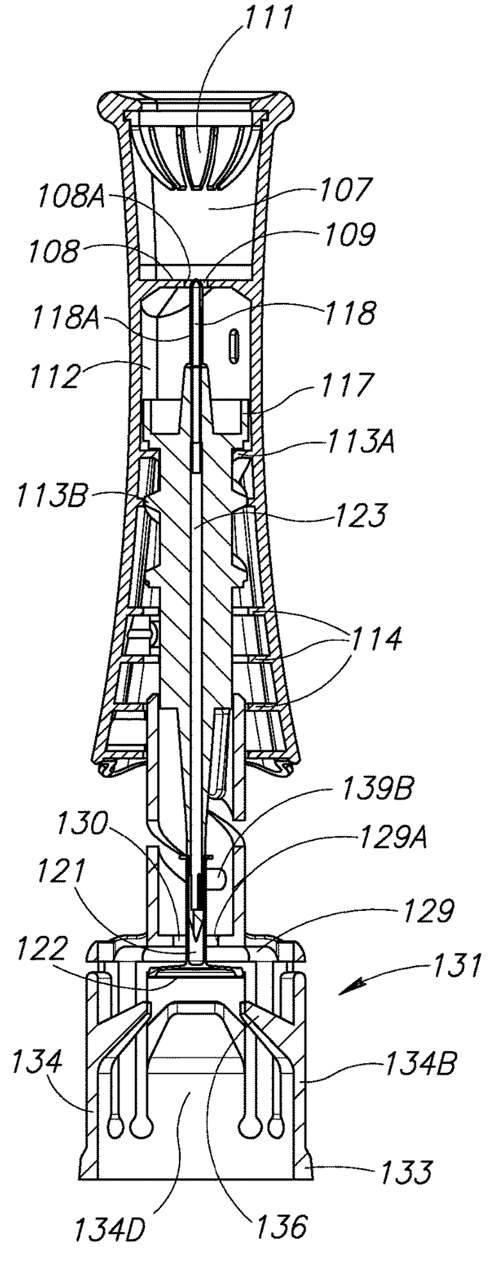
FIG. 3B is a longitudinal cross section of FIG. 1's liquid drug transfer device along line A-A in FIG. 3A.

FIGS. 3A and 3B show the liquid drug transfer device 100 in its pre-actuated state with the drug vial adapter 104 is at its most remote location from the injection port adapter 102. The liquid drug transfer device 100 has a pre-actuated height H1. The liquid transfer member 103 is deployed at the abutment rib 113A and the needle 118 is disposed at the throughgoing injection port recess wall aperture 109 ready to be urged into the leading injection port recess 107. The outward directed radial pins 128 are deployed at the start track ends 136A and the puncturing tip 119 is disposed above the downward depending vial adapter skirt 131 and preferably above the throughgoing top wall aperture 130.

Figure 4A:
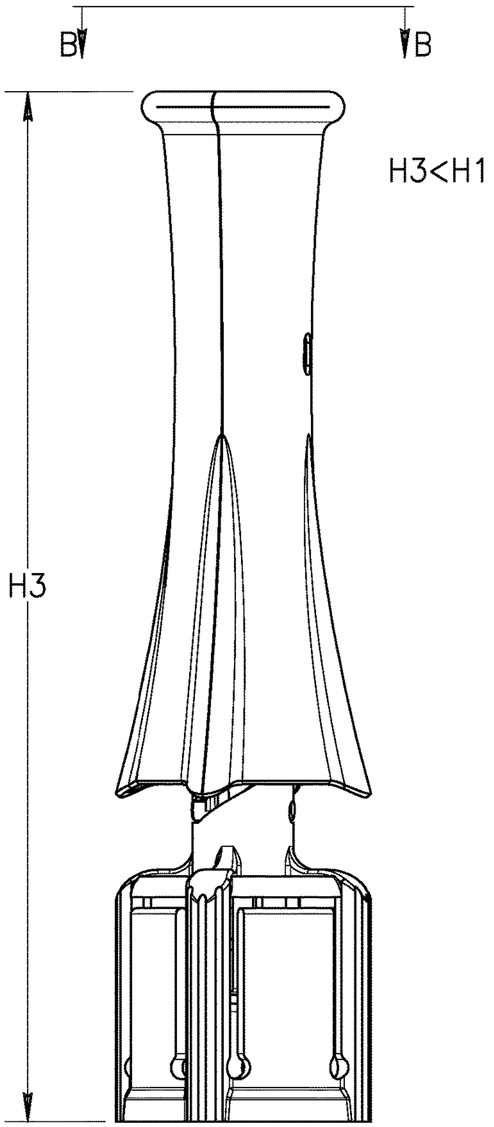
FIG. 4A is a front elevation view of FIG. 1's liquid drug transfer device in an intermediate actuated state pursuant to execution of a drug vial flow communication step of a manual rotation.
Figure 4B:
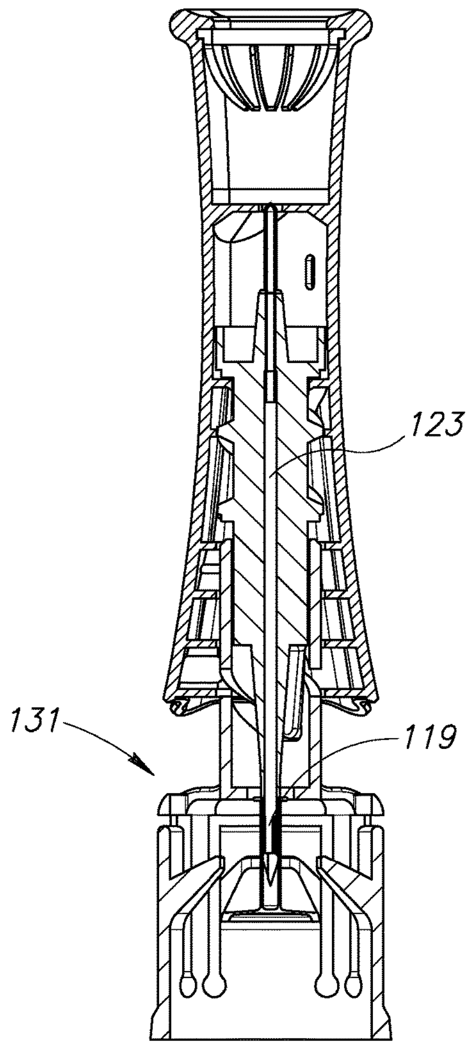
FIG. 4B is a longitudinal cross sectional of FIG. 1's liquid drug transfer device along line B-B in FIG. 4A.

FIGS. 4A and 4B show the liquid drug transfer device 100 pursuant to execution of a drug vial flow communication step of a manual rotation of the universal drug vial adapter 104 with respect to the injection port adapter 102 around the longitudinal device axis 101 in a clockwise tightening direction. The manual rotation urges the universal drug vial adapter 104 to travel to the final track ends 139B whilst the liquid transfer member 103 remains stationary with respect to the injection port adapter 102. This relative linear displacement between the injection port adapter 102 and the universal drug vial adapter 104 leads to the puncturing tip 119 puncturing a drug vial stopper 31 for establishing flow communication between the liquid transfer member 103 and a drug vial 20. The liquid drug transfer device 100 has an intermediate actuated height H3 where H3<H1.

Figure 5A:
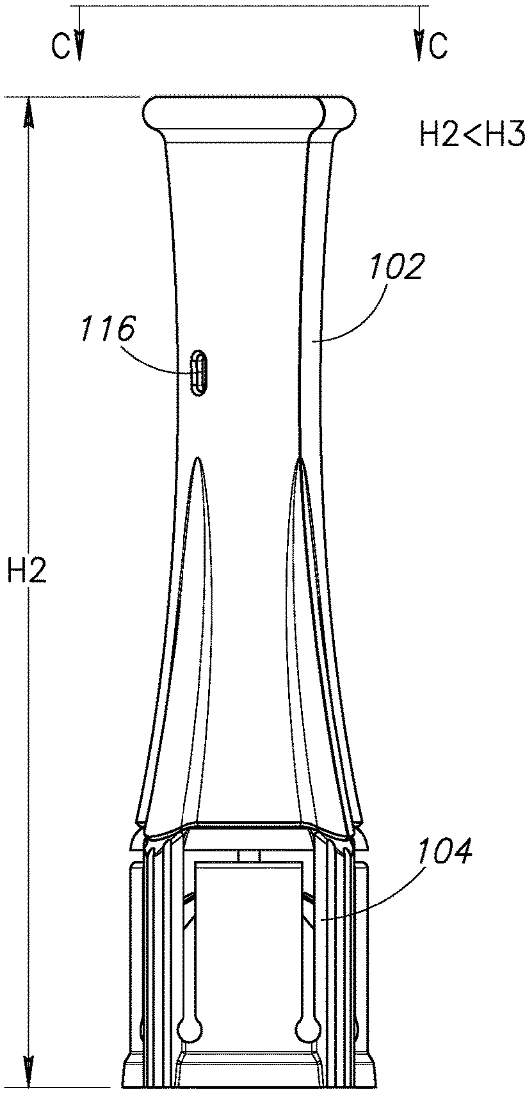
FIG. 5A is a front elevation view of FIG. 1's liquid drug transfer device in its post-actuated state pursuant to subsequent execution of its liquid container flow communication step of a manual rotation.
Figure 5B:
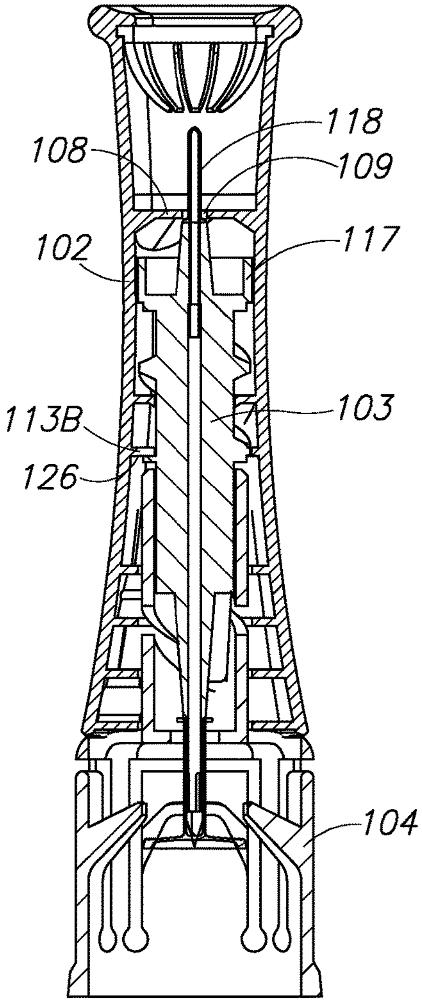
FIG. 5B is a longitudinal cross sectional of the liquid drug transfer device along line C-C in FIG. 5A.

FIGS. 5A and 5B show the liquid drug transfer device 100 pursuant to execution of a liquid container communication step of continued manual rotation of the universal drug vial adapter 104 relative to the injection port adapter 102. The liquid drug transfer device 100 has a post-actuated height H2 where H2<H3 and therefore H2<H1. The continued manual rotation urges the liquid transfer member 103 to travel along the abutment rib 113A until the trailing stop member 126 stops against the abutment rib 113B such that the universal drug vial adapter 104 is adjacent the injection port adapter 102. The needle 118 is urged into the leading injection port recess 107 for needle insertion into an injection port 41 for establishing flow communication between the liquid transfer member 103 and an IV bag 40 and therefore a drug vial 20. The liquid transfer member head 117 is visible through the throughgoing slot 116 such that the user is aware the liquid drug transfer device 100 is now in its actuated state.

FIGS. 6A to 6E show the use of the liquid drug transfer device 100 with a pre-attached drug vial 20A. The use of the liquid drug transfer device 100 with a pre-attached drug vial 20B is the same for the liquid drug transfer device 100 with a pre-attached drug vial 20A.

Figure 6A:
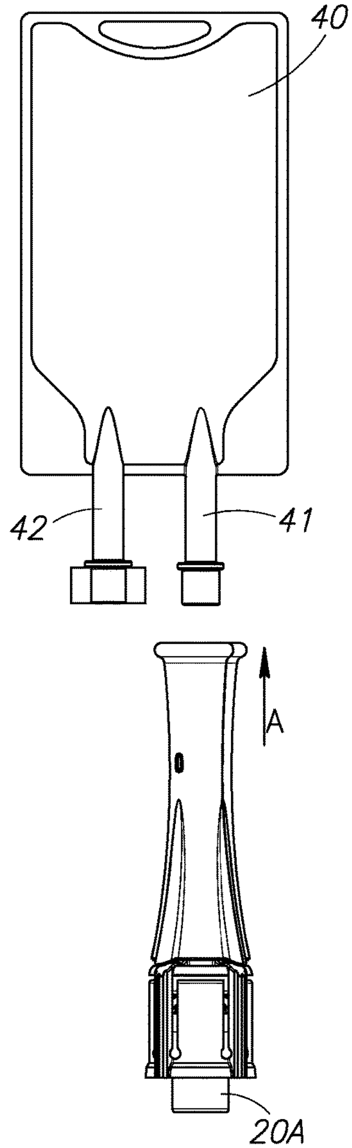
FIGS. 6A, 6B, 6C, 6D, and 6E show the use of FIG. 1's liquid drug transfer device with a pre-attached small drug vial for introducing a drug vial medicament to an IV bag and administration of infusion liquid contents.

FIG. 6A shows attaching a liquid drug transfer device 100 to the IV bag 40 as denoted by arrow A for insertion of the injection port 41 into the leading injection port recess for attachment to the injection port connector.

Figure 6B:
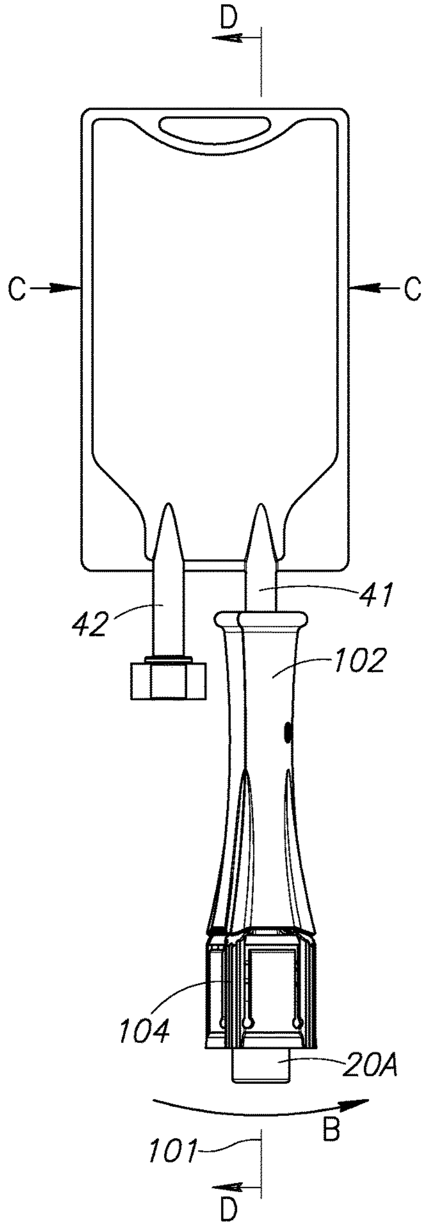

FIG. 6B shows manual rotation of the universal drug vial adapter 104 relative to the injection port adapter 102 in a clockwise tightening direction around the longitudinal device axis 101 as denoted by arrow B to urge the liquid drug transfer device 100 to establish flow communication between the IV bag 40 and the drug vial 20A. The liquid transfer member head 117 is visible through the slot 116 to indicate flow communication. The user squeezes the IV bag 40 as denoted by arrows C for transferring liquid contents from the IV bag 40 to the drug vial 20A for reconstitution or dilution purposes. The user may gently agitate the assemblage to ensure full reconstitution of powder contents.

Figure 6C:
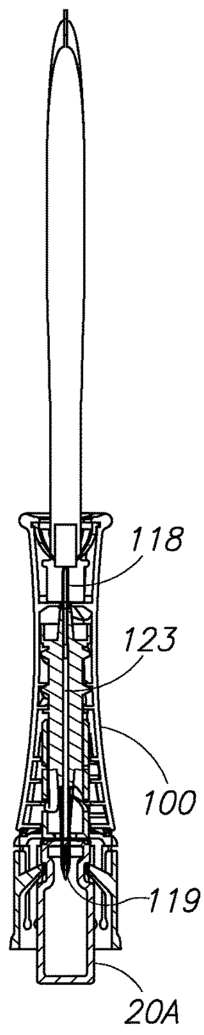

FIG. 6C shows the flow communication between the IV bag 40 and the drug vial 20A via the needle 118, the axial lumen 123 and the puncturing tip 119.

Figure 6D:
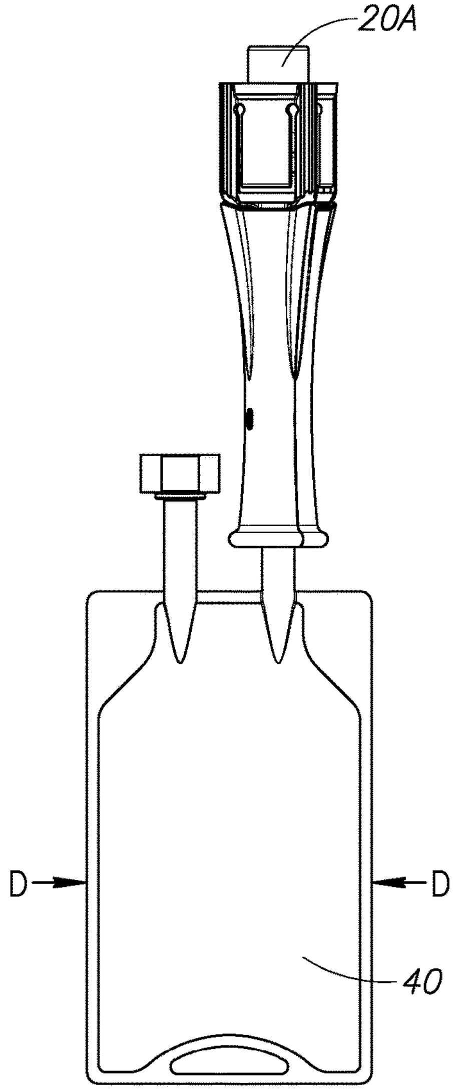

FIG. 6D shows inverting the IV bag 40, the liquid drug transfer device 100 and the drug vial 20A and squeezing air from the IV bag 40 into the drug vial 20A as denoted by arrows D for draining liquid drug contents from the drug vial 20A into the IV bag 40.

Figure 6E:
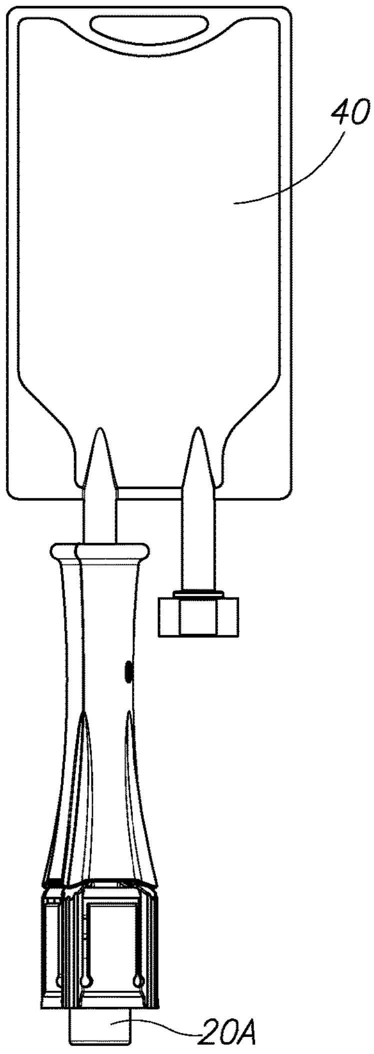

FIG. 6E shows inverting the IV bag 40, the liquid drug transfer device 100 and the now empty drug vial 20A ready for administration of the IV bag liquid contents via an infusion set (not shown).

Figure 7A:
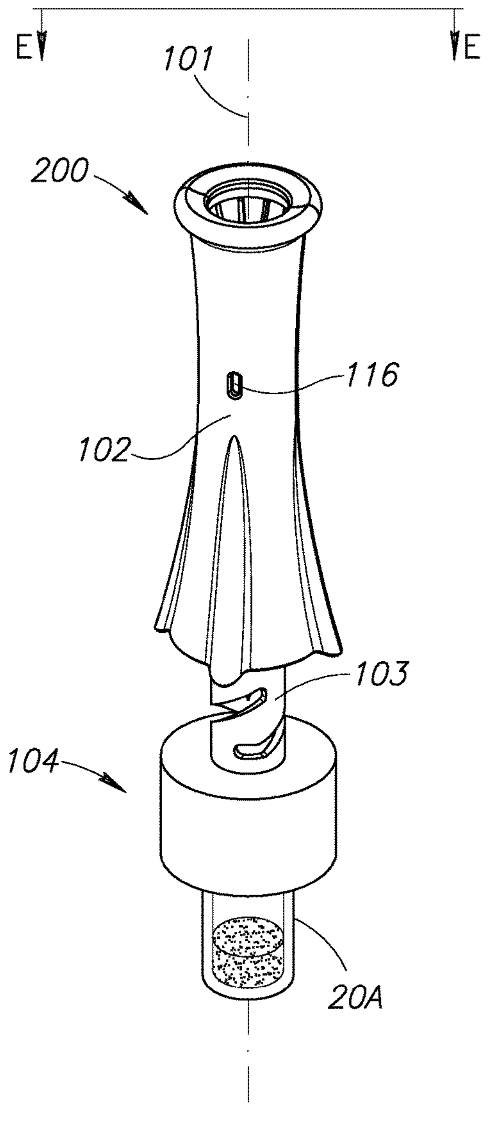
FIG. 7A is a front perspective view of a second preferred embodiment of a liquid drug transfer device in a pre-actuated state in accordance with the present invention.
Figure 7B:
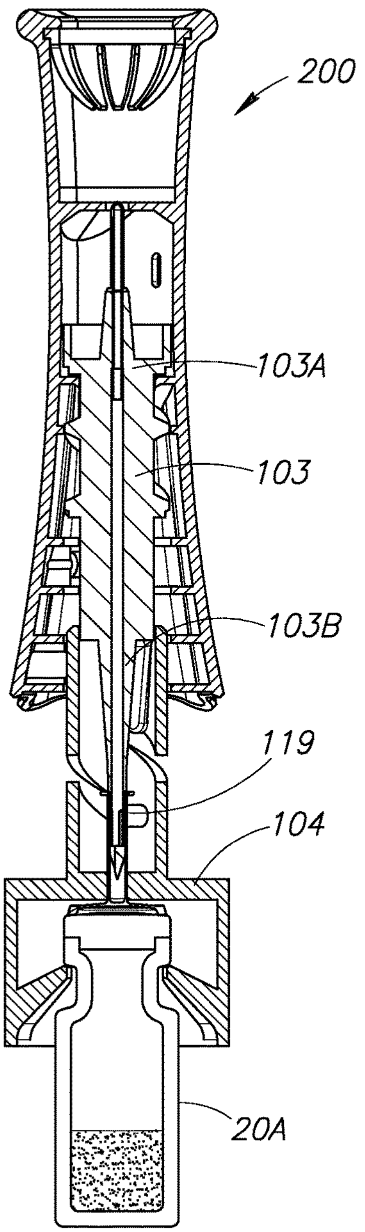
FIG. 7B is a longitudinal cross section of FIG. 7A's liquid drug transfer device along line E-E thereon.
Figure 8:
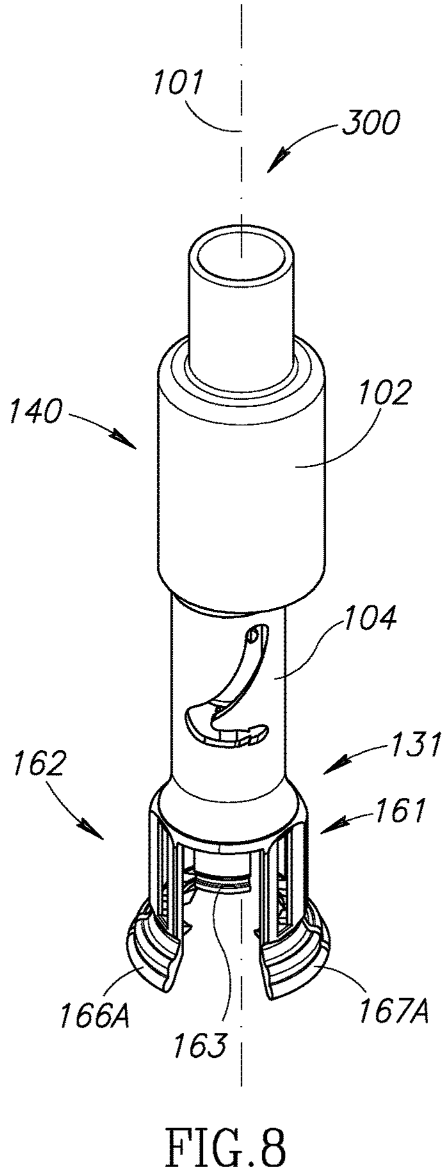
FIG. 8 is a front perspective view of a third preferred embodiment of a liquid drug transfer device in accordance with the present invention in a pre-actuated state.
Figure 9:
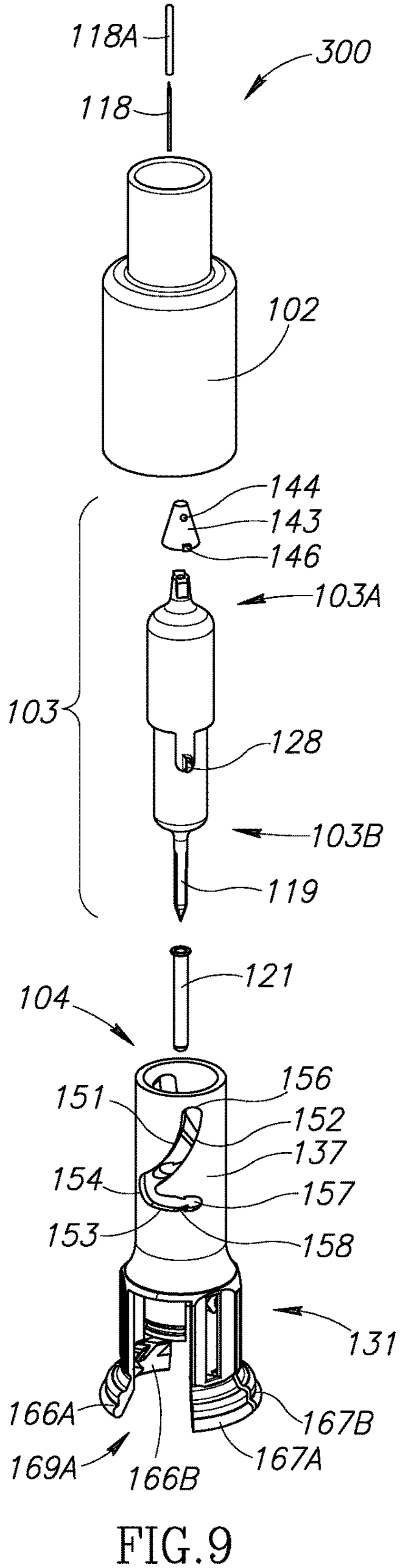
FIG. 9 is an exploded view of FIG. 8's liquid drug transfer device.

FIGS. 7A and 7B show a liquid drug transfer device 200 similar in construction and operation as the liquid drug transfer device 100 and therefore similar parts are likewise numbered. The former 200 differs from the latter 100 insofar as the former 200 includes a drug vial adapter 104 with a pre-attached non-detachable drug vial 20A.

FIGS. 8 to 14 show a liquid drug transfer device 300 for use with a drug vial 20 of a drug vial 20A and a drug vial 20B and an IV bag 40 similar to the liquid drug transfer device 100. The former 300 has a general similar construction as the latter 100 and therefore similar parts are likewise numbered as follows: The liquid drug transfer device 300 has a longitudinal device axis 101 and includes an injection port adapter 102, a liquid transfer member 103 and a universal drug vial adapter 104.

The former 300 differs from the latter 100 insofar that the former 300 employs a manual rotation for executing an initial liquid container flow communication step for establishing flow communication between the liquid transfer member 103 and an infusion liquid container and a subsequent drug vial flow communication step for establishing flow communication between the liquid transfer member 103 and a drug vial, thereby establishing flow communication between the infusion liquid container and the drug vial. Moreover, the former 300 differs from the latter 100 insofar that the former 300 employs the manual rotation for executing a linear compaction of the drug vial adapter 104 towards the injection port adapter 102 for drug vial puncturing and operation of an infusion liquid container stopcock arrangement 140 for selective flow communication between the injector port adapter 102 and an infusion liquid container.

The liquid drug transfer device 300 has a different construction from the liquid drug transfer device 100 in three main respects as follows:

First, the infusion liquid container stopcock arrangement 140 includes the leading injection port recess 107 of the injection port adapter 102 being provisioned with the needle 118 instead of the liquid transfer member 103. The needle 118 is mounted in an axial lumen 141 formed in the injection port recess wall 108. The liquid transfer member 103 and the drug vial adapter 104 have a rotation axis 142 offset from the longitudinal device axis 101. The leading liquid transfer member end 103A terminates in a leading cone 143 formed with a port 144 in flow communication with the axial lumen 123. The cone 143 includes a key 146 for rotational movement along a keyway 147 formed on the inside surface 148 of a cone recess 149 forming part of the injection port recess wall 108 for selective alignment of the port 144 with the axial lumen 141 for enabling flow communication with the needle 118.

The infusion liquid container stopcock arrangement 140 has a closed flow position in which the key 146 is at a first extreme position along the keyway 147 for misaligning the port 144 with the lumen 141, thereby disabling flow communication between the needle 118 and the liquid transfer member 103. The infusion liquid container stopcock arrangement 140 has an open flow position in which the key 146 is at a second extreme position along the keyway 147 opposite to the first extreme position for aligning the port 144 with the axial lumen 141 for establishing flow communication between the needle 118 and the liquid transfer member 103's axial lumen 123.

Second, the trailing liquid transfer member end 103B is formed with an opposite pair of inverted generally L-shaped tracks 151 instead of the helical tracks 138. The tracks 151 each include an upright spiral leg 152 and a horizontal leg 153 meeting at a juncture 154. The spiral legs 152 each have a sealed leg end 156 opposite their corresponding junctures 154. The horizontal legs 153 each have a sealed leg end 157 opposite their corresponding junctures 154. The sealed leg ends 157 are each formed with a lock feature 158 for locking their corresponding outward radial pin 128.

For the purpose of execution of a drug vial flow communication step for drug vial puncturing purposes, the sealed leg ends 156 correspond with the start track ends 139A and the junctures 154 correspond with the final track ends 139B.

Third, the universal drug vial adapter 104 has a downward depending skirt 131 for telescopic clamping on a drug vial 20. The vial adapter skirt 131 includes an inner vial grip 161 for snap fitting onto a small drug vial 20A and an outer vial grip 162 for snap fitting onto a large drug vial 20B. The inner vial grip 161 includes two opposite flex members 163 each formed with an inner directed rim 164 for snap fitting on a small drug vial 20's drug vial closure 33. The outer vial grip 162 encircles the inner vial grip 161 and includes a first pair of adjacent flex members 166A and 166B and a second pair of adjacent major flex members 167A and 167B opposite the first pair of major flex members 166A and 166B. The major flex members 166 and 167 are each formed with an inner directed rim 168 for snap fitting on a large drug vial 20B's drug vial closure 33.

The flex members 166A and 166B are adjacent. The flex members 167A and 167B are adjacent. The flex members 166A and 167A are spaced apart to leave a separation therebetween 169A. The flex members 166B and 167B are spaced apart to leave a separation therebetween 169B. The flex members 163A and 163B are correspondingly aligned with the separations 169A and 169B thereby enabling their outward flexing to be unhindered by the flex members 166 and 167 on snap fitting the universal drug vial adapter 104 onto a drug vial 20A.

Figure 10A:
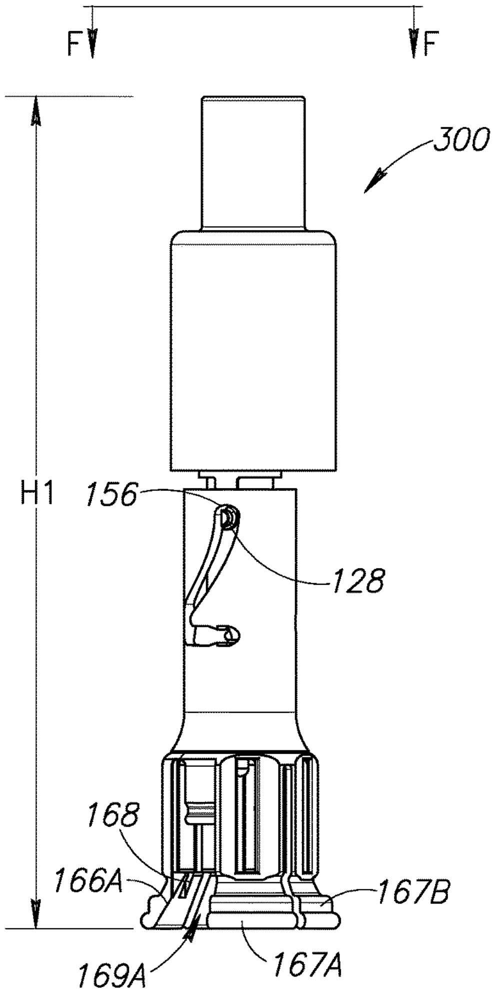
FIG. 10A is a right side elevation view of FIG. 8's liquid drug transfer device in its pre-actuated state including a closed stopcock position.
Figure 10B:
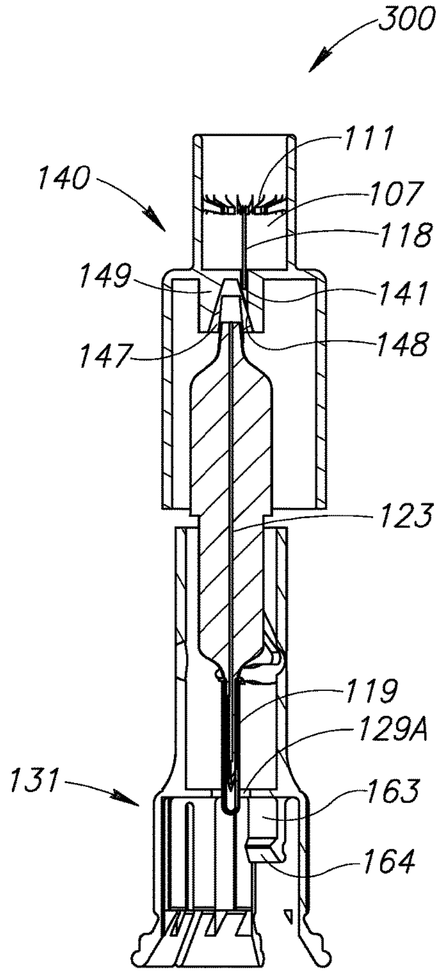
FIG. 10B is a longitudinal cross sectional of FIG. 8's liquid drug transfer device along line F-F in FIG. 10A.

FIGS. 10 to 14 show the use of the liquid drug transfer device 300 as follows:

FIGS. 10A and 10B show the liquid drug transfer device 300 in its pre-actuated state with a pre-actuated height H1. The infusion liquid container stopcock arrangement 140 is in a closed flow position with the key 146 deployed at its first extreme position along the keyway 147 such that the port 144 is not in flow communication with the axial lumen 141. The outward directed radial pins 128 are deployed at the sealed leg ends 156 such that the puncturing tip 119 is disposed so as to be spaced apart from an uppermost drug vial surface 32 of a drug vial 20 clamped in the downward depending skirt 131.

Figure 11A:
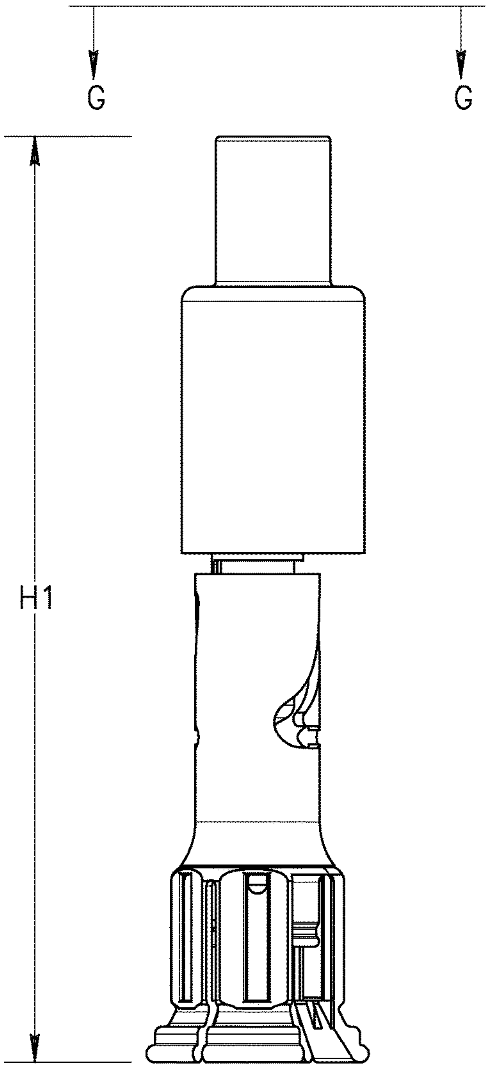
FIG. 11A is a front elevation view of FIG. 8's liquid drug transfer device in an intermediate actuated state including an open stopcock position pursuant to execution of a liquid container flow communication step of a manual rotation.
Figure 11B:
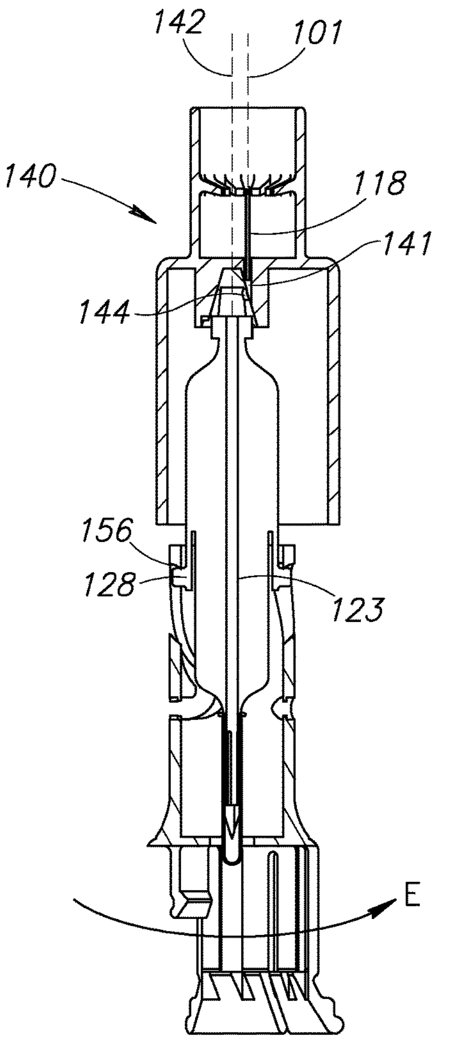
FIG. 11B is a longitudinal cross section of FIG. 8's liquid drug transfer device along line G-G in FIG. 11A.

FIGS. 11A and 11B show the liquid drug transfer device 300 with its infusion liquid container stopcock arrangement 140 in its open flow position pursuant to a liquid container flow communication step of a manual rotation of the universal drug vial adapter 104 relative to the injection port adapter 102 in a clockwise tightening direction round the rotation axis 142 as denoted by arrow E. The liquid container flow communication step causes the liquid transfer member 103 to rotate together with the universal drug vial adapter 104 relative to the injection port adapter 102 until the key 146 stops at the opposite extreme end of the keyway 147. In this position, the port 144 is aligned with the axial lumen 141 to establish flow communication between the needle 118 and the axial lumen 123. The pins 128 remain in their initial position at the sealed leg ends 156. The liquid drug transfer device 300 remains at its pre-actuated height H1.

Figure 12A:
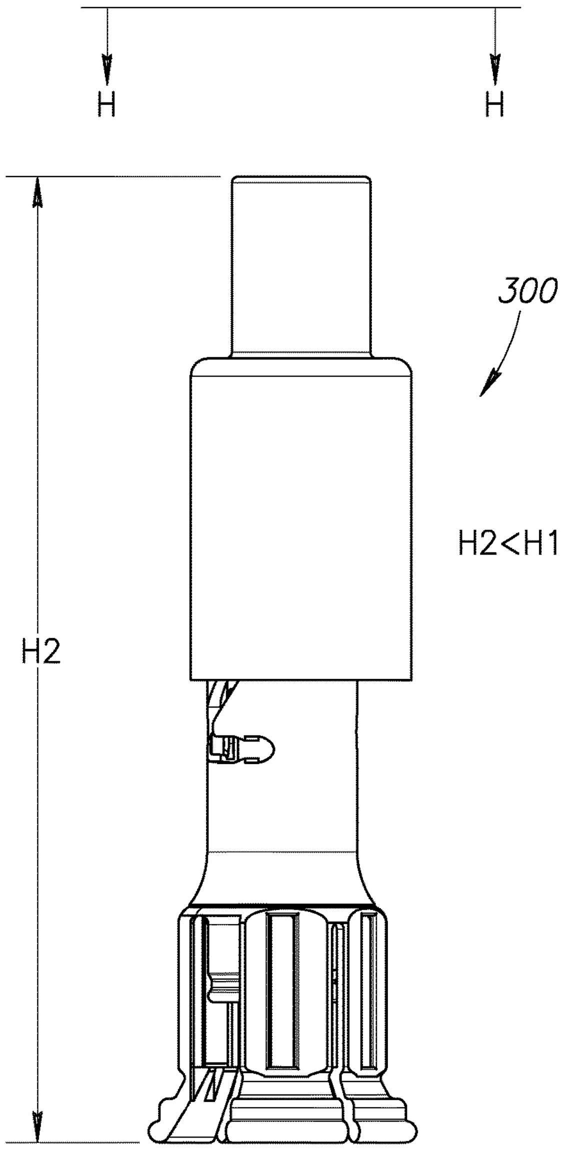
FIG. 12A is a front elevation view of FIG. 8's liquid drug transfer device in its post-actuated state pursuant to execution of a drug vial flow communication step of a manual rotation.
Figure 12B:
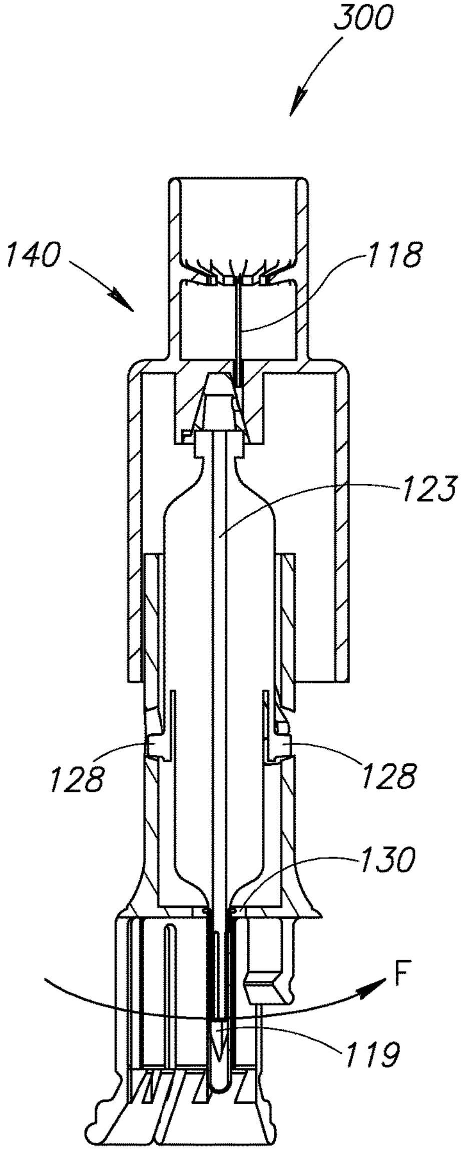
FIG. 12B is a longitudinal cross section of FIG. 8's liquid drug transfer device along line H-H in FIG. 12A.

FIGS. 12A and 12B show the liquid drug transfer device 300 remaining with the infusion liquid container stopcock arrangement 140 in its open flow position and subsequent to a drug vial flow communication step of a continuing manual rotation of the universal drug vial adapter 104 in a clockwise tightening direction round the rotation axis 142 relative to the injection port adapter 102 as denoted by arrow F. Due to further rotation of the liquid transfer member 103 being stopped by the keyway 147, the continuing manual rotation urges the universal drug vial adapter 104 along the upright spiral legs 152 towards the injection port adapter 102. This relative movement causes the puncturing tip 119 to traverse through the throughgoing top wall aperture 130 into the downward depending skirt 131. The continuing manual rotation stops when the pair of outward directed radial pins 128 reach the junctures 154. The port 144 remains aligned with the axial lumen 141 such thereby establishing flow communication between the needle 118 and the puncturing tip 119. The liquid drug transfer device 300 is at its post-actuated height H2 where H2<H1.

Figure 13A:
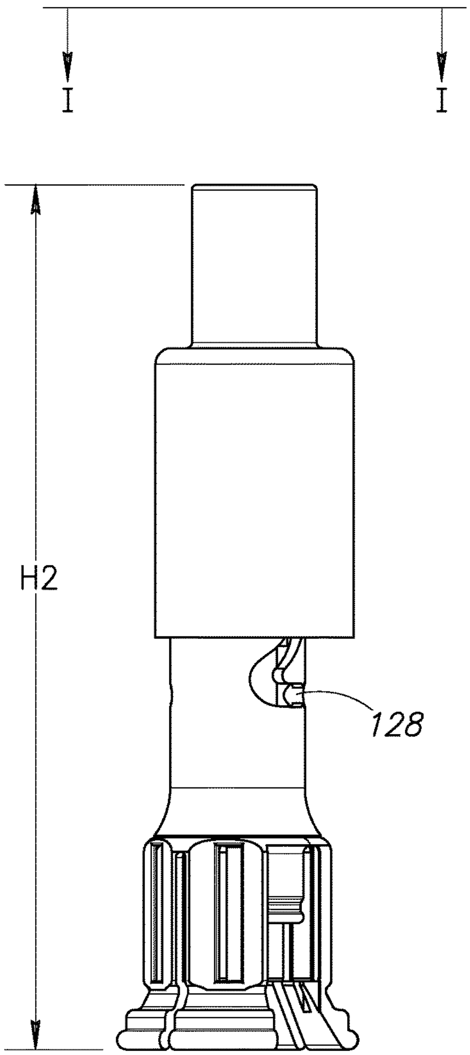
FIG. 13A is a front elevation view of FIG. 8's liquid drug transfer device in a locking step of a manual rotation.
Figure 13B:
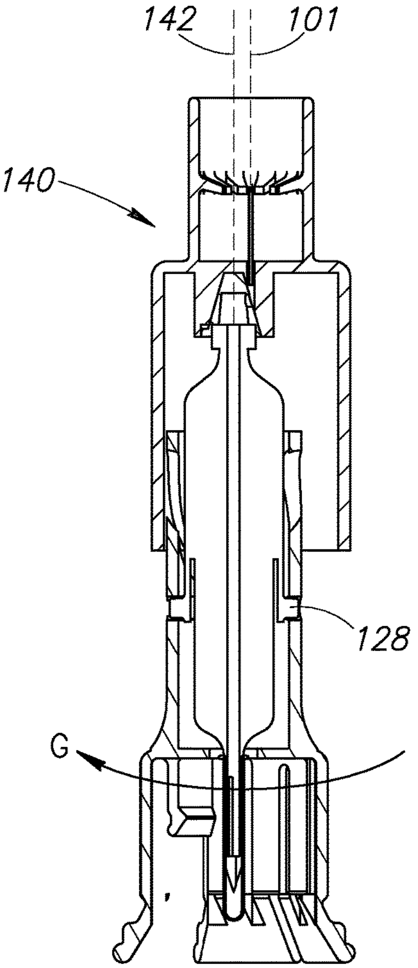
FIG. 13B is a longitudinal cross section of FIG. 8's liquid drug transfer device along line I-I in FIG. 13A.

FIGS. 13A and 13B show the liquid drug transfer device 300 subsequent to manual rotation of the universal drug vial adapter 104 relative to the injection port adapter 102 in a counter clockwise loosening direction round the rotation axis 142 as denoted by arrow G. The manual rotation stops when the pins 128 reach the leg ends 157 and are locked by the lock features 158. The infusion liquid container stopcock arrangement 140 remains in its open flow position with the port 144 aligned with the axial lumen 141 for flow communication between the needle 118 and the puncturing tip 119.

Figure 14A:
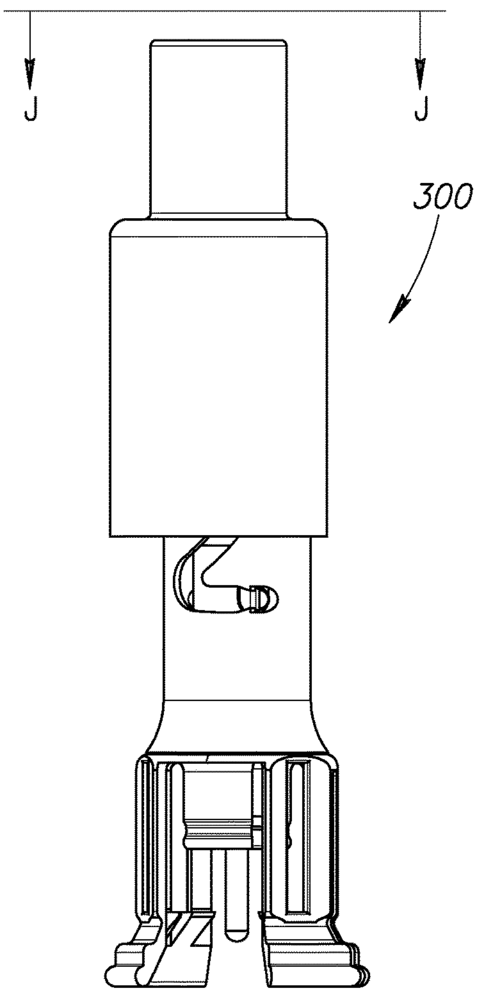
FIG. 14A is a front elevation view of FIG. 8's liquid drug transfer device in a closed stopcock position pursuant to a manual counter-rotation.
Figure 14B:
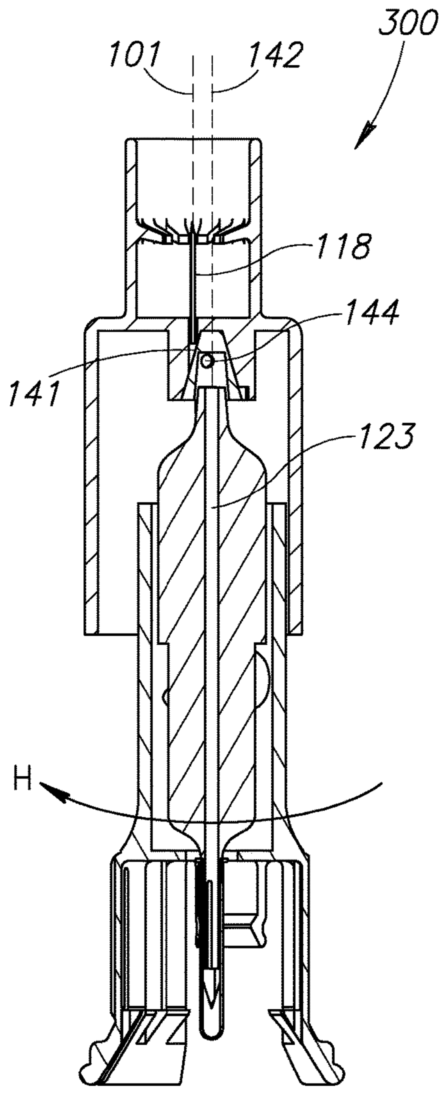
FIG. 14B is a longitudinal cross section of FIG. 8's liquid drug transfer device along line J-J in FIG. 14A.
Figure 15:
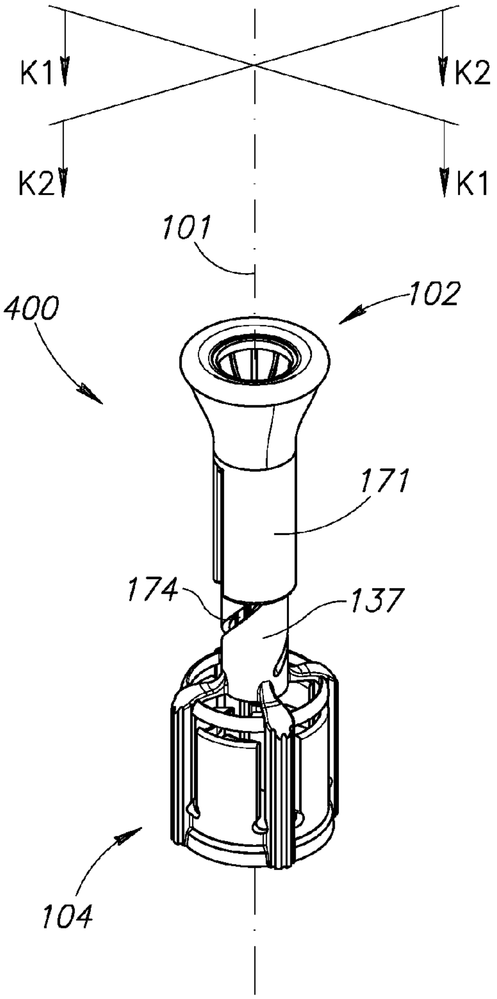
FIG. 15 is a front perspective view of a fourth preferred embodiment of a liquid drug transfer device in a pre-actuated state in accordance with the present invention.
Figure 16:
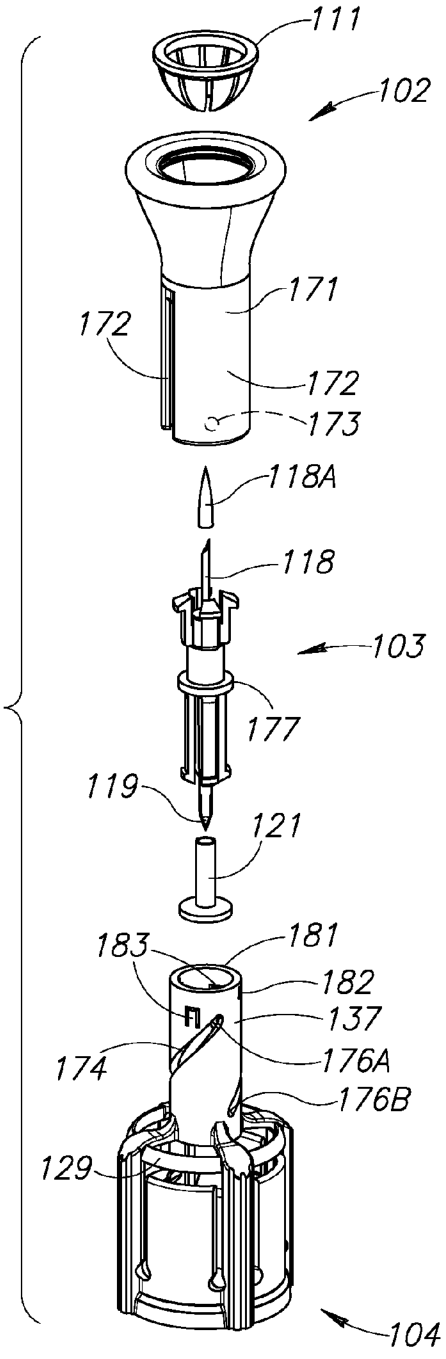
FIG. 16 is an exploded view FIG. 15's liquid drug transfer device including its dual ended liquid transfer member.
Figure 17:
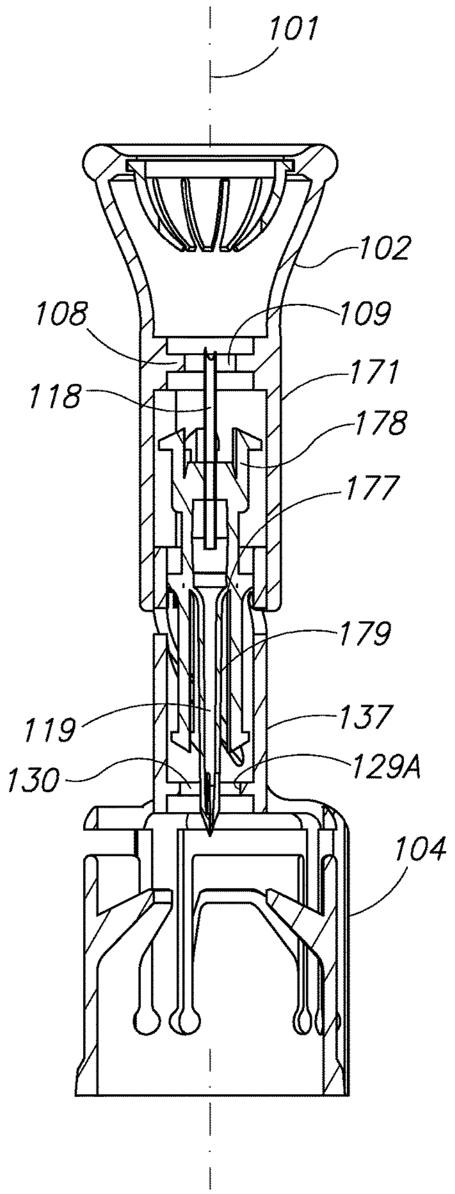
FIG. 17 is a longitudinal cross section of FIG. 15's liquid drug transfer device along line K2-K2 thereon.
Figure 18:
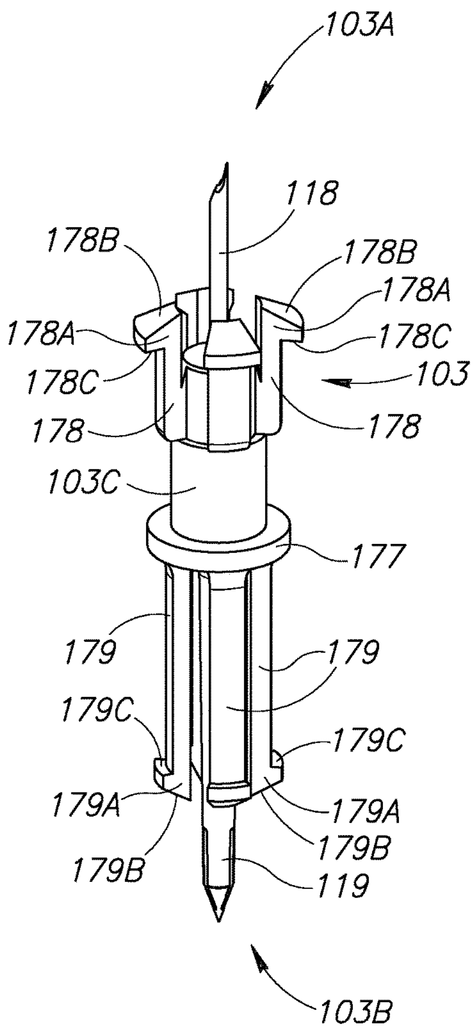
FIG. 18 is a close-up view of FIG. 16s' liquid transfer member.
Figure 19A:
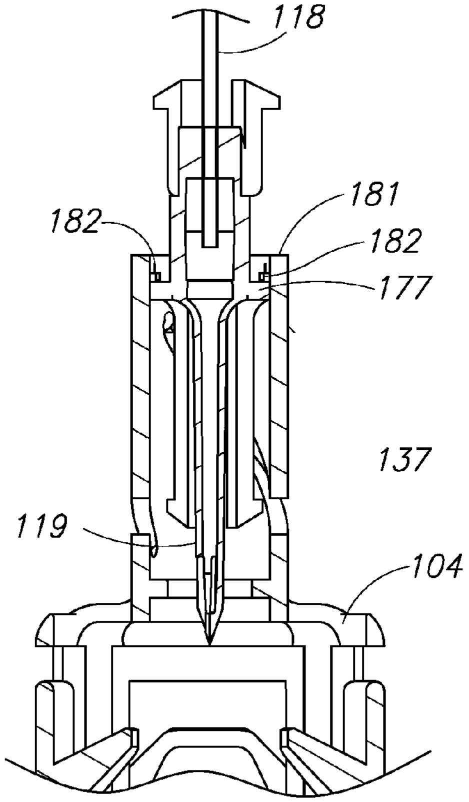
FIG. 19A is a close-up cross section along line K1-K1 in FIG. 15 showing the drug vial adapter stem with a pair of minor stops for retaining the liquid transfer member in its pre-actuated state.
Figure 19B:
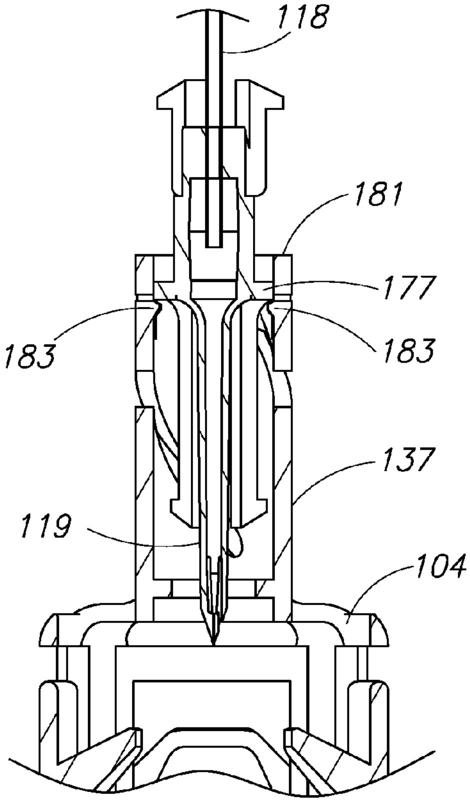
FIG. 19B is a close-up cross section along line K2-K2 in FIG. 15 showing the drug vial adapter stem with a pair of major stops for retaining the liquid transfer member in its pre-actuated state.

FIGS. 14A and 14B show the liquid drug transfer device 300 in an actuated state subsequent to continuing manual rotation of the universal drug vial adapter 103 relative to the injection port adapter 101 in a counter clockwise loosening direction round the rotation axis 142 as denoted by arrow H. Due to further rotation of the universal drug vial adapter 104 relative to the liquid transfer member 103 being stopped by the lock features 158, the continuing manual rotation urges the liquid transfer member 103 to rotate together with the universal drug vial adapter 104 relative to the injection port adapter 102 to return the key 146 to its initial first extreme end of the keyway 147 to close the infusion liquid container stopcock arrangement 140. In this position, the port 144 is not in alignment with the axial lumen 141 thereby disabling flow communication between the needle 118 and the liquid transfer member 103.

FIGS. 15 to 22 show a liquid drug transfer device 400 and FIGS. 23 to 30 show a liquid drug transfer device 500 which are similar to the liquid drug transfer devices 100, 200 and 300 insofar as the former 400 and 500 each has a longitudinal device axis 101, a liquid container adapter 102, a liquid transfer member 103 and a drug vial adapter 104, and therefore similar parts are likewise numbered. The former 400 and 500 differ from the latter 100, 200 and 300 insofar as the former 400 and 500 have a liquid container adapter 102 with an axial directed upright tubular liquid container adapter stem 171 for directly engaging an axial directed upright tubular drug vial adapter stem 137. Also their liquid transfer members 103 are slidingly disposed in their drug vial adapter stems 137 for being urged during the manual rotation of the drug vial adapter 104 relative to the liquid container adapter 102 for puncturing a drug vial stopper 31 for flow communication with a drug vial interior 28.

The liquid drug transfer devices 400 and 500 are similar to the liquid drug transfer devices 100 and 200 insofar the former 400 and 500 include a second linear displacement along the longitudinal device axis 101 for executing a liquid container flow communication step.

The liquid drug transfer devices 400 and 500 are similar to the liquid drug transfer device 300 insofar the former 400 and 500 execute an initial liquid container flow communication step and a subsequent drug vial flow communication step.

The liquid drug transfer device 400 is similar to the liquid drug transfer devices 100, 200 and 300 insofar as the former 400 is intended for use with a drug vial 20 and an infusion liquid container 40. Accordingly, the liquid drug transfer device 400 can be optionally implemented such that a manual rotation executes an initial drug vial flow communication step and a subsequent liquid container flow communication step similar to the liquid drug transfer devices 100 and 200. Additionally, the liquid drug transfer device 400 can be optionally implemented with an infusion liquid container stopcock arrangement similar to the infusion liquid container stopcock arrangement 140.

Figure 23:
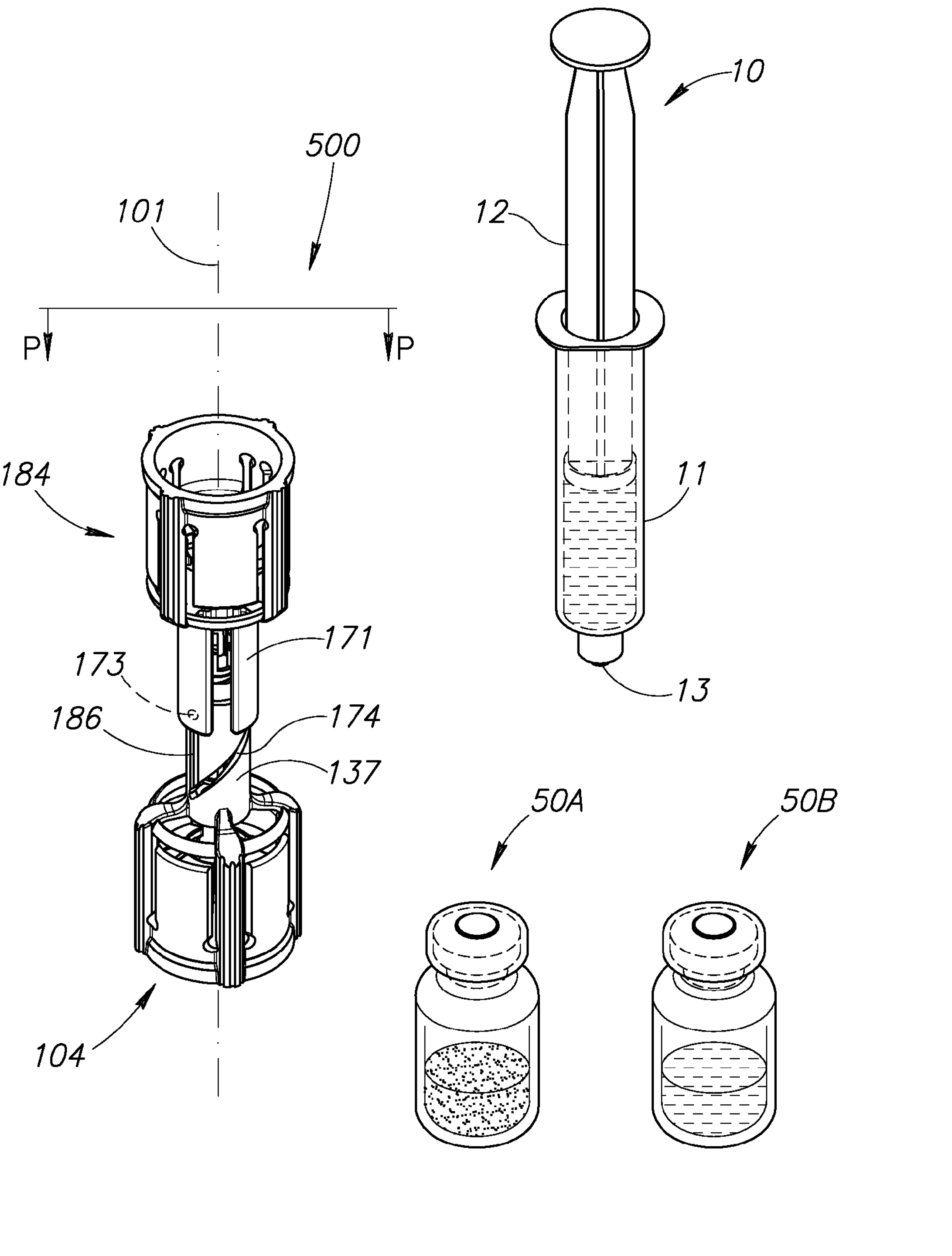
FIG. 23 is a front perspective view of a fifth preferred embodiment of a liquid drug transfer device in a pre-actuated state in accordance with the present invention, a large drug vial, a large liquid vial, and a needleless syringe.
Figure 24:
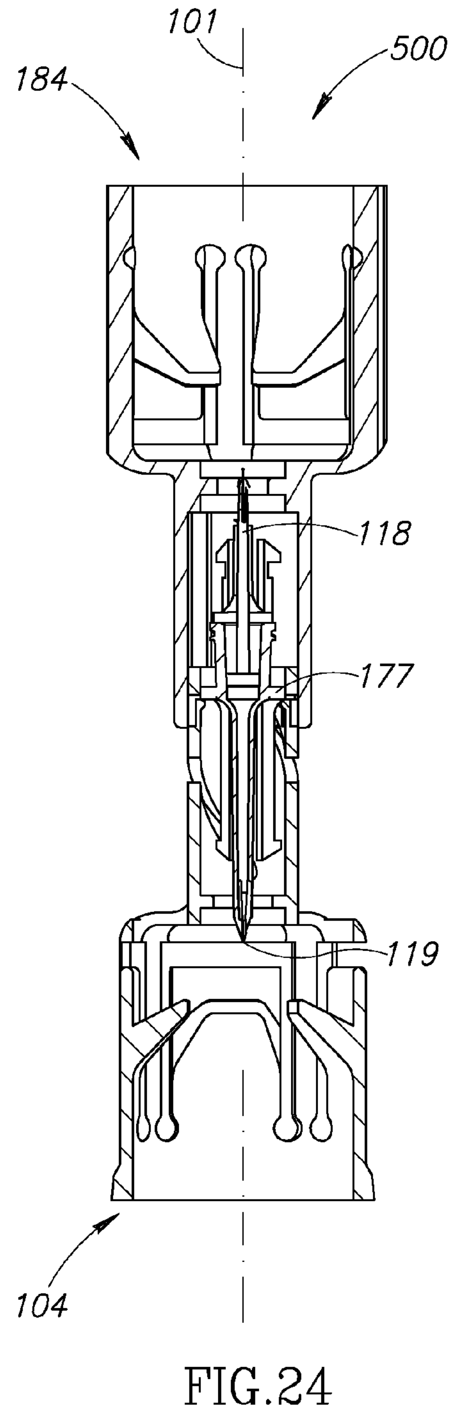
FIG. 24 is a longitudinal cross section of FIG. 23's liquid drug transfer device along line P-P thereon.
Figure 25:
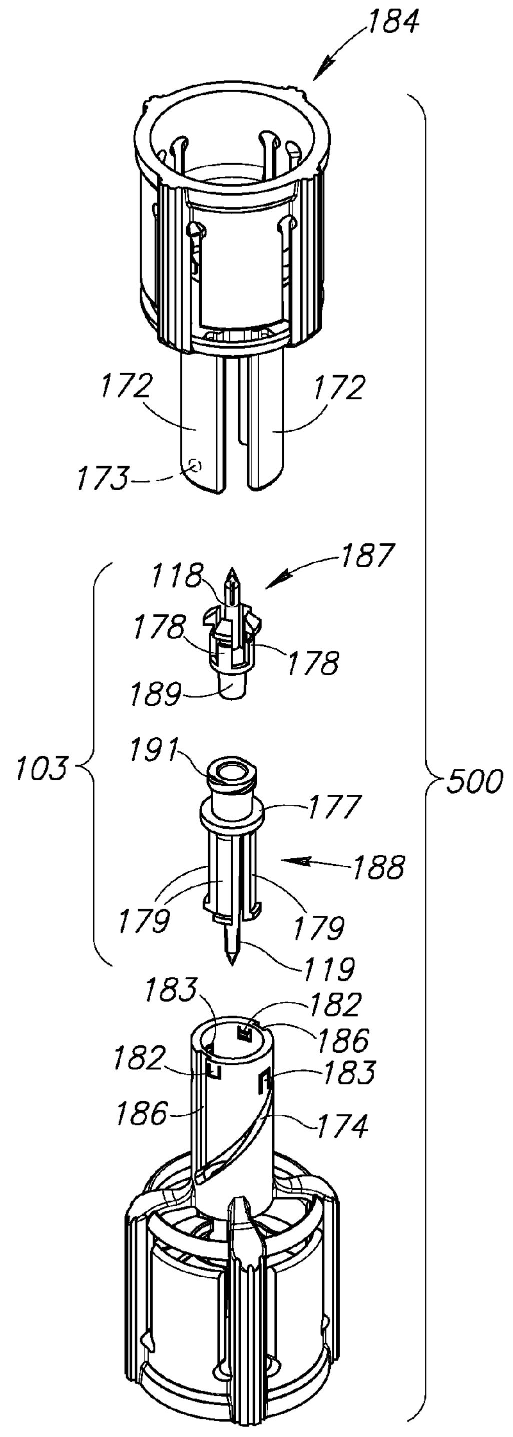
FIG. 25 is an exploded view FIG. 23's liquid drug transfer device.

The liquid drug transfer device 500 is different from the liquid drug transfer devices 100, 200, 300 and 400 insofar as the former 500 is intended for use a drug vial 50A and a liquid vial 50B for filling an initially empty syringe 10 with liquid drug contents as shown in FIG. 23 for administration to a patient. The liquid vial 50B is typically filled with diluent. Alternatively, the liquid vial 50B can include an active liquid component. The syringe 10 includes a barrel 11 with a plunger rod 12 and a male connector 13. The male connector 13 is preferably a male Luer lock connector. The syringe 10 can be formed with other types of male connectors, for example, a slip Luer connector, and the like.

In greater particularity, FIGS. 15 to 19 show the liquid drug transfer device 400 includes a liquid container adapter 102 constituted by an injection port adapter having the universal injection port connector 111 and the liquid container adapter stem 171. The liquid container adapter stem 171 includes a pair of opposite stem members 172 including a pair of inward directed radial pins 173 for sliding engagement along a pair of opposite generally helical tracks 174 formed in the drug vial adapter stem 137 in a similar manner to the pair of tracks 138. The tracks 174 each have a start track end 176A remote from the vial adapter top wall 129 and a final track end 176B adjacent the vial adapter top wall 129.

The liquid transfer member 103 has a central liquid transfer member body 103C intermediate the leading liquid transfer member end 103A and the trailing liquid transfer member 103B. The liquid transfer member 103 includes a needle 118 at its leading liquid transfer member end 103A for needle insertion into an injection port 41 and a puncturing tip 119 at its trailing liquid transfer member end 103B for puncturing a drug vial stopper 31. Sleeves 118A and 121 correspondingly protect the needle 118 and the puncturing tip 119.

The liquid transfer member body 103C is formed with a set of four resiliently mounted axial directed retaining members 178 extending towards the needle 118 for snap fitting onto the injection port adapter 102 during the liquid container flow communication step of the manual rotation of the liquid drug transfer device 400. The retaining members 178 have retaining member tips 178A with inclined leading retaining member tip surfaces 178B and radial directed trailing retaining member tip surfaces 178C. The retaining member tips 178A are inward radial flexed at the central liquid transfer member body 103C towards the longitudinal device axis 101 as their inclined leading retaining member tip surfaces 178B slide along the inner injection port recess wall rim 108A defining the throughgoing injection port recess wall aperture 109 as the needle 118 is urged therethrough. The retaining members 178 revert to their unflexed state as their retaining member tips 178A pass through the throughgoing injection port recess wall aperture 109 whereupon the radial directed trailing retaining member tip surfaces 178C abut the injection port recess wall 108.

Similarly, the liquid transfer member body 103C is formed with a set of four resiliently mounted axial directed retaining members 179 extending towards the puncturing tip 119 for snap fitting onto the drug vial adapter 104 during the drug vial flow communication step of the manual rotation of the liquid drug transfer device 400. The retaining members 179 have retaining member tips 179A with inclined leading retaining member tip surfaces 179B and radial directed trailing retaining member tip surfaces 179C. The retaining member tips 179A are inward radial flexed at the central liquid transfer member body 103C towards the longitudinal device axis 101 as their inclined leading retaining member tip surfaces 179B slide along an inner top wall rim 129A defining the throughgoing top wall aperture 130 as the puncturing tip 119 is urged therethrough. The retaining members 179 revert to their unflexed state as their retaining member tips 179A pass through the throughgoing top wall aperture 130 whereupon the radial directed trailing retaining member tip surfaces 179C snap fit on the inner top wall rim 129A.

The drug vial adapter stem 137 has a leading end face 181 opposite the drug vial adapter skirt 131. The drug vial adapter stem 137 is formed with a pair of inward directed minor stops 182 adjacent the leading end face 181 and a pair of major stops 183 disposed inward from the pair of minor stops 182 by a separation to snugly receive the flange 177 therebetween in a pre-actuated state of the liquid drug transfer device 400. The pair of minor stops 182 and the pair of major stops 183 are orthogonal to one another and employed for ensuring the liquid transfer member 103 remains in place during transportation and for determining the sequence between a drug vial flow communication step and a liquid container flow communication step.

The pair of minor stops 182 are smaller than the pair of major stops 183 such that on manual rotation of the drug vial adapter 104 with respect to the injection port adapter 102, the liquid transfer member flange 177 initially snaps over the pair of minor stops 182 towards the injection port adapter 102 for needle insertion of the needle 118 into an injection port 41 to execute a liquid container flow communication step. On abutment of the leading liquid transfer member end 103A against an injection port 41, the liquid transfer member flange 177 snaps over the pair of major stops 183 towards the drug vial adapter 104 for executing a drug vial flow communication step. The pair of minor stops 182 and the pair of major stops 183 can be reversed in position such that the liquid drug transfer device 400 initially executes a drug vial flow communication step and subsequently executes a liquid container flow communication step.

Figure 20A:
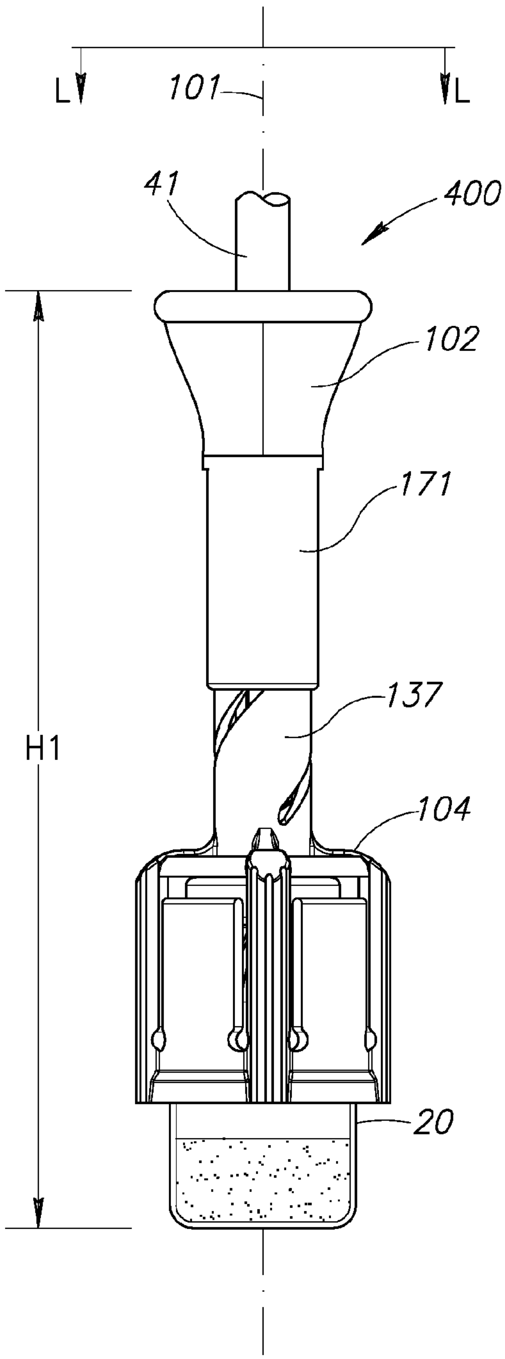
FIG. 20A is a front elevation view of FIG. 15's liquid drug transfer device in a pre-actuated state attached to an injection port and a large drug vial.
Figure 20B:
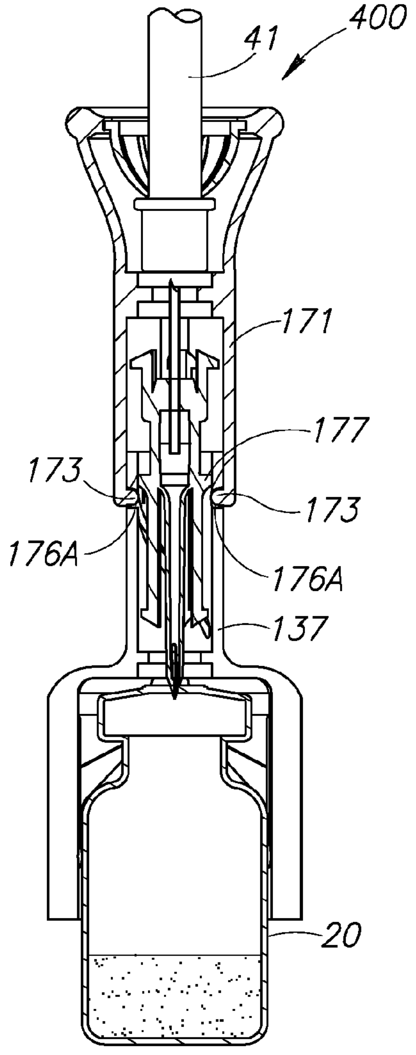
FIG. 20B is a longitudinal cross section of FIG. 20A's liquid drug transfer device along line L-L thereon.

FIGS. 20 to 22 show the use of the liquid drug transfer device 400 as follows:

FIGS. 20A and 20B show the liquid drug transfer device 400 in a pre-actuated state with a pre-actuated height H1.

The pair of minor stops 182 and the pair of major stops 183 retain the liquid transfer member 103 in the drug vial adapter stem 137. The pair of inward directed radial pins 173 are deployed at the start track ends 176A.

Figure 21A:
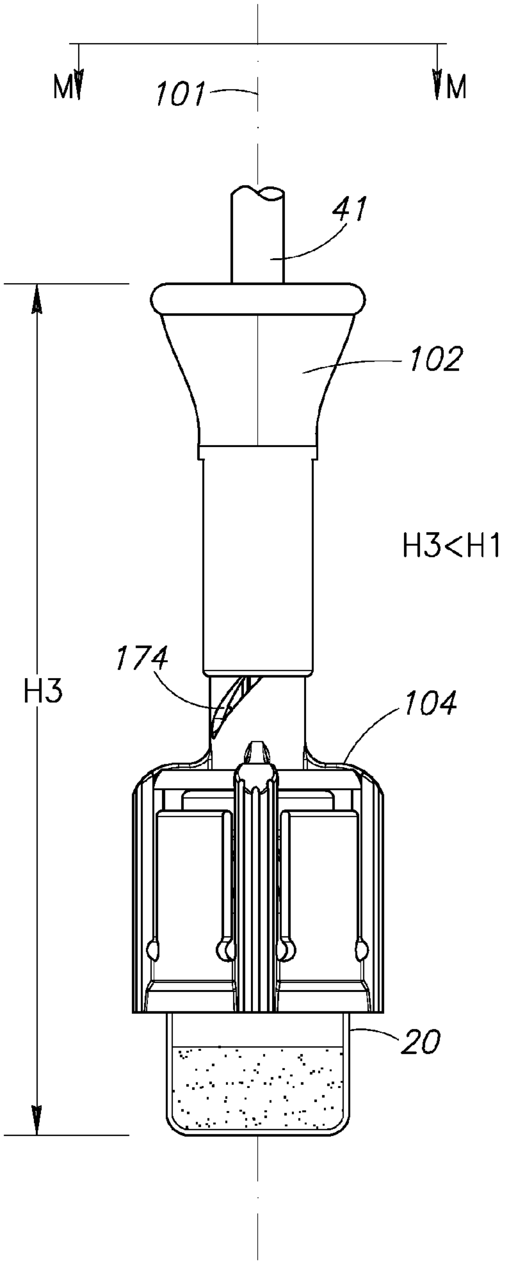
FIG. 21A is a front elevation view of FIG. 20A's assemblage in an intermediate actuated pursuant to a liquid container flow communication step.
Figure 21B:
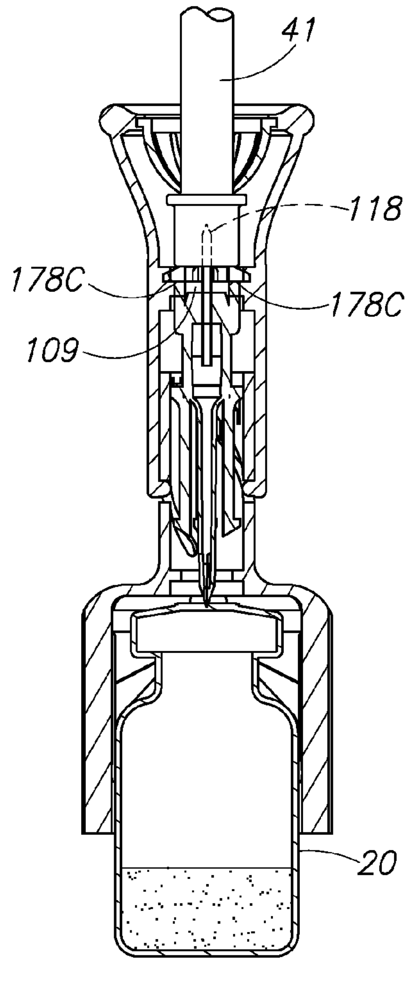
FIG. 21B is a longitudinal cross section of FIG. 21A's assemblage along line M-M thereon.

FIGS. 21A and 21B show the liquid drug transfer device 400 in an intermediate actuated state pursuant to a liquid container flow communication step. The liquid drug transfer device 400 has an intermediate actuated height H3 where H3<H1. The pair of inward directed radial pins 173 are midway along the pair of opposite tracks 174 between the start track ends 176A and the finish track ends 176B. The retaining member tips 178A are snap fitted on the injection port adapter 102 thereby securing the liquid transfer member 103 thereto.

Figure 22A:
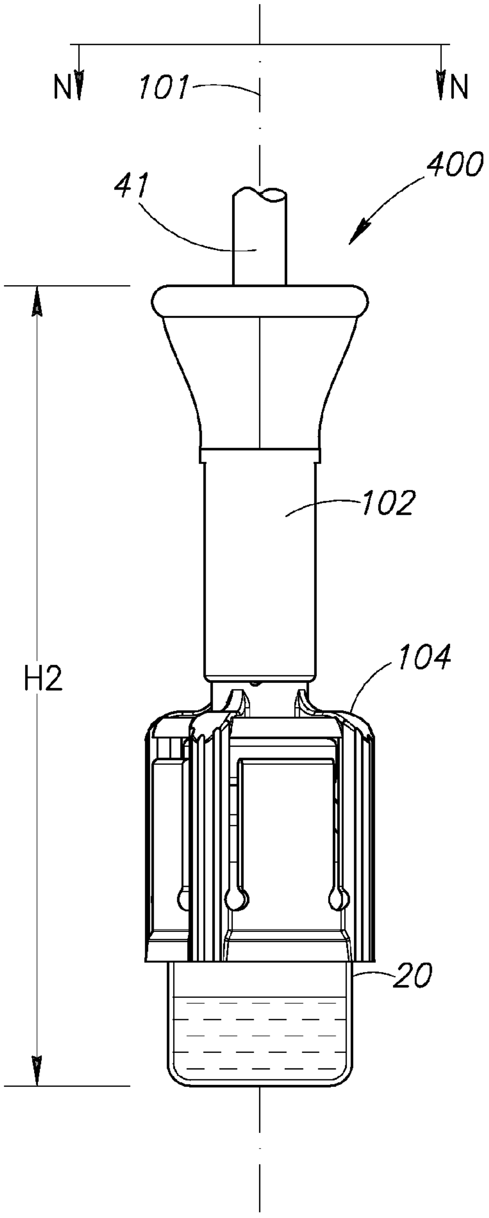
FIG. 22A is a front elevation view of FIG. 20A's assemblage in a post-actuated state.
Figure 22B:
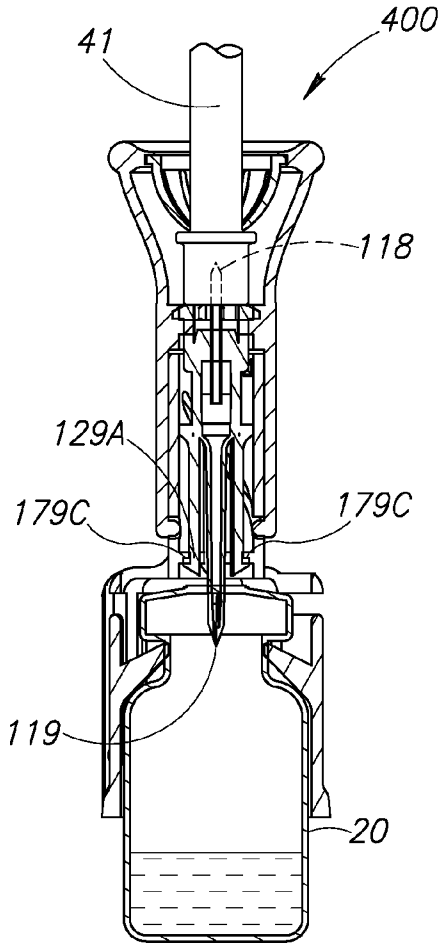
FIG. 22B is a longitudinal cross section of FIG. 22A's assemblage along line N-N thereon.

FIGS. 22A and 22B show the liquid drug transfer device 400 in a post-actuated state after a full linear compaction along the longitudinal device axis 101 following full manual rotation of the drug vial adapter 104 with respect to the infusion liquid adapter 102. The retaining member tips 179A are snap fitted on the inner top wall rim 129A thereby securing the liquid transfer member 103 to the drug vial adapter 104. The liquid drug transfer device 400 has a post-actuated height H2 where H2<H3. Full compaction establishes flow communication between the injection port 41 and the drug vial 20 thereby enabling liquid flow from the IV bag to the drug vial 20.

In greater particularity, FIGS. 23 to 26 show the liquid drug transfer device 500 is similar in construction to the liquid drug transfer device 400 and therefore similar parts are likewise numbered. The former 500 differs from the latter 400 in three major respects as follows.

First, the liquid container adapter 102 is constituted by a liquid vial adapter 184 similar to the drug vial adapter 104. The liquid vial adapter 184 includes the liquid container adapter stem 171.

Second, the drug vial adapter stem 137 is provided with a pair of axial directed release grooves 186. The axial directed release grooves 186 are in sliding communication with the helical tracks 174 for enabling the pair of inward directed radial pins 173 to initial slide down the helical tracks 174 and then slide up the release grooves 186 for enabling detachment of the liquid container adapter stem 171 from the drug vial adapter stem 137 in a post-actuated state of the liquid drug transfer device 500.

And third, the liquid transfer member 103 has a dual component construction including a liquid vial component 187 and a drug vial component 188. The liquid vial component 187 includes the needle 118, an axial directed male connector 189 in flow communication with the needle 118, and the four axial directed retaining members 178. The drug vial component 188 includes the puncturing tip 119, an axial directed female connector 191 in flow communication with the puncturing tip 119 and the four axial directed retaining members 179. The male connector 189 is inserted in the female connector 191 in the pre-actuated state of the liquid drug transfer device 500. The male connector 189 and female connector 191 are preferably Luer connectors. The female connector 191 is also intended to receive the syringe's male connector 13 for syringe aspiration of liquid drug contents from the drug vial 50A.

Figure 26A:
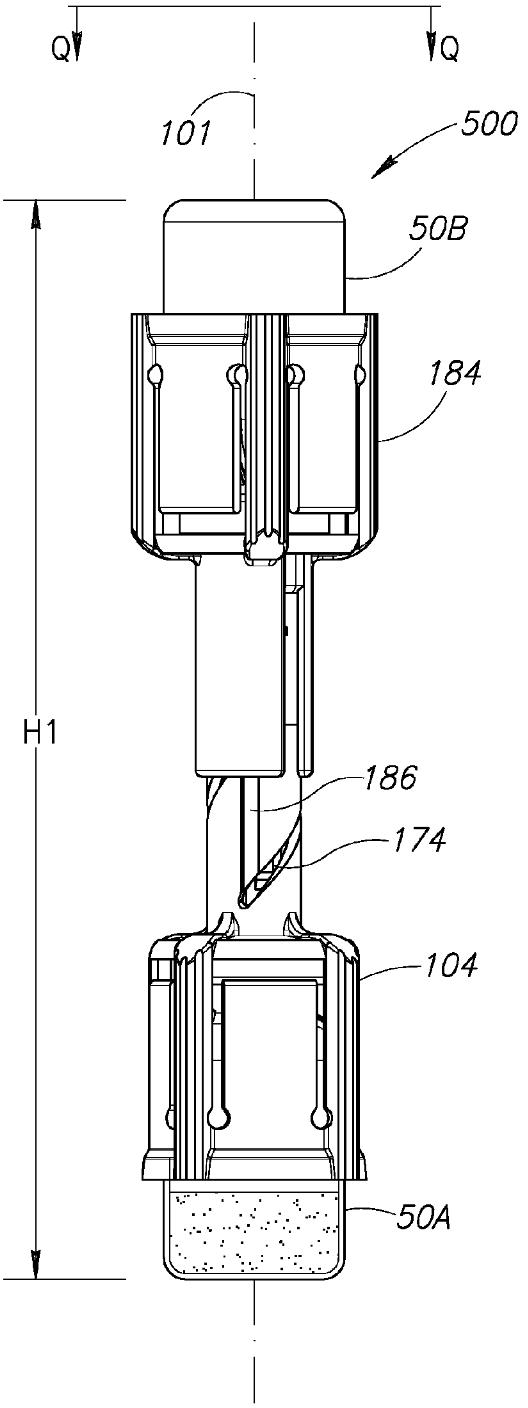
FIG. 26A is a front elevation view of FIG. 23's liquid drug transfer device in a pre-actuated state attached to a large drug vial and a large drug vial.
Figure 26B:
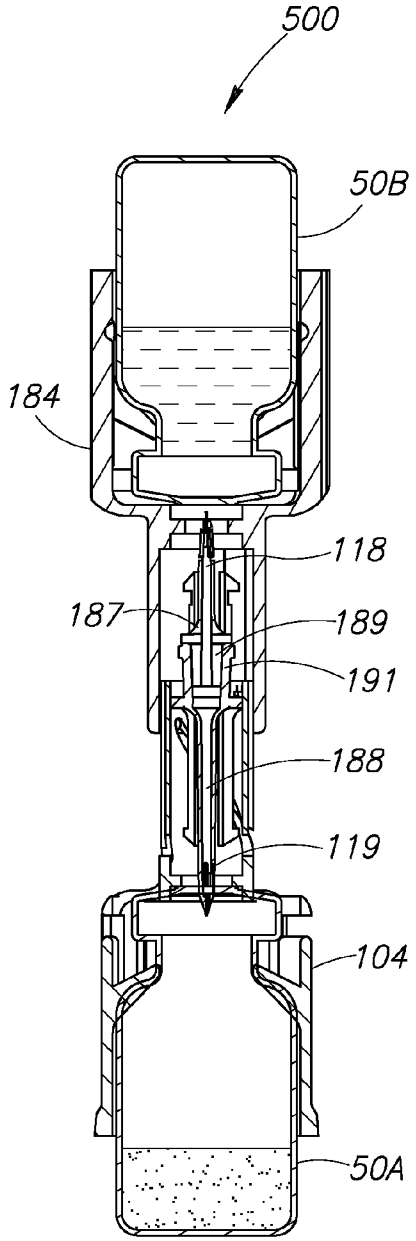
FIG. 26B is a longitudinal cross section of FIG. 26A's assemblage along line Q-Q thereon.

FIGS. 26 to 30 show the use of the liquid drug transfer device 500 as follows:

FIGS. 26A and 26B show the liquid drug transfer device 500 in a pre-actuated state attached to a large drug vial 50A and a large liquid vial 50B. The pair of minor stops 182 and the pair of major stops 183 retain the liquid transfer member 103 in the drug vial adapter stem 137. The pair of inward directed radial pins 173 are deployed at the start track ends 176A.

Figure 27A:
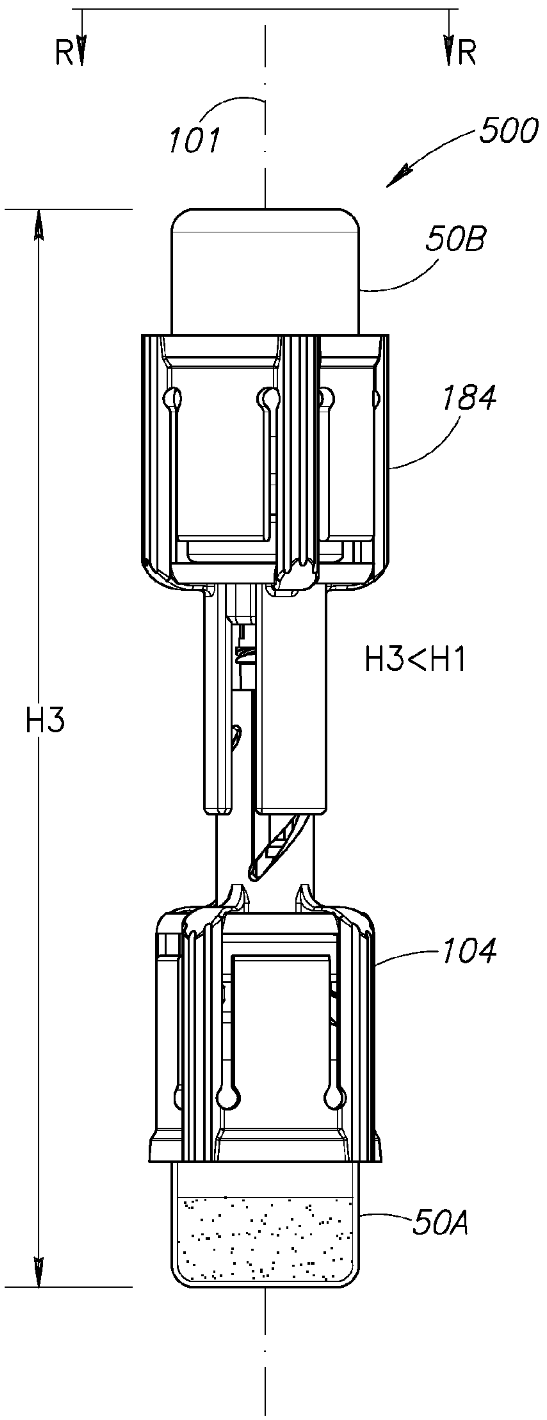
FIG. 27A is a front elevation view of FIG. 26A's assemblage in an intermediate actuated state pursuant to a liquid container flow communication step.
Figure 27B:
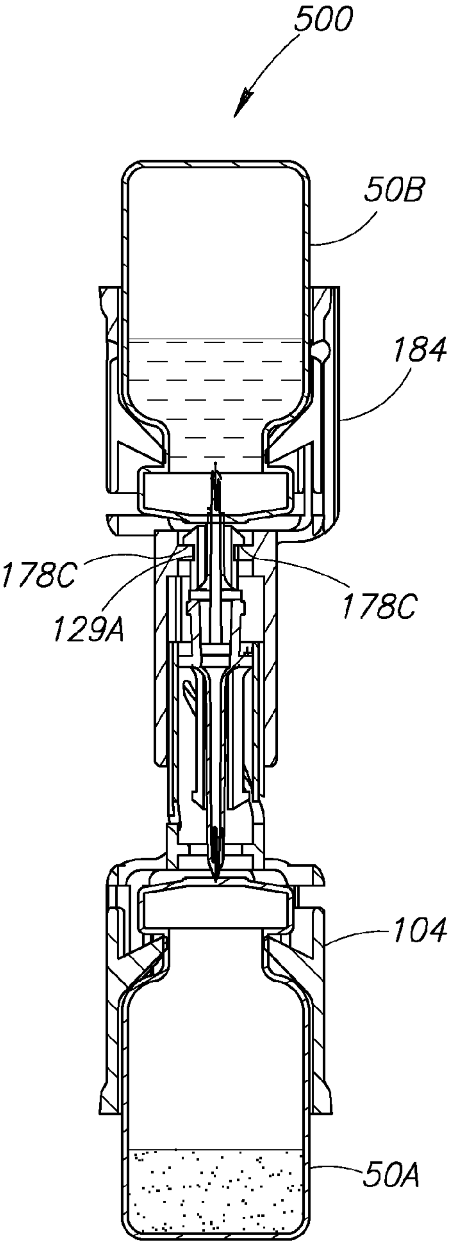
FIG. 27B is a longitudinal cross section of FIG. 27A's liquid drug transfer device along line R-R thereon.

FIGS. 27A and 27B show the liquid drug transfer device 500 in an intermediate actuated state pursuant to a liquid container flow communication step. The liquid drug transfer device 500 has an intermediate actuated height H3 where H3<H1. The pair of inward directed radial pins 173 are midway along the pair of opposite tracks 174 between the start track ends 176A and the finish track ends 176B. The retaining member tips 178A are snap fitted on the liquid vial adapter 184 thereby securing the liquid vial component 187 thereto.

Figure 28A:
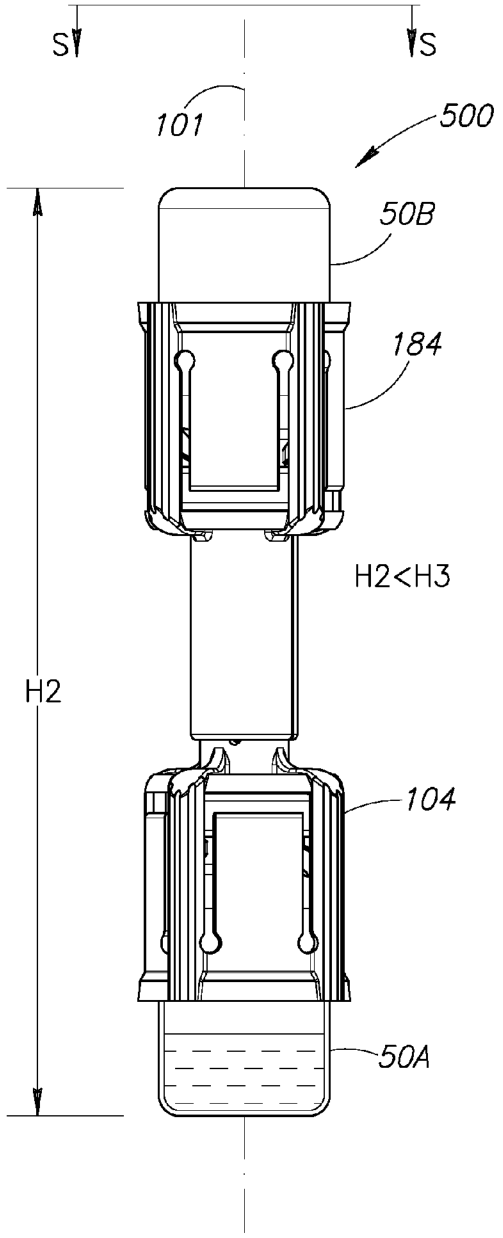
FIG. 28A is a front elevation view of FIG. 26A's assemblage in a post-actuated state pursuant to a drug vial flow communication step.
Figure 28B:
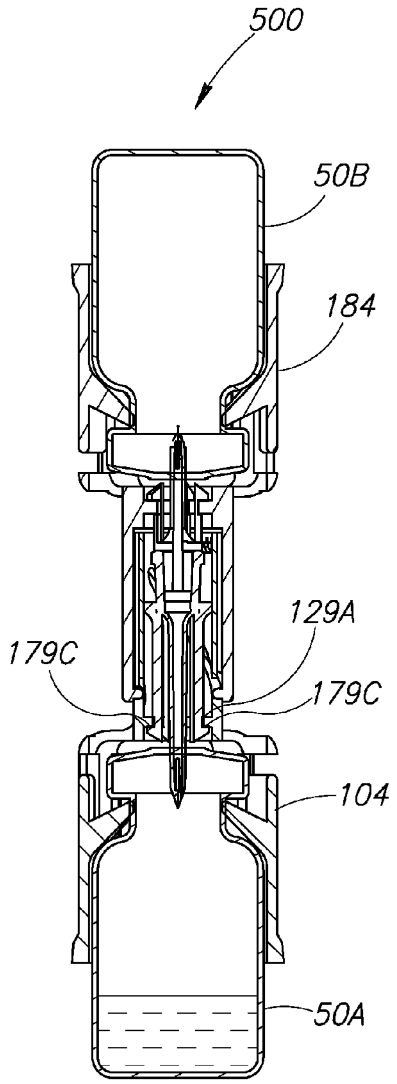
FIG. 28B is a longitudinal cross section of FIG. 28A's assemblage along line S-S thereon.

FIGS. 28A and 28B show the liquid drug transfer device 500 in a post-actuated state after a full linear compaction along the longitudinal device axis 101 following a full manual rotation of the drug vial adapter 104 with respect to the liquid vial adapter 184. The liquid drug transfer device 500 has a post-actuated height H2 where H2<H3. The retaining member tips 179A are snap fitted on the drug vial adapter 104 thereby securing the drug vial component 188 thereto. Full compaction establishes flow communication between the liquid vial 50B and the drug vial 50A whereupon the negative pressure in the drug vial 50A draws liquid contents from the liquid vial 50B thereinto for mixing and/or reconstitution purposes, thereby leaving the liquid vial 50B empty.

Figure 29A:
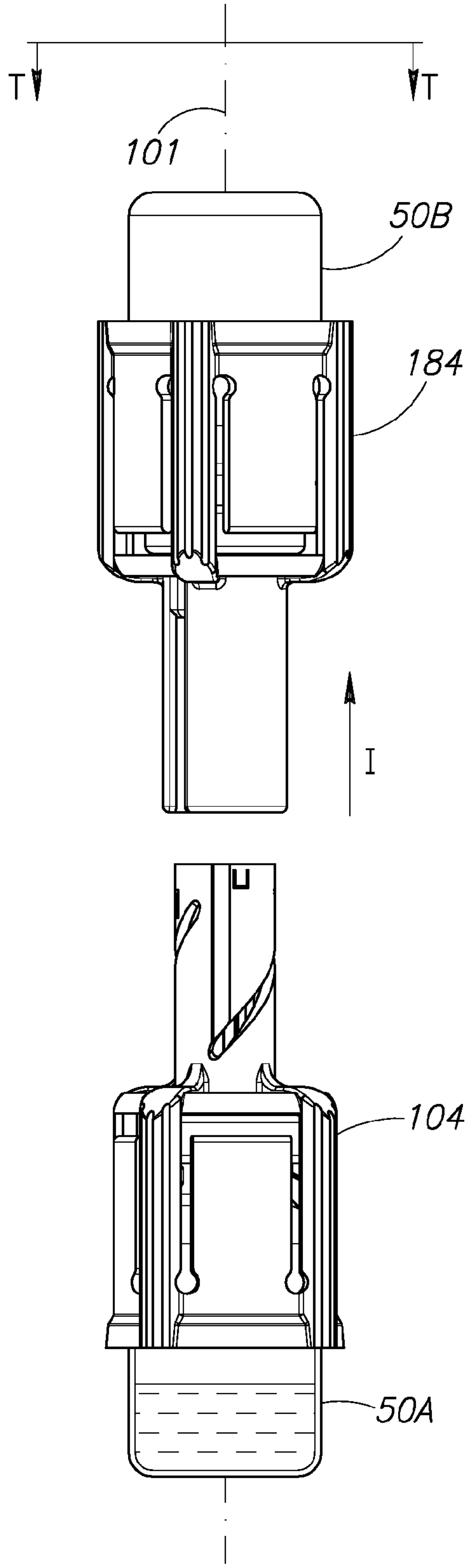
FIG. 29A is a front elevation view showing detachment of the liquid vial adapter and the drug vial adapter.
Figure 29B:
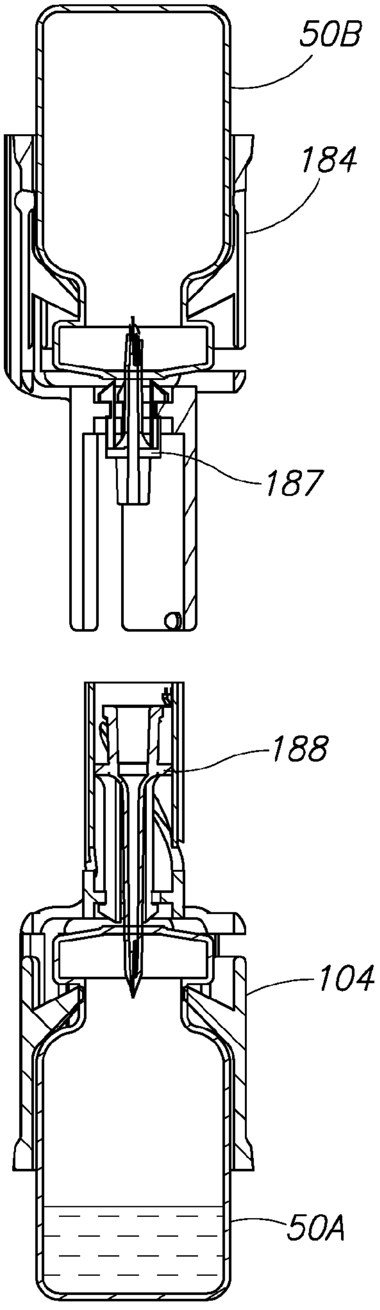
FIG. 29B is a longitudinal cross section of FIG. 29A's liquid vial adapter and drug vial adapter along line T-T thereon.

FIGS. 29A and 29B show longitudinal detachment of the liquid vial adapter 184 from the drug vial adapter 104 along the longitudinal device axis 101 as depicted by the arrow I. Longitudinal detachment is achieved by aligning the pair of the inward directed radial pins 173 with the pair of axial directed release grooves 186. The liquid transfer member 103 separates into its liquid vial component 187 and drug vial component 188 such that the liquid vial adapter 184 detaches with its now empty liquid vial 50B and the liquid vial component 187 and the drug vial adapter 104 detaches with its drug vial 50A now filled with liquid drug contents and the drug vial component 188.

Figure 30A:
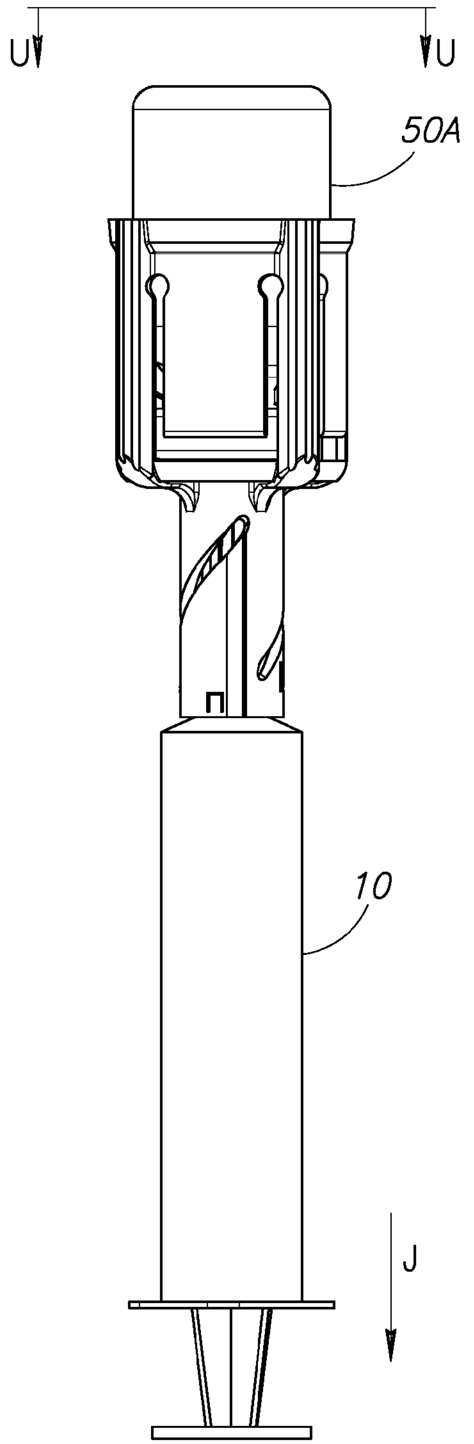
FIG. 30A is a front elevation view of syringe aspiration of liquid drug contents from the drug vial.
Figure 30B:
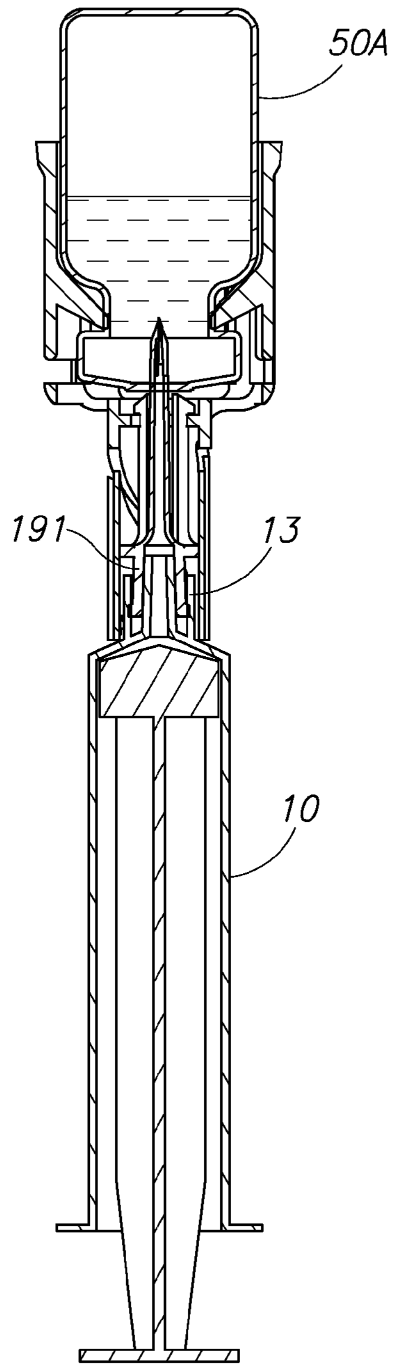
FIG. 30B is a longitudinal cross section of FIG. 30A's assemblage along line U-U thereon.

FIGS. 30A and 30B show attachment of an initial empty syringe 10 to the female connector 191 and inversion of the assemblage for syringe aspiration of liquid drug contents from the drug vial 50A as denoted by arrow J to prepare the filled syringe 10 as shown in FIG. 23.

While the invention has been described with respect to a limited number of embodiments, it will be appreciated that many variations, modifications, and other applications of the invention can be made within the scope of the appended claims.

The invention claimed is:

1. A liquid drug transfer device for dual flow communication step actuation for establishing flow communication between a liquid container and a drug vial, the liquid container containing liquid contents, the drug vial having a drug vial bottle, a drug vial interior containing a medicament, a drug vial stopper, an uppermost drug vial surface, and a drug vial closure, the liquid drug transfer device having a longitudinal device axis and comprising:

(a) a liquid container adapter for attachment to the liquid container;

(b) a dual ended liquid transfer member having a leading liquid transfer member end for flow communication with the liquid container, and a trailing liquid transfer member end in flow communication with said leading liquid transfer member end and terminating in a puncturing tip for puncturing the drug vial stopper for flow communication with the drug vial interior; and (c) a drug vial adapter having a transverse vial adapter top wall with an inner top wall rim defining a throughgoing top wall aperture along the longitudinal device axis, a downward depending vial adapter skirt for telescopic clamping on the drug vial closure such that said throughgoing top wall aperture overlies the uppermost drug vial surface, and an axial directed upright tubular drug vial adapter stem encircling said throughgoing top wall aperture and opposite said downward depending vial adapter skirt and engaging said dual ended liquid transfer member in a pre-actuated state of the liquid drug transfer device, the arrangement being such that in the pre-actuated state of the liquid drug transfer device having a pre-actuated height H1, said liquid transfer member is disposed in said drug vial adapter stem such that said puncturing tip overlies the uppermost drug vial surface, whereby a manual rotation of said drug vial adapter relative to said liquid container adapter about said longitudinal device axis compacts the liquid drug transfer device therealong to a post-actuated height H2 where H2<H1 and executes the following two flow communication steps:

i) a drug vial flow communication step for urging said puncturing tip along a linear displacement to puncture through the drug vial stopper for flow communication with the drug vial interior, and ii) a liquid container flow communication step for establishing flow communication between said leading liquid transfer member end and the liquid container.

2. The device according to claim 1, wherein the liquid container is an infusion liquid container having an access port, said liquid container adapter is constituted by an access port adapter for attachment to the access port, said leading liquid transfer member end engages said access port adapter and said trailing liquid transfer member end engages said drug vial adapter, and said leading liquid transfer member end includes an access port flow member for insertion into the access port during said manual rotation for execution of the dual flow communication step actuation.

3. The device according to claim 1, wherein the liquid container is an infusion liquid container having an access port, said liquid container adapter is constituted by an access port adapter for attachment to the access port, said leading liquid transfer member end engages said access port adapter and said trailing liquid transfer member end engages said drug vial adapter, said access port adapter includes an access port flow member for insertion into the access port on attaching the access port adapter to the infusion liquid container, and said leading liquid transfer member end includes an infusion liquid container stopcock arrangement for selective closing and opening flow communication with said access port flow member.

4. The device according to claim 1, wherein said liquid container adapter includes an axial directed upright tubular liquid container adapter stem for engaging said drug vial adapter stem and said liquid transfer member is slidingly disposed in said drug vial adapter stem.

5. The device according to claim 4, wherein the liquid container is an infusion liquid container having an access port, said liquid container adapter is constituted by an access port adapter for attachment to the access port, said leading liquid transfer member end includes an access port flow member for sliding insertion into the access port during said manual rotation of said drug vial adapter relative to said liquid container adapter.

6. The device according to claim 4, wherein the liquid container is an infusion liquid container having an access port, said liquid container adapter is constituted by an access port adapter for attachment to the access port, said access port adapter includes an access port flow member for insertion into the access port on attaching the access port adapter to the infusion liquid container, and said leading liquid transfer member end includes an infusion liquid container stopcock arrangement for selective closing and opening flow communication with said access port flow member.

7. The device according to claim 4, wherein the liquid container is constituted by a liquid vial containing liquid contents, the liquid vial having a liquid vial bottle, a liquid vial interior containing liquid contents, a liquid vial stopper, an uppermost liquid vial surface, and a liquid vial closure, said liquid container adapter is constituted by a liquid vial adapter having a transverse vial adapter top wall with an inner top wall rim defining a throughgoing top wall aperture, a downward depending vial adapter skirt for telescopic clamping on the liquid vial closure such that said throughgoing top wall aperture overlies the uppermost liquid vial surface, and said axial directed upright tubular liquid container stem encircling said throughgoing top wall aperture and opposite said downward depending vial adapter skirt, said liquid vial adapter being detachable from said drug vial adapter for providing access for syringe aspiration of liquid contents from the drug vial.

8. The device according to claim 7, wherein said liquid transfer member has a dual component construction including a drug vial component and a liquid vial component in detachable initially sealed connection with said drug vial component in said pre-actuated state, said drug vial component remaining attached to said drug vial adapter and said liquid vial component remaining attached to said liquid vial adapter on said detachment of said liquid vial adapter from said drug vial adapter, and said drug vial component having an exposed connector for providing said syringe aspiration of liquid drug contents from the drug vial.

9. The device according to claim 7, wherein the drug vial is under negative pressure and said manual rotation executes an initial liquid container flow communication step and a subsequent drug vial flow communication step thereby enabling said negative pressure to draw liquid contents from the liquid vial into the drug vial.

10. The device according to claim 1, for providing a user indication for indicating establishment of flow communication between the liquid container and the drug vial.

11. The device according to claim 1, and including a pre-attached initially intact drug vial.

12. A liquid drug transfer device for dual flow communication step actuation for establishing flow communication between a liquid container and a drug vial for reconstituting or mixing a powdered medicament contained in the drug vial, the liquid container containing liquid contents, the drug vial having a drug vial bottle, a drug vial interior containing a the medicament, a drug vial stopper, an uppermost drug vial surface, and a drug vial closure, the liquid drug transfer device having a longitudinal device axis and comprising:

(a) a liquid container adapter for attachment to the liquid container;

(b) a dual ended liquid transfer member having a leading liquid transfer member end for flow communication with the liquid container, and a trailing liquid transfer member end in flow communication with said leading liquid transfer member end and terminating in a puncturing tip for puncturing the drug vial stopper for flow communication with the drug vial interior; and (c) a drug vial adapter having a transverse vial adapter top wall with an inner top wall rim defining a throughgoing top wall aperture along the longitudinal device axis, a downward depending vial adapter skirt for telescopic clamping on the drug vial closure such that said throughgoing top wall aperture overlies the uppermost drug vial surface, and an axial directed upright tubular drug vial adapter stem encircling said throughgoing top wall aperture and opposite said downward depending vial adapter skirt and engaging said dual ended liquid transfer member in a pre-actuated state of the liquid drug transfer device, the arrangement being such that in the pre-actuated state of the liquid drug transfer device having a pre-actuated height H1, said liquid transfer member is disposed in said drug vial adapter stem such that said puncturing tip overlies the uppermost drug vial surface, and being arranged to convert a manual rotation of said drug vial adapter relative to said liquid container adapter about said longitudinal device axis into a linear displacement that compacts the liquid drug transfer device therealong to a post-actuated height H2 where H2<H1 and executes the following two flow communication steps to cause liquid contents to flow from the liquid container into the drug vial:

i) a drug vial flow communication step for urging said puncturing tip along a linear displacement to puncture through the drug vial stopper for flow communication with the drug vial interior, and ii) a liquid container flow communication step for establishing flow communication between said leading liquid transfer member end and the liquid container.

13. The device according to claim 12, wherein the liquid container is an infusion liquid container having an access port, said liquid container adapter is constituted by an access port adapter for attachment to the access port, said leading liquid transfer member end engages said access port adapter and said trailing liquid transfer member end engages said drug vial adapter, and said leading liquid transfer member end includes an access port flow member for insertion into the access port during said manual rotation for execution of the dual flow communication step actuation.

14. The device according to claim 12, wherein the liquid container is an infusion liquid container having an access port, said liquid container adapter is constituted by an access port adapter for attachment to the access port, said leading liquid transfer member end engages said access port adapter and said trailing liquid transfer member end engages said drug vial adapter, said access port adapter includes an access port flow member for insertion into the access port on attaching the access port adapter to the infusion liquid container, and said leading liquid transfer member end includes an infusion liquid container stopcock arrangement for selective closing and opening flow communication with said access port flow member.

15. The device according to claim 12, wherein said liquid container adapter includes an axial directed upright tubular liquid container adapter stem for engaging said drug vial adapter stem and said liquid transfer member is slidingly disposed in said drug vial adapter stem.

16. The device according to claim 15, wherein the liquid container is an infusion liquid container having an access port, said liquid container adapter is constituted by an access port adapter for attachment to the access port, said leading liquid transfer member end includes an access port flow member for sliding insertion into the access port during said manual rotation of said drug vial adapter relative to said liquid container adapter.

17. The device according to claim 15, wherein the liquid container is an infusion liquid container having an access port, said liquid container adapter is constituted by an access port adapter for attachment to the access port, said access port adapter includes an access port flow member for insertion into the access port on attaching the access port adapter to the infusion liquid container, and said leading liquid transfer member end includes an infusion liquid container stopcock arrangement for selective closing and opening flow communication with said access port flow member.

18. The device according to claim 15, wherein the liquid container is constituted by a liquid vial containing liquid contents, the liquid vial having a liquid vial bottle, a liquid vial interior containing liquid contents, a liquid vial stopper, an uppermost liquid vial surface, and a liquid vial closure, said liquid container adapter is constituted by a liquid vial adapter having a transverse vial adapter top wall with an inner top wall rim defining a throughgoing top wall aperture, a downward depending vial adapter skirt for telescopic clamping on the liquid vial closure such that said throughgoing top wall aperture overlies the uppermost liquid vial surface, and said axial directed upright tubular liquid container stem encircling said throughgoing top wall aperture and opposite said downward depending vial adapter skirt, said liquid vial adapter being detachable from said drug vial adapter for providing access for syringe aspiration of liquid contents from the drug vial.

19. The device according to claim 18, wherein said liquid transfer member has a dual component construction including a drug vial component and a liquid vial component in detachable initially sealed connection with said drug vial component in said pre-actuated state, said drug vial component remaining attached to said drug vial adapter and said liquid vial component remaining attached to said liquid vial adapter on said detachment of said liquid vial adapter from said drug vial adapter, and said drug vial component having an exposed connector for providing said syringe aspiration of liquid drug contents from the drug vial.

20. The device according to claim 18, wherein the drug vial is under negative pressure and said manual rotation executes an initial liquid container flow communication step and a subsequent drug vial flow communication step thereby enabling said negative pressure to draw liquid contents from the liquid vial into the drug vial.

21. The device according to claim 12, for providing a user indication for indicating establishment of flow communication between the liquid container and the drug vial.

22. The device according to claim 12, and including a pre-attached initially intact drug vial.

* * * * *